US008686018B2

(12) United States Patent
Spyvee et al.

(10) Patent No.: US 8,686,018 B2
(45) Date of Patent: Apr. 1, 2014

(54) PHARMACEUTICAL COMPOSITION

(71) Applicant: Eisai R&D Management Co., Ltd., Tokyo (JP)

(72) Inventors: Mark Spyvee, Hampstead, NH (US); Takashi Satoh, Andover, MA (US); Jonathan Eric Carlson, Merrimack, NH (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 13/795,768

(22) Filed: Mar. 12, 2013

(65) Prior Publication Data

US 2013/0237578 A1    Sep. 12, 2013

Related U.S. Application Data

(63) Continuation of application No. PCT/US2011/051163, filed on Sep. 12, 2011.

(60) Provisional application No. 61/384,781, filed on Sep. 21, 2010.

(51) Int. Cl.
*A61K 31/415* (2006.01)
*C07D 231/20* (2006.01)
*A61P 29/00* (2006.01)

(52) U.S. Cl.
USPC ....................................... 514/407; 548/369.7

(58) Field of Classification Search
None
See application file for complete search history.

(56) References Cited

U.S. PATENT DOCUMENTS

| | | | |
|---|---|---|---|
| 6,589,970 | B2 | 7/2003 | Commons et al. |
| 6,710,054 | B2 | 3/2004 | Nakao et al. |
| 7,119,108 | B1 | 10/2006 | Makriyannis et al. |
| 7,141,580 | B2 | 11/2006 | Nakao et al. |
| 7,189,715 | B2 | 3/2007 | Jerussi et al. |
| 7,196,089 | B2 | 3/2007 | Oxford et al. |
| 7,238,714 | B2 | 7/2007 | Nakao et al. |
| 7,393,842 | B2 | 7/2008 | Makriyannis et al. |
| 7,479,564 | B2 | 1/2009 | Nakao et al. |
| 7,507,754 | B2 | 3/2009 | Oxford et al. |
| 7,528,157 | B2 | 5/2009 | Oxford et al. |
| 8,008,927 | B1 | 8/2011 | Hronik |
| 8,293,917 | B2 * | 10/2012 | Cook et al. .................. 546/275.4 |
| 8,324,265 | B2 | 12/2012 | Kurose et al. |
| 2004/0235831 | A1 | 11/2004 | Rozot et al. |
| 2005/0113283 | A1 | 5/2005 | Solow-Cordero et al. |
| 2009/0170832 | A1 | 7/2009 | Kurose et al. |
| 2010/0144785 | A1 | 6/2010 | Desbordes et al. |
| 2010/0184994 | A1 | 7/2010 | Nett et al. |
| 2010/0197662 | A1 | 8/2010 | Ogawa et al. |
| 2010/0292236 | A1 | 11/2010 | Li et al. |
| 2011/0028463 | A1 | 2/2011 | Nozawa et al. |
| 2011/0144153 | A1 | 6/2011 | Nozawa et al. |

FOREIGN PATENT DOCUMENTS

| | | |
|---|---|---|
| JP | H04-21671 | 1/1992 |
| WO | WO 2005/021508 A1 | 3/2005 |
| WO | WO 2005/070889 A1 | 8/2005 |
| WO | WO 2007/143825 A1 | 12/2007 |
| WO | WO 2008/017164 A1 | 2/2008 |
| WO | WO 2008/071736 A1 | 6/2008 |
| WO | WO 2008/104055 A1 | 9/2008 |
| WO | WO 2009/056582 A1 | 5/2009 |
| WO | WO 2010/012794 A1 | 2/2010 |
| WO | WO 2010/034110 A1 | 4/2010 |

OTHER PUBLICATIONS

Baryawno et al., Tumor-growth-promoting cyclooxygenase-2 prostaglandin $E_2$ pathway provides medulloblastoma therapeutic targets, *Neuro-Oncology* 2008, 10(5): 661-674.

Boniface et al., Prostaglandin E2 Regulates Th17 cell differentiation and function through cyclic AMP and EP2/EP4 receptor signaling, *The Journal of Experimental Medicine* 2009, 206(3), 535-548.

Buono et al., T-bet deficiency reduces atherosclerosis and alters plaque antigen-specific immune responses, *Proceedings of National Academy of Sciences of the United States of America* Feb. 1, 2005, 102(5): 1596-1601.

Cesare et al., The IL-23/Th17 Axis in the Immunopathogenesis of Psoriasis, *Journal of Investigative Dermatology* 2009, 129: 1339-1350; doi:10.1038/jid,2009.59.

Chan et al., Imbalance of Th1/Th2 transcription factors in patients with lupus nephritis, *Rheumatology (Oxford)* 2006, 45: 951-957.

Chell et al., Increased Ep4 Receptor Expression in Colorectal Cancer Progession Promotes Cell Growth and Anchorage Independence, *Cancer Research* 2006, 66: 3106-3113.

Chizzolini et al., Prostaglandin $E_2$ synergistically with interleukin-23 favors human Th17 expansion, *Blood* 2008, 112: 3696-3703.

(Continued)

*Primary Examiner* — Kamal Saeed
(74) *Attorney, Agent, or Firm* — Myers Bigel Sibley & Sajovec, P.A.

(57) ABSTRACT

The present invention provides compounds of Formula I:

along with pharmaceutical compositions containing the same, and methods of use thereof in subjects in need of treatment.

24 Claims, 1 Drawing Sheet

(56) References Cited

OTHER PUBLICATIONS

Dougados et al,, Efficacy of Celecoxib, a Cyclooxygenase 2—Specific Inhibitor, in the Treatment of Ankylosing Spondylitis: A Six-Week Controlled Study with Comparison Against Placebo and Against a Conventional Nonsteroidal Antiinflammatory Drug, *Arthritis & Rheumatism* 2001, 44(1): 180-185.

Elmets et al., Chemoprevention of Nonmelanoma Skin Cancer With Celecoxib: A Randomized, Double-Blind, Placebo-Controlled Trial, *Journal of the National Cancer Institute* Nov. 29, 2010, 102: 1835-1844.

Ghoreschi et al., A molecule solves psoriasis? Systemic therapies for psoriasis inducing interleukin 4 and Th2 responses, *Journal of Molecular Medicine* 2003, 81: 471-480.

Gilbert et al., Pyrazolidine-3, 5-diones and 5-Hydroxy-1H-pyrazol-3(2H)-ones, Inhibitors of UDP-N-acetylenolpyruvyl Glucosamine Re-ductase, *Journal of Medicinal Chemistry* 2006, 49(20): 6027-6036.

Hölttä et al., IL-23/IL-17 Immunity as a Hallmark of Crohn's Disease, *Inflammatory Bowel Diseases* Sep. 9, 2008, 14(9): 1175-1184.

Hoshikawa et al., Expression of prostaglandin $E_2$ receptors in oral squamous cell carcinomas and growth inhibitory effects of an EP3 selective antagonist, ONO-AE3-240, *International Journal of Oncology* 2009, 34: 847-852.

International Union of Pure and Applied Chemistry (IUPAC): Rules for the Nomenclature of Organic Chemistry Section E: Stereochemistry, *Pure & Applied Chemistry* 1975, 45(1): 11-30.

Iwanami et al., Crucial Role Of II-6/II-17 Axis in the Induction of Arthritis by Glucose-6-Phosphate Isomerase, *Arthritis and Rheumatism* Mar. 3, 2008, 58(3):754-763.

Jabbour et al., Prostaglandin $E_2$ Induces Proliferation of Glandular Epithelial Cells of Human Endometrium via Extracellular Regulated Kinase 1/2-Mediated Pathway, *Journal of Clinical Endocrinology & Metabolism* 2003, 88(9): 4481-4487.

Jandus et al., Increased Nos. of Circulating Polyfunctional Th17 Memory Cells in Patients With Seronegative Spondylarthritides, *Arthritis & Rheumatism* 2008, 58(8): 2307-2317.

Juedes et al., T-bet Controls Autoaggressive CD8 Lymphocyte Response in Type I Diabetes, *Journal of Experimental Medicine* Apr. 19, 2004, 199(8): 1153-1162.

Kundu et al., Antagonism of the prostaglandin E Receptor EP4 inhibits metastasis and enhances NK function, *Breast Cancer Research and Treatment* 2009, 117: 235-242.

Lin et al., Prostaglandin $E_2$ Receptor EP4 Contributes to Inflammatory Pain Hypersensitivity, *Journal of Pharmacology and Experimental Therapeutics* 2006, 319(3): 1096-1103.

Liu et al., Cox-2 expression is correlated with VEGF-C, lymphangiogenesis and lymph node metastasis in human cervical cancer, *Microvascular Research* Sep. 2, 2011, 82(2):131-140.

Ma et al., Prostaglandin E Receptor Ep4 Antagonism Inhibits Breast Cancer Metastasis, *Cancer Research* 2006, 66: 2923-2927.

Maubach et al., BGC20-1531, a novel, potent, and selective $EP_4$ receptor antagonist: a putative new treatment for migraine headache, *British Journal of Pharmacology* 2009, 156: 316-327.

McCoy et al., The role of prostaglandin E2 receptors in the pathogenesis of rheumatoid arthritis, *Journal of Clinical Investigation* 2002, 110(5): 651-658.

Miyata et al., Pathological function of prostaglandin E2 receptors in transitional cell carcinoma of the upper urinary tract, *Virchows Archiv* 2006, 448: 822-829.

Napolitani et al., Prostaglandin E2 enhances Th17 responses via modulation of IL-17 and IFN-γ production by memory CD4+ T Cells, *European Journal of Immunology* 2009, 39: 1301-1312.

Narumiya, S. In *The Prostanoid Receptors in Signaling Network of Chronic Inflammation—The Role of FP in Bleomycin-induced Pulmonary Fibrosis and The Role of EP4 in Experimental Autoimmune Encephalomyelitis in Mice*, Eicosanoids and Chronic Inflammation, Keystone Symposia, Montana, Jan. 9, 2008 (Abstract Only).

Payner et al., Microsomal prostaglandin E synthase-1 regulates human glioma cell growth via prostaglandin $E_2$-dependent activation of type II protein kinase A, *Molecular Cancer Therapy* 2006, 5: 1817-1826.

Peng et al., T-bet regulates IgG class switching and pathogenic auto antibody production, *Proceedings of National Academy of Sciences of the United States of America* Apr. 16, 2002, 99(8): 5545-5550.

Potential new drug targets against hormone-dependent breast cancer identified, *Expert Review of Anticancer Therapy* 2008, 8(4): 507-509.

Rask et al., Ovarian epithelial cancer: a role for $PGE_2$ synthesis and signaling in malignant transformation and progression, *Molecular Cancer* 2006, 5: 62.

Sasaki et al., Identification of a novel type 1 diabetes susceptibility gene, T-bet, *Human Genetics* 2004, 115: 177-184.

Sharma et al., Tumor Cyclooxygenase-2/Prostaglandin E2-Dependent Promotion of FOXP3 Expression and CD4+CD25+ T Regulatory Cell Activities in Lung Cancer, *Cancer Research* 2005, 65: 5211-5220.

Sheibanie et al., Prostaglandin E2 Exacerbates Collagen-Induced Arthritis in Mice Through the Inflammatory Interleukin-23/Interleukin-17 Axis, *Arthritis and Rheumatism* 2007, 56(8): 2608-2619.

Sheibanie et al., The Proinflammatory Effect of Prostaglandin $E_2$ in Experimental Inflammatory Bowel Disease is Mediated through the IL-23→IL-17 Axis, *Journal of Immunology* 2007, 178: 8138-8147.

Terada et al., Identification of EP4 as a Potential Target for the Treatment of Castration-Resistant Prostate Cancer Using A Novel Xenograft Model, Cancer Research 2010, 70: 1606-1615.

Wanders et al., Nonsteroidal Antiinflammatory Drugs Reduce Radiographic Progression in Patients With Ankylosing Spondylitis: A Randomized Clinical Trial, *Arthritis & Rheumatism* Jun. 6, 2005, 52(6): 1756-1765.

Whiteside, Inhibiting the inhibitors: evaluating agents targeting cancer immunosuppression, *Expert Opinion in Biological Therapy* 2010, 10(7): 1019-35.

Williams, Collagen-Induced Arthritis as a Model for Rheumatoid Arthritis, *Methods Molecular Medicine* 2004, 98: 207-216.

Woodhams et al., Localisation and modulation of prostanoid receptors EPI and EP4 in the rat chronic constriction injury model of neuropathic pain, *European Journal of Pain* 2007, 11(6): 605-613.

Wu et al., Prostaglandin $E_2$ Regulates Renal Cell Carcinoma Invasion Through the EP4 Receptor-Rap Signal Transduction Pathway, *Journal of Biological Chemistry* Aug. 10, 2011, 286: 33954-33962.

Yang et al., Host and Direct Antitumor Effects and Profound Reduction in Tumor Metastasis With Selective EP4 Receptor Antagonism, *Cancer Research* 2006, 66: 9665-9672.

Yao et al, Prostaglandin $E_2$-EP4 signaling promotes immune inflammation through $T_H1$ cell differentiation and $T_H17$ cell expansion, *Nature Medicine* 2009, 15(6): 633-640.

\* cited by examiner

PHARMACEUTICAL COMPOSITION

RELATED APPLICATIONS

This application is a continuation of PCT/US11/51163, filed Sep. 12, 2011, which application claims the benefit of U.S. Provisional Patent Application No. 61/384,781, filed Sep. 21, 2010, the disclosures of each of which are incorporated by reference herein in their entireties.

BACKGROUND OF THE INVENTION

Upon encountering antigen, naive CD4+ T helper precursor (Thp) cells are differentiated into two distinct subsets, Type 1 T helper (Th1) and Type 2 T helper (Th2). Recently, a novel T cell subset, the Th17 cells, has also been identified and characterized These differentiated Th cells are defined both by their distinct functional abilities and by unique cytokine profiles. Specifically, Th1 cells produce interferon-gamma, interleukin (IL)-2, and tumor necrosis factor (TNF)-beta, which activate macrophages and are responsible for cell-mediated immunity and phagocyte-dependent protective responses. In contrast, Th2 cells are known to produce IL-4, IL-5, IL-6, IL-9, IL-10 and IL-13, which are responsible for strong antibody production, eosinophil activation, and inhibition of several macrophage functions, thus providing phagocyte-independent protective responses. Th17 cells mainly produce IL-17A, IL-17F, IL-21, IL-22 & TNF and are required for host defense against extracellular pathogens and are critical mediators of autoimmunity. Accordingly, Th1, Th2, and Th17 cells are associated with different immunopathological responses.

In addition, the development of each type of Th cell is mediated by a different cytokine pathway. Specifically, it has been shown that IL-4 promotes Th2 differentiation and simultaneously blocks Th1 development. In contrast, IL-12, IL-18 and IFN-gamma are the cytokines critical for the development of Th1 cells. In murine, TGF-β & IL-6 are critical for the induction of Th17 cell differentiation, while in human, IL-1, IL-6 & IL-23 are important drivers of Th17 cell development. Accordingly, effective immunologic homeostasis relies on a continual balance between helper T cell activation and regulatory T cell (Treg) suppression.

Th1 cells are involved in the pathogenesis of a variety of organ-specific autoimmune disorders, Crohn's disease, *Helicobacter pylori*-induced peptic ulcer, acute kidney allograft rejection, and unexplained recurrent abortions. In contrast, allergen-specific Th2 responses are responsible for atopic disorders in genetically susceptible individuals. Moreover, Th2 responses against still unknown antigens predominate in Omenn's syndrome, idiopathic pulmonary fibrosis, and progressive systemic sclerosis. Th17 cells cause immunopathology in different models of autoimmunity, such as rheumatoid arthritis, multiple sclerosis, Crohn's disease and psoriasis. IL-17 (the signature Th-17 cytokine) knock-out mice show marked resistance to inflammatory arthritis development. Joint destruction in the CIA model can be ameliorated by the administration of a neutralizing anti-IL-17 antibody.

There remains a high unmet medical need to develop new therapeutic treatments that are useful in treating the various conditions associated with imbalanced Th1/Th2 and Th17 cellular differentiation. For many of these conditions the currently available treatment options are inadequate. Accordingly, the Th1/Th2 and Th17 paradigm provides a rationale for the development of strategies for the therapy of allergic and autoimmune disorders.

Prostaglandins have been shown to modulate various phases of the immune response. The lipid mediator prostaglandin E2 (PGE2) is an eicasanoid that is well known to suppress $CD4^+$ T cell activation through elevation of intracellular cAMP and inactivation of lck. PGE2 has been also shown to play a role in regulating Th1 responses by suppression of interferon gamma (IFN-gamma) production and T cell proliferation. However PGE2 stimulation via the EP4 subtype of PGE2 receptor can also have the opposite effect, namely to promote Th1 differentiation (Prostaglandin E receptor subtypes EP2 and EP4 promote differentiation and expansion of Th1 and Th17 lymphocytes through different signaling modules, *Nature Medicine*, 2009, 15, 633-640) and IL-17 production in activated CD4+ cells. Prostaglandin E2 synergistically with interleukin-23 favors human Th17 expansion, *Blood*, 2008, 112, 3696-3703; Prostaglandin E2 regulates Th17 cell differentiation and function through cyclic AMP and EP2/EP4 receptor signaling, *J. Exp. Med.* 2009, 206, 535-548; Prostaglandin E2 enhances Th17 response via modulation of IL-17 and IFN-γ production by memory CD4+ T cells, *Eur. J. Immunol.* 2009, 39, 1301-1312. Consistent with this, antagonism of EP4 with either a novel selective EP4 antagonist or a PGE2-neutralizing antibody suppresses Th1 differentiation, Th17 expansion, as well as IL-23 secretion by activated dendritic cells. Induction of Th1 differentiation by PGE2 is mediated by PI3K signaling whereas stimulation of IL-17 production requires cAMP signaling. In addition, administration of an EP4 antagonist to DBA/1 or C57BL/6 mice suppressed innate and adaptive immune responses, and suppressed disease in collagen induced arthritis (CIA) and experimental autoimmune encephalomyelitis (EAE) models, indicating that PGE2/EP4 signaling is critically involved in these autoimmune pathologies. These results suggest that suppression of PGE2/EP4 signaling may have therapeutic value in modifying inflammatory autoimmune diseases such as rheumatoid arthritis and multiple sclerosis.

SUMMARY OF THE INVENTION

As described herein, the present invention provides compounds of Formula I:

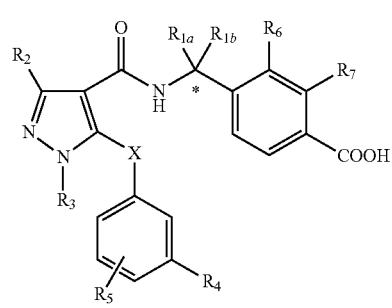

wherein:
one of $R_{1a}$ and $R_{1b}$ is hydrogen, and the other is methyl; or $R_{1a}$ and $R_{1b}$ are taken together to form a cyclopropyl ring;
$R_2$ is methyl or fluoromethyl (e.g., monofluoromethyl, difluoromethyl, trifluoromethyl);
$R_3$ is methyl;
$R_4$ is hydrogen, halo, fluoromethyl, methoxy, or fluoromethoxy (e.g., monofluoromethoxy, difluoromethoxy, trifluoromethoxy);

$R_5$ is hydrogen, halo, fluoromethyl, methoxy, or fluoromethoxy;

$R_6$ is hydrogen, halo, methyl, or methoxy;

$R_7$ is hydrogen, halo, methyl, or methoxy; and

X is oxygen;

or pharmaceutically acceptable salts thereof.

In some embodiments, one of $R_{1a}$ and $R_{1b}$ is hydrogen, and the other is methyl, and the carbon marked with a * is a stereogenic center. In some embodiments, one of $R_{1a}$ and $R_{1b}$ is hydrogen, and the other is methyl and the carbon marked with a * has the S-configuration. In some embodiments, one of $R_{1a}$ and $R_{1b}$ is hydrogen, and the other is methyl and the carbon marked with a * has the R-configuration.

In some embodiments, the present invention provides a pharmaceutical composition comprising a compound of Formula I or a subset or example thereof. In some embodiments, the invention provides a method of treating rheumatoid arthritis in a subject, comprising the step of administering to the subject a composition comprising a compound of Formula I or a subset or example thereof. In some embodiments, the invention provides a method of treating multiple sclerosis in a subject, comprising the step of administering to the subject a composition comprising a compound of Formula I or a subset or example thereof.

A further aspect of the invention is the use of a compound of Formula I or a subset or example thereof in the manufacture of a medicament for the treatment of rheumatoid arthritis. Another aspect of the invention is the use of a compound of formula I or a subset or example thereof in the manufacture of a medicament for the treatment of multiple sclerosis.

DETAILED DESCRIPTION OF CERTAIN EMBODIMENTS OF THE INVENTION

A. Definitions

Figure 1:
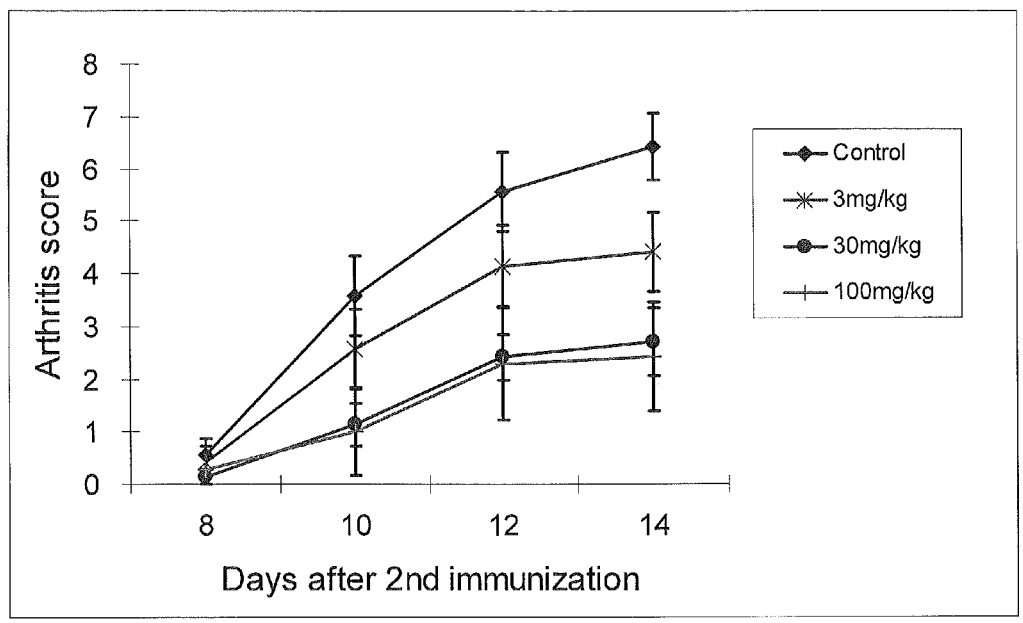
FIG. 1: Suppression of arthritis development in a CIA model with a compound of the present invention.

Compounds of this invention include those described generally above, and are further illustrated by the embodiments, sub-embodiments, and species disclosed herein. As used herein, the following definitions shall apply unless otherwise indicated.

As described herein, compounds of the invention may optionally be substituted with one or more substituents, such as are illustrated generally above, or as exemplified by particular classes, subclasses, and species of the invention. In general, the term "substituted" refers to the replacement of hydrogen radicals in a given structure with the radical of a specified substituent. Unless otherwise indicated, a substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

As used herein, the term "modulator of Th1 differentiation or Th17 expansion" or "modulator compound of Th1 differentiation or Th17 expansion" or "modulator compound" as used herein refers to a compound which suppresses, reduces or inhibits, differentiation of naive CD4+ T cells into Th1 cells. In some embodiments, the term "modulator of Th1 differentiation or Th17 expansion" or "modulator compound of Th1 differentiation or Th17 expansion" as used herein refers to a compound which suppresses, reduces or inhibits, the number of IL-17 producing CD4+ T cells or IL-17 production in activated CD4+ T cells.

"Isomers" refer to compounds having the same number and kind of atoms and hence the same molecular weight, but differing with respect to the arrangement or configuration of the atoms.

"Stereoisomers" refer to isomers that differ only in the arrangement of the atoms in space.

"Diastereoisomers" refer to stereoisomers that are not mirror images of each other.

"Enantiomers" refers to stereoisomers that are non-superimposable mirror images of one another.

Enantiomers include "enantiomerically pure" isomers that comprise substantially a single enantiomer, for example, greater than or equal to 90%, 92%, 95%, 98%, or 99%, or equal to 100% of a single enantiomer.

"Enantiomerically pure" as used herein means a compound, or composition of a compound, that comprises substantially a single enantiomer, for example, greater than or equal to 90%, 92%, 95%, 98%, or 99%, or equal to 100% of a single enantiomer.

"Stereomerically pure" as used herein means a compound or composition thereof that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of diastereomers, and substantially free of the enantiomer, of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. See, e.g., U.S. Pat. No. 7,189,715.

"R" and "S" as terms describing isomers are descriptors of the stereochemical configuration at an asymmetrically substituted carbon atom. The designation of an asymmetrically substituted carbon atom as "R" or "S" is done by application of the Cahn-Ingold-Prelog priority rules, as are well known to those skilled in the art, and described in the International Union of Pure and Applied Chemistry (IUPAC) Rules for the Nomenclature of Organic Chemistry. Section E, Stereochemistry.

"Enantiomeric excess" (ee) of an enantiomer is [(the mole fraction of the major enantiomer) minus (the mole fraction of the minor enantiomer)]×100.

"Stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

"Ar" or "aryl" refer to an aromatic carbocyclic moiety having one or more closed rings. Examples include, without limitation, phenyl, naphthyl, anthracenyl, phenanthracenyl, biphenyl, and pyrenyl.

"Heteroaryl" refers to a cyclic moiety having one or more closed rings, with one or more heteroatoms (for example, oxygen, nitrogen or sulfur) in at least one of the rings, wherein at least one of the rings is aromatic, and wherein the ring or rings may independently be fused, and/or bridged. Examples include without limitation quinolinyl, isoquinolinyl, indolyl, furyl, thienyl, pyrazolyl, quinoxalinyl, pyrrolyl, indazolyl, thieno[2,3-c]pyrazolyl, benzofuryl, pyrazolo[1,5-a]pyridyl, thiophenylpyrazolyl, benzothienyl, benzothiazolyl, thiazolyl, 2-phenylthiazolyl, and isoxazolyl.

"Alkyl" or "alkyl group," as used herein, means a straight-chain (i.e., unbranched), branched, or cyclic hydrocarbon chain that is completely saturated. In certain embodiments, alkyl groups contain 1-6 carbon atoms. In certain embodiments, alkyl groups contain 1-4 carbon atoms. In certain embodiments, alkyl groups contain 1-3 carbon atoms. In still other embodiments, alkyl groups contain 2-3 carbon atoms, and in yet other embodiments alkyl groups contain 1-2 carbon atoms. In certain embodiments, the term "alkyl" or "alkyl group" refers to a cycloalkyl group, also known as carbocycle. Non-limiting examples of exemplary alkyl groups include methyl, ethyl, propyl, isopropyl, butyl, cyclopropyl and cyclohexyl.

"Alkenyl" or "alkenyl group," as used herein, refers to a straight-chain (i.e., unbranched), branched, or cyclic hydrocarbon chain that has one or more double bonds. In certain embodiments, alkenyl groups contain 2-6 carbon atoms In certain embodiments, alkenyl groups contain 2-4 carbon atoms. In still other embodiments, alkenyl groups contain 3-4 carbon atoms, and in yet other embodiments alkenyl groups contain 2-3 carbon atoms. According to another aspect, the term alkenyl refers to a straight chain hydrocarbon having two double bonds, also referred to as "diene." In other embodiments, the term "alkenyl" or "alkenyl group" refers to a cycloalkenyl group. Non-limiting examples of exemplary alkenyl groups include —CH=CH$_2$, —CH$_2$CH=CH$_2$ (also referred to as allyl), —CH=CHCH$_3$, —CH$_2$CH$_2$CH=CH$_2$, —CH$_2$CH=CHCH$_3$, —CH=CH$_2$CH$_2$CH$_3$, —CH=CH$_2$CH=CH$_2$, and cyclobutenyl.

"Alkoxy", or "alkylthio", as used herein, refers to an alkyl group, as previously defined, attached to the principal carbon chain through an oxygen ("alkoxy") or sulfur ("alkylthio") atom.

"Methylene", "ethylene", and "propylene" as used herein refer to the bivalent moieties —CH$_2$—, —CH$_2$CH$_2$—, and —CH$_2$CH$_2$CH$_2$—, respectively.

"Ethenylene", "propenylene", and "butenylene" as used herein refer to the bivalent moieties —CH=CH—, —CH=CHCH$_2$—, —CH=CHCH$_2$CH$_2$—, —CH$_2$CH=CH$_2$CH$_2$—, and —CH$_2$CH$_2$CH=CH—, where each ethenylene, propenylene, and butenylene group can be in the cis or trans configuration. In certain embodiments, an ethenylene, propenylene, or butenylene group can be in the trans configuration.

"Alkylidene" refers to a bivalent hydrocarbon group formed by mono or dialkyl substitution of methylene. In certain embodiments, an alkylidene group has 1-6 carbon atoms. In other embodiments, an alkylidene group has 2-6, 1-5, 2-4, or 1-3 carbon atoms. Such groups include propylidene (CH$_3$CH$_2$CH=), ethylidene (CH$_3$CH=), and isopropylidene (CH$_3$(CH$_3$)CH=), and the like.

"Alkenylidene" refers to a bivalent hydrocarbon group having one or more double bonds formed by mono or dialkenyl substitution of methylene. In certain embodiments, an alkenylidene group has 2-6 carbon atoms. In other embodiments, an alkenylidene group has 2-6, 2-5, 2-4, or 2-3 carbon atoms. According to one aspect, an alkenylidene has two double bonds. Exemplary alkenylidene groups include CH$_2$=CHCH=, CH$_2$=CHCH$_2$CH=, and CH$_2$=CHCH$_2$CH=CHCH=.

"C$_{1-6}$ alkyl ester or amide" refers to a C$_{1-6}$ alkyl ester or a C$_{1-6}$ alkyl amide where each C$_{1-6}$ alkyl group is as defined above. Such C$_{1-6}$ alkyl ester groups are of the formula (C$_{1-6}$ alkyl)OC(=O)— or (C$_{1-6}$ alkyl)C(=O)O—. Such C$_{1-6}$ alkyl amide groups are of the formula (C$_{1-6}$ alkyl)NHC(=O)— or (C$_{1-6}$ alkyl)C(=O)NH—.

"C$_{2-6}$ alkenyl ester or amide" refers to a C$_{2-6}$ alkenyl ester or a C$_{2-6}$ alkenyl amide where each C$_{2-6}$ alkenyl group is as defined above. Such C$_{2-6}$ alkenyl ester groups are of the formula (C$_{2-6}$ alkenyl)OC(=O)— or (C$_{2-6}$ alkenyl)C(=O)O—. Such C$_{2-6}$ alkenyl amide groups are of the formula (C$_{2-6}$ alkenyl)NHC(=O)— or (C$_{2-6}$ alkenyl)C(=O)NH—.

""Fluoromethyl" as used herein refers to a methyl group substituted with one or more fluoro atoms (e.g., monofluoromethyl, difluoromethyl, trifluoromethyl).

"Fluoromethoxy" as used herein, refers to an fluoromethyl group, as previously defined, attached to the principal carbon chain through an oxygen atom.

"Treatment," "treat," and "treating" refer to reversing, alleviating, delaying the onset of, inhibiting the progress of, or preventing a disease or disorder as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

"Patient" or "subject", as used herein, means an animal subject, preferably a mammalian subject (e.g., dog, cat, horse, cow, sheep, goat, monkey, etc.), and particularly human subjects (including both male and female subjects, and including neonatal, infant, juvenile, adolescent, adult and geriatric subjects).

"Pharmaceutically acceptable carrier" as used herein refers to a nontoxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, cyclodextrins, sodium carboxymethylcellulose, polyacrylates, waxes, polyethylene-polyoxypropylene-block polymers, polyethylene glycol and wool fat.

"Pharmaceutically acceptable salt" refers to an acid or base salt of a compound of the invention, which salt possesses the desired pharmacological activity and is neither biologically nor otherwise undesirable. The salt can be formed with acids that include without limitation acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. Examples of a base salt include without limitation ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. In some embodiments, the basic nitrogen-containing groups can be quarternized with agents including lower alkyl halides such as methyl, ethyl, propyl and butyl chlorides, bromides and iodides; diallyl sulfates such as dimethyl, diethyl, dibutyl and diamyl sulfates; long chain halides such as decyl, lauryl, myristyl and stearyl chlorides, bromides and iodides; and aralkyl halides such as phenethyl bromides.

Unless indicated otherwise, nomenclature used to describe chemical groups or moieties as used herein follow the convention where, reading the name from left to right, the point of attachment to the rest of the molecule is at the right-hand side of the name. For example, the group "$(C_{1-3}$ alkoxy$)C_{1-3}$ alkyl," is attached to the rest of the molecule at the alkyl end. Further examples include methoxyethyl, where the point of attachment is at the ethyl end, and methylamino, where the point of attachment is at the amine end.

Unless indicated otherwise, where a bivalent group is described by its chemical formula, including two terminal bond moieties indicated by "-," it will be understood that the attachment is read from left to right.

Unless otherwise stated, structures depicted herein are also meant to include all enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

B. Compounds

In one embodiment, the present invention provides a compound of Formula I:

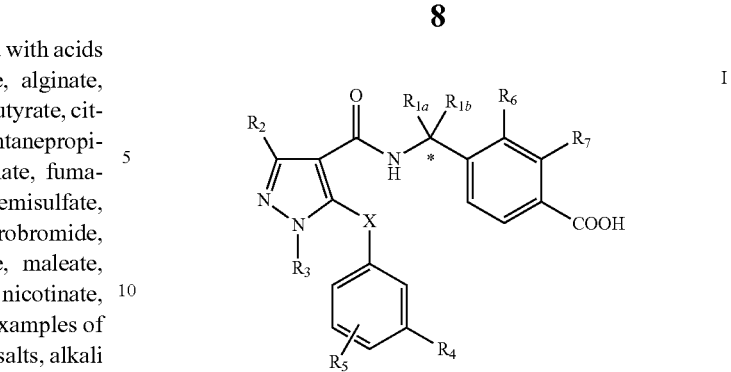

wherein:
one of $R_{1a}$ and $R_{1b}$ is hydrogen, and the other is methyl; or $R_{1a}$ and $R_{1b}$ are taken together to form a cyclopropyl ring;
$R_2$ is methyl or fluoromethyl (e.g., monofluoromethyl, difluoromethyl, trifluoromethyl);
$R_3$ is methyl;
$R_4$ is hydrogen, halo, fluoromethyl, methoxy, or fluoromethoxy (e.g., monofluoromethoxy, difluoromethoxy, trifluoromethoxy);
$R_5$ is hydrogen, halo, fluoromethyl, methoxy, or fluoromethoxy;
$R_6$ is hydrogen, halo, methyl, or methoxy;
$R_7$ is hydrogen, halo, methyl, or methoxy; and
X is oxygen;
or pharmaceutically acceptable salts thereof.

In some embodiments, one of $R_{1a}$ and $R_{1b}$ is hydrogen, and the other is methyl; $R_2$ is methyl, difluoromethyl, or trifluoromethyl; $R_3$ is methyl; $R_4$ is chloro, fluoro, trifluoromethyl, difluoromethyl, methyl, methoxy, difluoromethoxy, or trifluoromethoxy; and $R_5$ is hydrogen, chloro, fluoro, methyl, or methoxy.

In some embodiments, $R_5$ is hydrogen.

In some embodiments, $R_6$ and $R_7$ are both hydrogen.

In some embodiments, one of $R_{1a}$ and $R_{1b}$ is hydrogen, and the other is methyl, and $R_4$ is selected from chloro, trifluoromethyl, difluoromethyl, difluoromethoxy, and trifluoromethoxy.

In some embodiments, $R_{1a}$ and $R_{1b}$ are taken together to form a cyclopropyl ring; $R_2$ is methyl, trifluoromethyl, or difluoromethyl; $R_3$ is methyl; and $R_4$ is trifluoromethyl, difluoromethyl, chloro, or fluoro.

In some embodiments, one of $R_{1a}$ and $R_{1b}$ is hydrogen, and the other is methyl, and the compound of Formula I consists of a mixture of stereoisomers. In some embodiments, one of $R_{1a}$ and $R_{1b}$ is hydrogen, and the other is methyl, and the compound of Formula I consists of a substantially pure stereoisomer. In some embodiments, one of $R_{1a}$ and $R_{1b}$ is hydrogen, and the other is methyl, and the carbon of Formula I marked with a * has substantially the S-configuration. In some embodiments, one of $R_{1a}$ and $R_{1b}$ is hydrogen, and the other is methyl, and the carbon of Formula I marked with a * has substantially the R-configuration.

C. Pharmaceutical Formulations

Active compounds of the present invention can be combined with a pharmaceutically acceptable carrier to provide pharmaceutical formulations thereof. The particular choice of carrier and formulation will depend upon the particular route of administration for which the composition is intended.

The compositions of the present invention may be suitable for oral, parenteral, inhalation spray, topical, rectal, nasal, buccal, vaginal or implanted reservoir administration, etc. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

D. Subjects and Methods of Use

Prostaglandins have been shown to modulate various phases of the immune response. The lipid mediator prostaglandin E2 (PGE2) is an eicasanoid that is well known to suppress $CD4^+$ T cell activation through elevation of intracellular cAMP and inactivation of Ick. PGE2 has been also shown to play a role in regulating Th1 responses by suppression of interferon gamma (IFN-gamma) production and T cell proliferation. However PGE2 stimulation via the EP4 subtype of PGE2 receptor can also have the opposite effect, namely to promote Th1 differentiation (Prostaglandin E receptor subtypes EP2 and EP4 promote differentiation and expansion of Th1 and Th17 lymphocytes through different signaling modules, *Nature Medicine,* 2009, in press) and IL-17 production in activated CD4+ cells (Prostaglandin E2 synergistically with interleukin-23 favors human Th17 expansion, *Blood,* 2008, 112, 3696-3703, Prostaglandin E2 regulates Th17 cell differentiation and function through cyclic AMP and EP2/EP4 receptor signaling, *J. Exp. Med.* 2009, 206, 535-548, Prostaglandin E2 enhances Th17 response via modulation of IL-17 and IFN-γ production by memory CD4+ T cells, *Eur. J. Immunol.* 2009, 39, 1301-1312). Consistent with this, antagonism of EP4 with either a novel selective EP4 antagonist or a PGE2-neutralizing antibody suppresses Th1 differentiation, Th17 expansion, as well as IL-23 secretion by activated dendritic cells. Induction of Th1 differentiation by PGE2 is mediated by PI3K signaling whereas stimulation of IL-17 production requires cAMP signaling. In addition, administration of an EP4 antagonist to DBA/1 or C57BL/6 mice suppressed innate and adaptive immune responses, and suppressed disease in collagen induced arthritis (CIA) and experimental autoimmune encephalomyelitis (EAE) models, indicating that PGE2/EP4 signaling is critically involved in these autoimmune pathologies. These results suggest that suppression of PGE2/EP4 signaling may have therapeutic value in modifying inflammatory autoimmune diseases such as rheumatoid arthritis and multiple sclerosis.

Active compounds of the present invention may be administered to patients or subjects to treat a variety of different condition, particularly patients or subjects afflicted with:

(a) rheumatoid arthritis (see, e.g., Targeting rheumatoid arthritis and joint inflammation in the mouse, J. Clin. Invest. 2002, 110, 651-658); Prostaglandin E2 exacerbates collagen-induced arthritis in mice through the inflammatory interleukin-23/interleukin-17 axis, Arthritis Rheum. 2007. 56:2608-2619);

(b) multiple sclerosis (see, e.g., Narumiya, S. In *The Prostanoid Receptors in Signaling Network of Chronic Inflammation—The Role of FP in Bleomycin-induced Pulmonary Fibrosis and The Role of EP4 in Experimental Autoimmune Encephalomyelitis in Mice*, Eicosanoids and Chronic Inflammation, Montana, February, 2008), Keystone Symposia, Montana, February, 2008; Prostaglandin E receptor subtypes EP2 and EP4 promote differentiation and expansion of Th1 and Th17 lymphocytes through different signaling modules, *Nature Medicine*, 2009, in press);

(c) systemic lupus erythematosus (see, e.g., T-bet regulates IgG class switching and pathogenic auto Ab production, *Proc. Natl. Acad. Sci. USA* 2002, 99, 5545-50; Imbalance of Th1/Th2 transcription factors in patients with lupus nephritis, *Rheumatology* (Oxford) 2006, 45, 951-7);

(d) type 1 diabetes (see, e.g., Identification of a novel type 1 diabetes susceptibility gene, T-bet, *Human Genetics* 2004, 111, 177-84; T-bet controls autoaggressive CD8 lymphocyte response in type I diabetes, *J. Exp. Med.* 2004, 199, 1153-62);

(e) psoriasis (see, e.g., A molecule solves psoriasis? Systemic therapies for psoriasis inducing interleukin 4 and Th2 responses, *J. Mol. Med.* 2003, 81, 471-80); The IL-23/Th17 axis in the immunopathogenesis of psoriasis, *J Invest Dermatol* 2009, doi:10.1038/jid.2009.59;

(9 atherosclerosis (see, e.g., T-bet deficiency reduces atherosclerosis and alters plaque antigen-specific immune responses, *Proc. Natl. Acad. Sci. USA* 2005, 102, 1596-601);

(g) Crohn's disease (see, e.g., IL-23/IL-17 immunity as a hallmark of Crohn's disease, *Inflamm Bowl Dis.* 2009, 14, 1175-1184, The proinflammatory effect of prostaglandin E2 in experimental inflammatory bowel disease is mediated through the IL-23-IL-17 axis, *J. Immunol.* 2007, 178, 8138-8147);

h) inflammatory pain (see, e.g., Prostaglandin E2 receptor EP4 contributes to inflammatory pain hypersensitivity, *J. Pharmacol. Exp. Ther.* 2006, 319, 1096-1103);

(i) neuropathic pain (see, e.g., Localisation and modulation of prostanoid receptors EP1 and EP4 in the rat chronic constriction injury model of neuropathic pain, *Eur. J. Pain* 2007, 11, 605-613);

(j) migraine-associated pain (see, e.g., BGC20-1531, a novel, potent, and selective EP4 receptor antagonist: a putative new treatment for migraine headache, Br. J. Pharmacol. 2009, 156, 316-327).

(k) Spondyloarthropathies (see, e.g., Nonsteroidal Antiinflammatory Drugs reduce radiographic progression in patients with ankylosing spondylitis, Arthritis Rhuem. 2005, 52, 1756-1765; Efficacy of celecoxib, a cyclooxygenase 2-specific inhibitor, in the treatment of ankylosing spondylitis: a six-week controlled study with comparison against placebo and against a conventional nonsteroidal antiinflammatory drug. Arthritis Rheum. 2001, 44, 180-185, Increased numbers of circulating polyfunctional Th17 memory cells in patients with seronegative spondylarthritides, Arthritis Rheum, 2008, 58, 2307-2317);

(l) Skin cancer (see, e.g., Chemoprevention of nonmelanoma skin cancer with Celecoxib: A randomized, double-blind, placebo-controlled trial, J Natl Cancer Inst, 2010, 102, 1-10);

(m) Breast cancer (see, e.g., Potential new drug targets against hormone-dependent breast cancer identified, Exp. Rev. Anticancer Ther. 2008, 8, 507-509; Antagonism of the prostaglandin E receptor EP4 inhibits metastasis and enhances NK function, Breast Cancer Res. Treat. 2009, 117, 235-242; Prostaglandin E receptor EP4 antagonism inhibits breast cancer metastasis, Cancer Res. 2006, 66, 2923-2927);

(n) Colorectal cancer (see, e.g., Increased EP4 receptor expression in colorectal cancer progession promotes cell growth and anchorage independence, Cancer Res. 2006, 66, 3106-3113);

(o) Prostate cancer (see, e.g., Identification of EP4 as a potential target for the treatment of castration-resistant prostate cancer using a novel xenograft model, Cancer Res. 2010, 70, 1606-1615).

(p) Kidney cancer (see, e.g., Prostaglandin E2 regulates renal cell carcinoma invasion through a EP4-Rap signal transduction pathway, J. Bio. Chem. Aug. 10, 2011 (epub)).

(q) Cervical cancer (see, e.g., COX-2 expression is correlated with VEGF-C, lymphangiogenesis and lymph node metastasis in human cervical cancer, *Microvasc Res.* 2011, 82,131-40).

(r) Ovarian cancer (see, e.g., Ovarian epithelial cancer: a role for PGE2 synthesis and signaling in malignant transformation and progression, Mol Cancer, 2006, 5, 62.)

(s) Endometrial cancer (see, e.g., Prostaglandin E2 induces proliferation of Glandular epithelial cells of human endometrium via extracellular regulated kinase 1/2-mediated patheway. J Clin Endocrinol & Metabol. 2003, 88, 4481-4487).

(t) Glioblastoma (see, e.g. Microsomal prostaglandin E synthase-1 regulates human glioma cell growth via prostaglandin $E_2$-dependent activation of type II protein kinase A. Mol. Cancer. Ther. 2006, 5, 1817-1826).

(u) Head and neck cancer (see, e.g. Expression of prostaglandin $E_2$ receptors in oral squamous cell carcinomas and growth inhibitory effects of a selective EP3 antagonist, ONO-AE3-240. Int. J. Oncology 2009, 34, 847-852).

(v) Medulloblastoma (see, e.g. Tumor-growth-promoting cyclooxygenase-2 prostaglandin E2 pathway provides medulloblastoma therapeutic targets. Neuro-Oncol. 2008, 661-674).

(w) Lung cancer (see, e.g. Tumor cyclooxygenase-2/prostaglandin E2-dependent promotion of FOXP3 expression and CD4+ CD25+T regulatory cell activities in lung cancer. Cancer Res. 2005, 65, 5211-5220).

(x) Urinary tract cancers (see, e.g. Pathological function of prostaglandin $E_2$ receptors in transitional cell carcinoma of the upper urinary tract. Virchows Archiv. 2006, 448, 822-829).

In addition, PGE2 has been implicated as an important consituent in the immunosuppressive environment created by many solid tumors: Inhibiting the inhibitors: evaluating agents targeting cancer immunosuppression. Expert Opinion in Biological Therapy. 2010. 10, 1019-35.EP4 receptor antagonism has been shown to reduce tumor metastasis: Host and direct antitumor effects and profound reduction in tumor metastasis with selective EP4 receptor antagonism. Cancer Res. 2006, 66, 9665-9672.

Active compounds may be administered to subjects by any suitable route, including orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The active compounds are administered to the subjects in a treatment effective, or therapeutically effective, amount. The amount of the compounds of the present invention that may be combined with the carrier materials to produce a composition in a single dosage form will vary depending upon the host treated, and the particular route of administration. Preferably, the compositions should be formulated so that a dosage of between 0, 01-100 mg/kg body weight/day of the inhibitor can be administered to a patient receiving these compositions. In certain embodiments, the compositions of the present invention provide a dosage of between 0.01 mg and 50 mg is provided. In other embodiments, a dosage of between 0.1 and 25 mg or between 5 mg and 40 mg is provided.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

In order that the invention described herein may be more fully understood, the following examples are set forth. It should be understood that these examples are for illustrative purposes only and are not to be construed as limiting this invention in any manner.

Examples 1-113

General

Microwave heating was done using Biotage Emrys Liberator or Initiator microwave. Column chromatography was carried out using Biotage SP4. Solvent removal was carried out using either a Büchii rotary evaporator or a Genevac centrifugal evaporator. Preparative LC/MS was conducted using a Waters autopurifier and 19×100 mm XTerra 5 micron MS C18 column under acidic mobile phase condition. NMR spectra were recorded using Varian 400 MHz spectrometer.

When the term "inerted" is used to describe a reactor (e.g., a reaction vessel, flask, glass reactor, and the like) it is meant that the air in the reactor has been replaced with an essentially moisture-free or dry, inert gas (such as nitrogen, argon, and the like).

General methods and experimentals for preparing compounds of the present invention are set forth below. In certain cases, a particular compound is described by way of example. However, it will be appreciated that in each case a series of compounds of the present invention were prepared in accordance with the schemes and experimentals described below. The following abbreviations are used herein:

DEFINITIONS

The following abbreviations have the indicated meanings:
HATU: N,N,N',N'-Tetramethyl-O-(7-azabenzotriazol-1-yl)uronium Hexafluorophosphate
COMU: (1-Cyano-2-ethoxy-2-oxoethylidenaminooxy)dimethylamino-morpholino-carbenium hexafluorophosphate
DPCI: N,N'-Diisopropylcarbodiimide
DIEA: N,N-diisopropylethylamine
TEA: triethylamine
DMAP: 4-Dimethylaminopyridine
DMF: N,N-dimethylformamide
NMP: N-methylpyrrolidine
THF: tetrahydrofuran
DCM: dichloromethane
TFA: trifluoroacetic acid Materials:

The following compounds are commercially available:
5-chloro-1,3-dimethyl-1H-pyrazole-4-carbaldehyde (Maybridge Chemical Co., Ltd.)
5-chloro-1-methyl-3-(trifluoromethyl)-1H-pyrazole-4-carbaldehyde (Maybridge Chemical Co., Ltd.)
5-(3-chlorophenoxy)-1-methyl-3-(trifluoromethyl)-1H-pyrazole-4-carboxylic acid (Bionet Research)
1,3-dimethyl-5-(3-(trifluoromethyl)phenoxy)-1H-pyrazole-4-carboxylic acid (Bionet Research)
1-methyl-3-(trifluoromethyl)-5-(3-(trifluoromethyl)phenoxy)-1H-pyrazole-4 carboxylic acid (Bionet Research)
5-(4-chlorophenoxy)-1,3-dimethyl-1H-pyrazole-4-carboxylic acid (Bionet Research)
Ethyl 4,4-difluoroacetoacetate (Matrix Scientific)
(S)-methyl 4-(1-aminoethyl)benzoate hydrochloride (NetChem, Inc)
4-(1-aminocyclopropyl)benzoic acid (Allweys LLC)
All phenols except for 3-difluoromethylphenol were commercially available.

Compounds of the invention were made according to the general synthetic scheme shown in Scheme I:

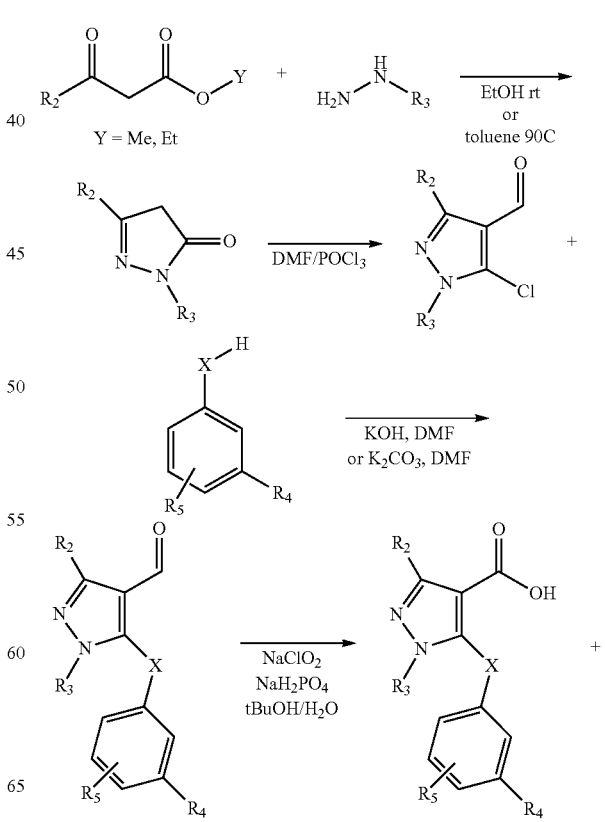

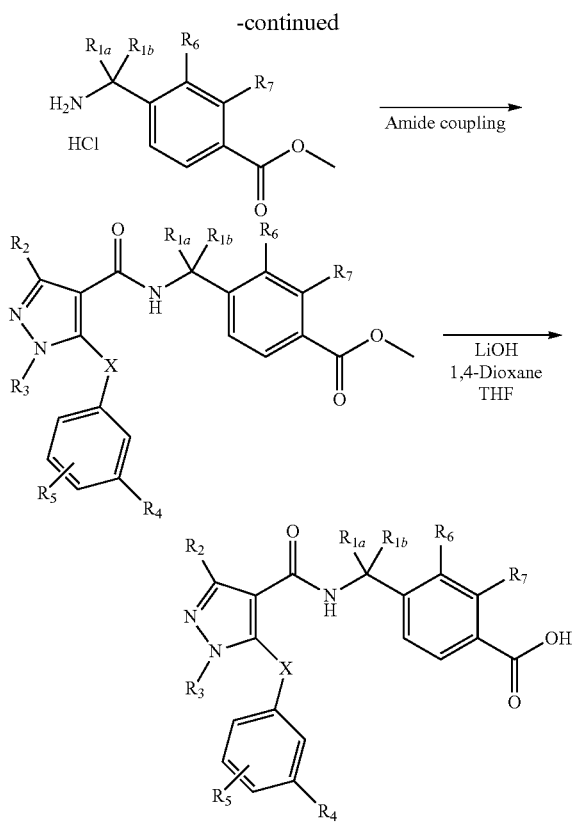

Preparation of representative non-limiting examples of the compounds of the invention are described below.

Examples 1-51

Production Scheme 1

Preparation procedure for 5-chloro-3-(difluoromethyl)-1-methyl-1H-pyrazole-4-carbaldehyde Step 1:

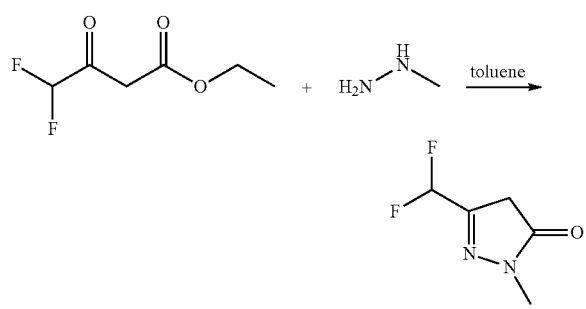

Ethyl 4,4-difluoroacetoacetate (30.12 g, 0.172 mol) was stirred in toluene (600 mL) over ice water. Solution of N-methylhydrazine (7.6 mL, 0.14 mol) in toluene (200 mL) was added slowly, dropwise over 20 min. The reaction mixture was heated at 100° C. for 2 hours. The reaction mixture evaporated to dryness. The resulting material was triturated with methyl t-butylether/heptane to give 3-(difluoromethyl)-1-methyl-1H-pyrazol-5(4H)-one in three batches (total 10.7 g, 51%) as orange powder. This material was used without further purification for the next reaction.

Step 2:

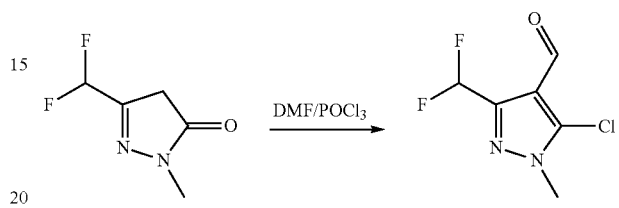

DMF (9.5 mL, 0.12 mol) was stirred over ice bath and phosphoryl chloride (24.0 mL, 0.257 mol) was added dropwise. To the solution was added 3-(difluoromethyl)-1-methyl-1H-pyrazol-5(4H)-one (5.51 g, 0.0372 mol) portion wise and the mixture was heated at 120° C. for 40 minutes. The reaction mixture was cooled, and the phosphoryl chloride was quenched by adding small chunks of ice slowly with stirring. The mixture was then extracted with ethyl acetate three times and combined organic layer was washed with water and brine, dried over MgSO4 and evaporated to give 5-chloro-3-(difluoromethyl)-1-methyl-1H-pyrazole-4-carbaldehyde (5.66 g, 78.2%) as a dark orange/brown solid. This material was used without further purification for the next reaction.

Production Scheme 2

Preparation procedure for 3-difluoromethylphenol

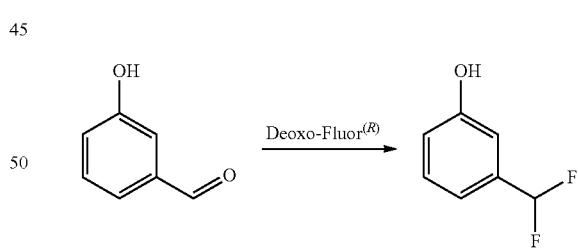

To a solution of 3-hydroxybenzaldehyde (1.01 g, 0.0083 mol) in methylene chloride (3.3 mL) was added a solution of bis(2-methoxyethyl)aminosulfur trifluoride (3.09 g, 0.0140 mol) in methylene chloride (3.3 mL) followed by ethanol (95.0 μL, 0.00163 mol). The reaction mixture was stirred at room temperature for 12 hours. The mixture was then quenched carefully adding saturated aqueous sodium bicarbonate solution. The organic layer separated, washed with brine, dried over MgSO4, and evaporated to give yellow oil. This oil was purified by column chromatography (0% to 50% ethyl acetate/heptane) to give the title compound (649 mg, 57%) as colorless oil.

Production Scheme 3

Exemplary Procedure for the preparation of 5-Aryloxy-pyrazole-4-carboxylic acid

Production Example 1

5-(3,4-dichlorophenoxy)-1,3-dimethyl-1H-pyrazole-4-carboxylic acid

Step 1:

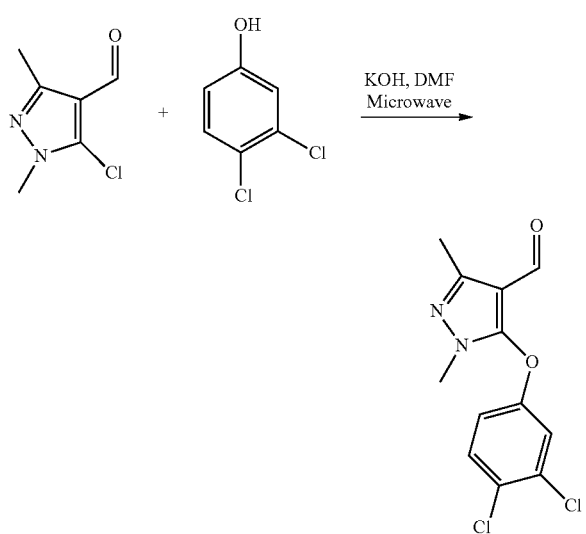

5-chloro-1,3-dimethyl-1H-pyrazole-4-carbaldehyde (500.0 mg, 0.00315 mol), 3,4-dichlorophenol (565 mg, 0.00344 mol) and potassium hydroxide (265 mg, 0.00472 mol) were stirred in DMF (2.0 mL). Mixture was heated at 150° C. for 20 min using microwave. Water was added and resulting mixture was extracted with ethyl acetate. Organic layer was washed with brine twice, dried over MgSO4 and evaporated. The resulting oil was purified by column chromatography (10% to 20% ethyl acetate/heptane) to give 5-(3,4-dichlorophenoxy)-1,3-dimethyl-1H-pyrazole-4-carbaldehyde (492 mg, 54.7%) as white solid.

Step 2:

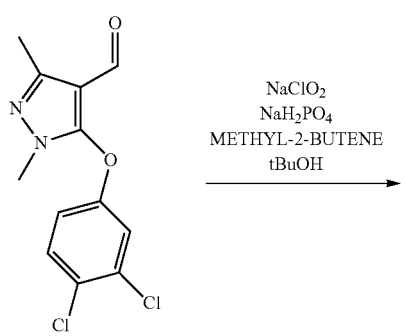

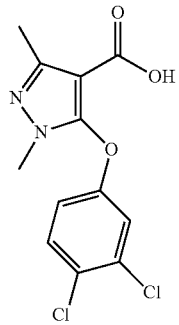

5-(3,4-dichlorophenoxy)-1,3-dimethyl-1H-pyrazole-4-carbaldehyde from Step 1 (492 mg, 0.001726 mol) and 2-methyl-2-butene (300 μL, 0.002832 mol) were stirred in tert-butyl alcohol (2.0 mL). A solution of sodium chlorite (400 mg, 0.003538 mol) and sodium dihydrogenphosphate (450 mg, 0.003751 mol) in water (3.0 mL) was added and reaction mixture was stirred for 12 hours at room temperature. Solvent was evaporated and resulting residue was dissolved in ethyl acetate. The organic layer was washed with water, dried over MgSO4 and evaporated to give the title compound (340 mg, 65.5%) as white solid. This material was used in the next step without further purification.

Production Example 2

5-(3-fluorophenoxy)-1,3-dimethyl-1H-pyrazole-4-carboxylic acid

The title compound was prepared using 5-chloro-1,3-dimethyl-1H-pyrazole-4-carbaldehyde and 3-fluorophenol in the manner similar to the method in Production Example 1 above.

Production Example 3

5-(3,4-difluorophenoxy)-1,3-dimethyl-1H-pyrazole-4-carboxylic acid

The title compound was prepared using 5-chloro-1,3-dimethyl-1H-pyrazole-4-carbaldehyde and 3,5-difluorophenol in the manner similar to the method in Production Example 1 above.

Production Example 4

5-(2,3-difluorophenoxy)-1,3-dimethyl-1H-pyrazole-4-carboxylic acid

The title compound was prepared using 5-chloro-1,3-dimethyl-1H-pyrazole-4-carbaldehyde and 2,3-difluorophenol in the manner similar to the method in Production Example 1 above.

Production Example 5

5-(2,5-difluorophenoxy)-1,3-dimethyl-1H-pyrazole-4-carboxylic acid

The title compound was prepared using 5-chloro-1,3-dimethyl-1H-pyrazole-4-carbaldehyde and 2,5-difluorophenol in the manner similar to the method in Production Example 1 above.

Production Example 6

5-(3,5-dichlorophenoxy)-1,3-dimethyl-1H-pyrazole-4-carboxylic acid

The title compound was prepared using 5-chloro-1,3-dimethyl-1H-pyrazole-4-carbaldehyde and 3,5-dichlorophenol in the manner similar to the method in Production Example 1 above.

Production Example 7

5-(3-chlorophenoxy)-1,3-dimethyl-1H-pyrazole-4-carboxylic acid

The title compound was prepared using 5-chloro-1,3-dimethyl-1H-pyrazole-4-carbaldehyde and 3-chlorophenol in the manner similar to the method in Production Example 1 above.

Production Example 8

5-(2,3-dichlorophenoxy)-1,3-dimethyl-1H-pyrazole-4-carboxylic acid

The title compound was prepared using 5-chloro-1,3-dimethyl-1H-pyrazole-4-carbaldehyde and 2,3-dichlorophenol in the manner similar to the method in Production Example 1 above.

Production Example 9

5-(3-chloro-5-fluorophenoxy)-1,3-dimethyl-1H-pyrazole-4-carboxylic acid

The title compound was prepared using 5-chloro-1,3-dimethyl-1H-pyrazole-4-carbaldehyde and 3-chloro-5-fluorophenol in the manner similar to the method in Production Example 1 above.

Production Example 10

5-(2-chloro-5-fluorophenoxy)-1,3-dimethyl-1H-pyrazole-4-carboxylic acid

The title compound was prepared using 5-chloro-1,3-dimethyl-1H-pyrazole-4-carbaldehyde and 2-chloro-5-fluorophenol in the manner similar to the method in Production Example 1 above.

Production Example 11

1,3-dimethyl-5-(m-tolyloxy)-1H-pyrazole-4-carboxylic acid

The title compound was prepared using 5-chloro-1,3-dimethyl-1H-pyrazole-4-carbaldehyde and m-cresol in the manner similar to the method in Production Example 1 above.

Production Example 12

5-(3,5-dimethylphenoxy)-1,3-dimethyl-1H-pyrazole-4-carboxylic acid

The title compound was prepared using 5-chloro-1,3-dimethyl-1H-pyrazole-4-carbaldehyde and 3,5-dimethylphenol in the manner similar to the method in Production Example 1 above.

Production Example 13

5-(3,5-dimethoxyphenoxy)-1,3-dimethyl-1H-pyrazole-4-carboxylic acid

The title compound was prepared using 5-chloro-1,3-dimethyl-1H-pyrazole-4-carbaldehyde and 3,5-dimethoxyphenol in the manner similar to the method in Production Example 1 above.

Production Example 14

5-(3-chlorophenoxy)-3-(difluoromethyl)-1-methyl-1H-pyrazole-4-carboxylic acid

The title compound was prepared using 5-chloro-3-(difluoromethyl)-1-methyl-1H-pyrazole-4-carbaldehyde and 3-chlorophenol in the manner similar to the method in Production Example 1 above except potassium carbonate was used instead of potassium hydroxide.

Production Example 15

3-(difluoromethyl)-1-methyl-5-(3-(trifluoromethyl)phenoxy)-1H-pyrazole-4-carboxylic acid The title compound was prepared using 5-chloro-3-(difluoromethyl)-1-methyl-4H-pyrazole-4-carbaldehyde and 3-trifluoromethylphenol in the manner similar to the method in Production Example 1 above except potassium carbonate was used instead of potassium hydroxide.

Production Example 16

1,3-dimethyl-5-(3-(trifluoromethoxy)phenoxy)-1H-pyrazole-4-carboxylic acid

The title compound was prepared using 5-chloro-1,3-dimethyl-1H-pyrazole-4-carbaldehyde and 3-trifluoromethoxylphenol in the manner similar to the method in Production Example 1 above.

Production Example 17

5-(3-fluorophenoxy)-1-methyl-3-(trifluoromethyl)-1H-pyrazole-4-carboxylic acid

The title compound was prepared using 5-chloro-1-methyl-3-(trifluoromethyl)-1H-pyrazole-4-carbaldehyde and 3-fluorophenol in the manner similar to the method in Production Example 1 above except potassium carbonate was used instead of potassium hydroxide.

Production Example 18

5-(3,4-difluorophenoxy)-1-methyl-3-(trifluoromethyl)-1H-pyrazole-4-carboxylic acid The title compound was prepared using 5-chloro-1-methyl-3-(trifluoromethyl)-1H-pyrazole-4-carbaldehyde and 3,4-difluorophenol in the manner similar to the method in Produc-

Production Example 19

5-(3,4-dichlorophenoxy)-1-methyl-3-(trifluoromethyl)-1H-pyrazole-4-carboxylic acid The title compound was prepared using 5-chloro-1-methyl-3-(trifluoromethyl)-1H-pyrazole-4-carbaldehyde and 3,4-dichlorophenol in the manner similar to the method in Production Example 1 above except potassium carbonate was used instead of potassium hydroxide.

Production Example 20

5-(3-(difluoromethoxy)phenoxy)-1,3-dimethyl-1H-pyrazole-4-carboxylic acid

The title compound was prepared using 5-chloro-1,3-dimethyl-1H-pyrazole-4-carbaldehyde and 3-difluoromethoxyphenol in the manner similar to the method in Production Example 1 above.

Production Example 21

5-(3-(difluoromethoxy)phenoxy)-1-methyl-3-(trifluoromethyl)-1H-pyrazole-4-carboxylic acid The title compound was prepared using 5-chloro-1-methyl-3-(trifluoromethyl)-1H-pyrazole-4-carbaldehyde and 3-difluoromethoxyphenol in the manner similar to the method in Production Example 1 above except potassium carbonate was used instead of potassium hydroxide.

Production Example 22

5-(3-(difluoromethoxy)phenoxy)-3-(difluoromethyl)-1-methyl-1H-pyrazole-4-carboxylic acid The title compound was prepared using 5-chloro-3-(difluoromethyl)-1-methyl-1H-pyrazole-4-carbaldehyde and 3-difluoromethoxyphenol in the manner similar to the method in Production Example 1 above except potassium carbonate was used instead of potassium hydroxide.

Production Example 23

3-(difluoromethyl)-5-(3-(difluoromethyl)phenoxy)-1-methyl-1H-pyrazole-4-carboxylic acid The title compound was prepared using 5-chloro-3-(difluoromethyl)-1-methyl-1H-pyrazole-4-carbaldehyde and 3-difluoromethylphenol in the manner similar to the method in Production Example 1 above except potassium carbonate was used instead of potassium hydroxide.

Production Example 24

5-(3-(difluoromethyl)phenoxy)-1,3-dimethyl-1H-pyrazole-4-carboxylic acid

The title compound was prepared using 5-chloro-1,3-dimethyl-1H-pyrazole-4-carbaldehyde and 3-difluoromethylphenol in the manner similar to the method in Production Example 1 above.

Production Example 25

5-(3-(difluoromethyl)phenoxy)-1-methyl-3-(trifluoromethyl)-1H-pyrazole-4-carboxylic acid The title compound was prepared using 5-chloro-1-methyl-3-(trifluoromethyl)-1H-pyrazole-4-carbaldehyde and 3-difluoromethylphenol in the manner similar to the method in Production Example 1 above except potassium carbonate was used instead of potassium hydroxide.

Production Example 26

5-(3,4-dichlorophenoxy)-3-(difluoromethyl)-1-methyl-1H-pyrazole-4-carboxylic acid The title compound was prepared using 5-chloro-3-(difluoromethyl)-1-methyl-1H-pyrazole-4-carbaldehyde and 3,4-dichlorophenol in the manner similar to the method in Production Example 1 above except potassium carbonate was used instead of potassium hydroxide.

Production Example 27

5-(4-fluorophenoxy)-1,3-dimethyl-1H-pyrazole-4-carboxylic acid

The title compound was prepared using 5-chloro-1,3-dimethyl-1H-pyrazole-4-carbaldehyde and 4-fluorophenol in the manner similar to the method in Production Example 1 above.

Production Example 28

1,3-dimethyl-5-(4-(trifluoromethyl)phenoxy)-1H-pyrazole-4-carboxylic acid

The title compound was prepared using 5-chloro-1,3-dimethyl-1H-pyrazole-4-carbaldehyde and 4-(trifluoromethyl)phenol in the manner similar to the method in Production Example 1 above except cesium carbonate was used instead of potassium hydroxide.

Production Example 29

5-(2-chloro-4-fluorophenoxy)-1,3-dimethyl-1H-pyrazole-4-carboxylic acid

The title compound was prepared using 5-chloro-1,3-dimethyl-1H-pyrazole-4-carbaldehyde and 2-chloro-4-fluorophenol in the manner similar to the method in Production Example 1.

Production Example 30

1,3-dimethyl-5-(p-tolyloxy)-1H-pyrazole-4-carboxylic acid

The title compound was prepared using 5-chloro-1,3-dimethyl-1H-pyrazole-4-carbaldehyde and p-cresol in the manner similar to the method in Production Example 1 above.

Production Example 31

1-methyl-3-(trifluoromethyl)-5-(4-(trifluoromethyl)phenoxy)-1H-pyrazole-4-carboxylic acid The title compound was prepared using 5-chloro-1-methyl-3-(trifluoromethyl)-1H-pyrazole-4-carbaldehyde and 4-(trifluoromethyl)phenol in the manner similar to the method in Production Example 1 above except potassium carbonate was used instead of potassium hydroxide.

Production Example 32

3-(difluoromethyl)-1-methyl-5-(4-(trifluoromethyl)phenoxy)-1H-pyrazole-4-carboxylic acid The title compound was prepared using 5-chloro-3-(difluoromethyl)-1-methyl-1H-pyrazole-4-carbaldehyde and 4-(trifluoromethyl)phenol in the manner similar to the method in Production Example 1 above except potassium carbonate was used instead of potassium hydroxide.

Production Example 33

5-(4-chlorophenoxy)-1-methyl-3-(trifluoromethyl)-1H-pyrazole-4-carboxylic acid

The title compound was prepared using 5-chloro-1-methyl-3-(trifluoromethyl)-1H-pyrazole-4-carbaldehyde and 4-chlorophenol in the manner similar to the method in Production Example 1 above except potassium carbonate was used instead of potassium hydroxide.

Production Example 34

5-(4-chlorophenoxy)-3-(difluoromethyl)-1-methyl-1H-pyrazole-4-carboxylic acid

The title compound was prepared using 5-chloro-3-(difluoromethyl)-1-methyl-1H-pyrazole-4-carbaldehyde and 4-chlorophenol in the manner similar to the method in Production Example 1 above except potassium carbonate was used instead of potassium hydroxide.

Production Scheme 4

Exemplary Procedure for Amide Coupling and Ester Hydrolysis

Example 1

ER-885289

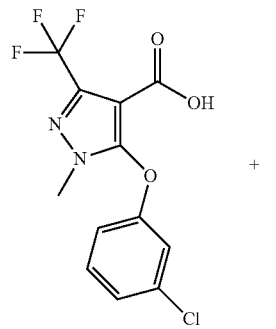

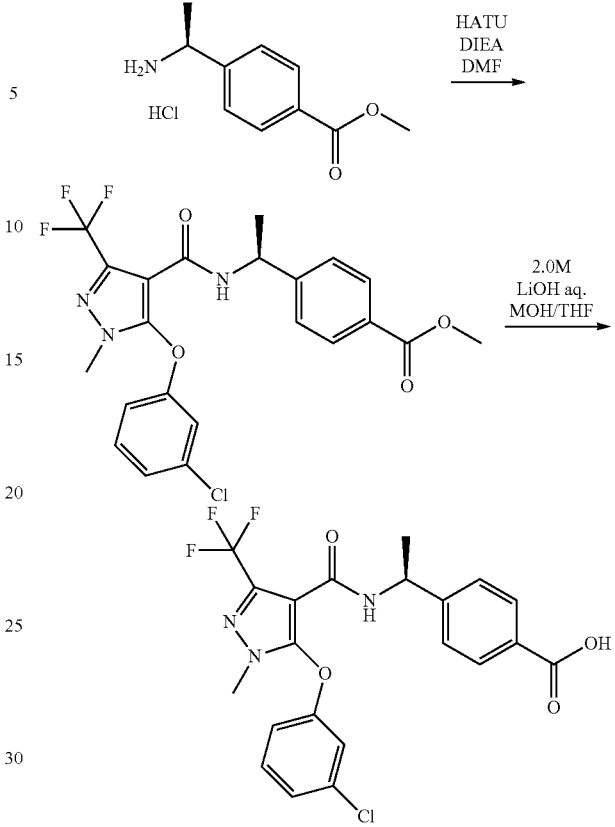

5-(3-chlorophenoxy)-1-methyl-3-(trifluoromethyl)-1H-pyrazole-4-carboxylic acid (50 mg, 0.0002 mol), HATU (65 mg, 0.00017 mol) and DIEA (30 µL, 0.00017 mol) were stirred in DMF (1.0 mL) for 20 min at rt. Solution of (S)-methyl 4-(1-aminoethyl)benzoate hydrochloride (40 mg, 0.00019 mol) and DIEA (32 µL, 0.00019 mol) in DMF (1.0 mL) was added dropwise and the reaction mixture was stirred at room temperature for 12 hours. Water was added and the resulting precipitate was collected, washed with water and dried under vacuum to give 59.2 mg of the methyl ester as white solid.

This methyl ester was dissolved in methanol (1.0 mL) and THF (1.0 mL). 2.0 M lithium hydroxide solution (240 µL) was added and the mixture was stirred at room temperature for 12 hours. The reaction mixture was neutralized with 1N hydrochloric acid solution (480 ul) and resulting emulsion was extracted with ethylacetate. The org. layer was separated and evaporated. The resulting material was dissolved in 3 mL of methanol and was purified by LC/MS (0.1% TFA acetonitrile/water mobile phase). The desired fractions were evaporated by Genevac to give the titled compound (27 mg, two steps 46%).

Example 2

ER-885290

Example 2 was prepared using 1,3-dimethyl-5-(3-(trifluoromethyl)phenoxy)-1H-pyrazole-4-carboxylic acid and (S)-methyl 4-(1-aminoethyl)benzoate hydrochloride in a manner similar to the Example 1 above.

Example 3

ER-885291

Example 3 was prepared using 1-methyl-3-(trifluoromethyl)-5-(3-(trifluoromethyl)phenoxy)-1H-pyrazole-4-carboxylic acid and (S)-methyl 4-(1-aminoethyl)benzoate hydrochloride in a manner similar to the Example 1 above.

Example 4

ER-885716

Example 4 was prepared using 5-(3,4-dichlorophenoxy)-1,3-dimethyl-1H-pyrazole-4-carboxylic acid and (S)-methyl 4-(1-aminoethyl)benzoate hydrochloride in a manner similar to the Example 1 above except hydrolysis was carried out in THF and 1,4-dioxane at 140° C. for 10 min using microwave and product was obtained as a solid after neutralization.

Example 5

ER-885717

Example 5 was prepared using 5-(3-fluorophenoxy)-4,3-dimethyl-1H-pyrazole-4-carboxylic acid and (S)-methyl 4-(1-aminoethyl)benzoate hydrochloride in a manner similar to the Example 4 above.

Example 6

ER-885718

Example 6 was prepared using 5-(3,4-difluorophenoxy)-1,3-dimethyl-1H-pyrazole-4-carboxylic acid and (S)-methyl 4-(1-aminoethyl)benzoate hydrochloride in a manner similar to the Example 4 above.

Example 7

ER-885719

Example 7 was prepared using 5-(2,3-difluorophenoxy)-1,3-dimethyl-1H-pyrazole-4-carboxylic acid and (S)-methyl 4-(1-aminoethyl)benzoate hydrochloride in a manner similar to the Example 4 above.

Example 8

ER-885720

Example 8 was prepared using 5-(2,5-difluorophenoxy)-1,3-dimethyl-1H-pyrazole-4-carboxylic acid and (S)-methyl 4-(1-aminoethyl)benzoate hydrochloride in a manner similar to the Example 4 above.

Example 9

ER-885721

Example 9 was prepared using 5-(3,5-dichlorophenoxy)-1,3-dimethyl-1H-pyrazole-4-carboxylic acid and (S)-methyl 4-(1-aminoethyl)benzoate hydrochloride in a manner similar to the Example 4 above.

Example 13

ER-885744

Example 13 was prepared using 5-(3-chlorophenoxy)-1,3-dimethyl-1H-pyrazole-4-carboxylic acid and (S)-methyl 4-(1-aminoethyl)benzoate hydrochloride in a manner similar to the Example 4 above.

Example 14

ER-886022

Example 14 was prepared using 5-(2,3-dichlorophenoxy)-1,3-dimethyl-1H-pyrazole-4-carboxylic acid and (S)-methyl 4-(1-aminoethyl)benzoate hydrochloride in a manner similar to the Example 4 above.

Example 15

ER-886024

Example 15 was prepared using 5-(3-chloro-5-fluorophenoxy)-1,3-dimethyl-1H-pyrazole-4-carboxylic acid and (S)-methyl 4-(1-aminoethyl)benzoate hydrochloride in a manner similar to the Example 4 above.

Example 16

ER-886025

Example 16 was prepared using 5-(2-chloro-5-fluorophenoxy)-1,3-dimethyl-1H-pyrazole-4-carboxylic acid and (S)-methyl 4-(1-aminoethyl)benzoate hydrochloride in a manner similar to the Example 4 above.

Example 17

ER-886032

Example 17 was prepared using 1,3-dimethyl-5-(m-tolyloxy)-1H-pyrazole-4-carboxylic acid and (S)-methyl 4-(1-aminoethyl)benzoate hydrochloride in a manner similar to the Example 4 above.

Example 18

ER-886033

Example 18 was prepared using 5-(3,5-dimethylphenoxy)-1,3-dimethyl-1H-pyrazole-4-carboxylic acid and (S)-methyl 4-(1-aminoethyl)benzoate hydrochloride in a manner similar to the Example 4 above.

Example 19

ER-886035

Example 19 was prepared using 5-(3,5-dimethoxyphenoxy)-1,3-dimethyl-1H-pyrazole-4-carboxylic acid and (S)-methyl 4-(1-aminoethyl)benzoate hydrochloride in a manner similar to the Example 4 above.

Example 20

ER-886045

Example 20 was prepared using 5-(3-chlorophenoxy)-3-(difluoromethyl)-1-methyl-1H-pyrazole-4-carboxylic acid and (S)-methyl 4-(1-aminoethyl)benzoate hydrochloride in a manner similar to the Example 4 above.

Example 21

ER-886046

Example 21 was prepared using 3-(difluoromethyl)-1-methyl-5-(3-(trifluoromethyl)phenoxy)-1H-pyrazole-4-carboxylic acid and (S)-methyl 4-(1-aminoethyl)benzoate hydrochloride in a manner similar to the Example 4 above.

Example 22

ER-886061

Example 22 was prepared using 1,3-dimethyl-5-(3-(trifluoromethoxy)phenoxy)-1H-pyrazole-4-carboxylic acid and (S)-methyl 4-(1-aminoethyl)benzoate hydrochloride in a manner similar to the Example 4 above.

Example 23

ER-886072

Example 23 was prepared using 5-(3-fluorophenoxy)-1-methyl-3-(trifluoromethyl)-1H-pyrazole-4-carboxylic acid and (S)-methyl 4-(1-aminoethyl)benzoate hydrochloride in a manner similar to the Example 1 above except COMU, TEA and NMP was used instead of HATU, DIEA and DMF, and the product was obtained as solid after neutralization.

Example 24

ER-886073

Example 24 was prepared using 5-(3,4-difluorophenoxy)-1-methyl-3-(trifluoromethyl)-1H-pyrazole-4-carboxylic acid and (S)-methyl 4-(1-aminoethyl)benzoate hydrochloride in a manner similar to the Example 23 above.

Example 25

ER-886074

Example 25 was prepared using 5-(3,4-dichlorophenoxy)-1-methyl-3-(trifluoromethyl)-1H-pyrazole-4-carboxylic acid and (S)-methyl 4-(1-aminoethyl)benzoate hydrochloride in a manner similar to the Example 23 above.

Example 26

ER-886077

Example 26 was prepared using 5-(3-chlorophenoxy)-1,3-dimethyl-1H-pyrazole-4-carboxylic acid and methyl 4-(1-aminocyclopropyl)benzoate hydrochloride in a manner similar to the Example 4 above.

Example 27

ER-886078

Example 27 was prepared using 3-(difluoromethyl)-1-methyl-5-(3-(trifluoromethyl)phenoxy)-1H-pyrazole-4-carboxylic acid and methyl 4-(1-aminocyclopropyl)benzoate hydrochloride in a manner similar to the Example 4 above.

Example 28

ER-886080

Example 28 was prepared using 5-(3-(difluoromethoxy)phenoxy)-1,3-dimethyl-1H-pyrazole-4-carboxylic acid and (S)-methyl 4-(1-aminoethyl)benzoate hydrochloride in a manner similar to the Example 23 above.

Example 29

ER-886082

Example 29 was prepared using 5-(3-(difluoromethoxy)phenoxy)-1-methyl-3-(trifluoromethyl)-1H-pyrazole-4-carboxylic acid and (S)-methyl 4-(1-aminoethyl)benzoate hydrochloride in a manner similar to the Example 23 above.

Example 30

ER-886083

Example 30 was prepared using 3-(difluoromethyl)-1-methyl-5-(3-(trifluoromethyl)phenoxy)-1H-pyrazole-4-carboxylic acid and (R)-methyl 4-(1-aminoethyl)benzoate hydrochloride in a manner similar to the Example 4 above.

Example 31

ER-886090

Example 31 was prepared using 5-(3-(difluoromethoxy)phenoxy)-3-(difluoromethyl)-1-methyl-1H-pyrazole-4-carboxylic acid and (S)-methyl 4-(1-aminoethyl)benzoate hydrochloride in a manner similar to the Example 23 above.

Example 32

ER-887480

Example 32 was prepared using 3-(difluoromethyl)-5-(3-(difluoromethyl)phenoxy)-1-methyl-1H-pyrazole-4-carboxylic acid and (S)-methyl 4-(1-aminoethyl)benzoate hydrochloride in a manner similar to the Example 4 above except product was obtained after LC/MS purification.

Example 33

ER-887495

Example 33 was prepared using 5-(3-(difluoromethyl)phenoxy)-1,3-dimethyl-1H-pyrazole-4-carboxylic acid and (S)-methyl 4-(1-aminoethyl)benzoate hydrochloride in a manner similar to the Example 4 above except HBTU, TEA and NMP was used instead of HATU, DIEA and DMF.

Example 34

ER-887995

Example 34 was prepared using 5-(3-(difluoromethyl)phenoxy)-1-methyl-3-(trifluoromethyl)-1H-pyrazole-4-carboxylic acid and (S)-methyl 4-(1-aminoethyl)benzoate

Example 35

ER-888024

Example 35 was prepared using 5-(3,4-dichlorophenoxy)-3-(difluoromethyl)-1-methyl-1H-pyrazole-4-carboxylic acid and (S)-methyl 4-(1-aminoethyl)benzoate hydrochloride in a manner similar to the Example 4 above.

Example 36

ER-888348

Example 36 was prepared using 5-(3,4-dichlorophenoxy)-3-(difluoromethyl)-1-methyl-1H-pyrazole-4-carboxylic acid and methyl 4-(1-aminocyclopropyl)benzoate hydrochloride in a manner similar to the Example 4 above.

Example 37

ER-888355

Example 37 was prepared using 5-(3-chlorophenoxy)-3-(difluoromethyl)-1-methyl-1H-pyrazole-4-carboxylic acid and methyl 4-(1-aminocyclopropyl)benzoate hydrochloride in a manner similar to the Example 4 above.

Example 38

ER-888363

5-(3,4-dichlorophenoxy)-1-methyl-3-(trifluoromethyl)-1H-pyrazole-4-carboxylic acid (104 mg, 0.0002929 mol), DMAP (17 mg, 0.000139 mol), PS-HOBT (1.00 mmol/g loading; 191 mg, 0.000191 mol), were stirred in 20% DMF in DCM (4:1, DCM:DMF, 5.00 mL). DPCI (140 uL, 0.0008941 mol) was added and the mixture was shaken at 40° C. 12 hours. The resin was then washed sequentially with DCM (3 ml), DMF (3 mL), DCM (3 ml), THF (3 ml), and then again with DCM (3 ml), and dried under vacuume. This resin was stirred in 20% DMF in DCM (4:1, DCM:DMF, 5.00 mL) and solution of methyl 4-(1-aminocyclopropyl)benzoate hydrochloride (27 mg, 0.000118 mol) in 20% DMF in DCM (5.00 mL) and DIEA (20 uL, 0.000115 mol) were added. The mixture was shaken at 40° C. for 12 hours. The resin was filtered and was washed with DCM. The combined filtrates were concentrated in vacuo to give a DMF solution. The solution was diluted with ethyl acetate washed with water and brine, dried over MgSO4 and evaporated to give a beige solid. The solid was purified by column chromatography (0 to 40%) to give methyl ester (18 mg) as a white solid. This methyl ester was dissolved in 1,4-dioxane (1.0 mL). 2.0 M lithium hydroxide solution (200 μL) was added and the mixture was heated at 60° C. for 12 hours. The reaction mixture was further heated at 140° C. for 20 min using microwave. The reaction mixture was acidified with 1N hydrochloric acid solution (420 ul) and water was added. The resulting precipitate was collected, washed with water and air dried to give the title compound (15.9 mg, two steps 26%) as white solid.

Example 39

ER-880663

Example 39 was prepared using 5-(4-chlorophenoxy)-1,3-dimethyl-1H-pyrazole-4-carboxylic acid and (S)-methyl 4-(1-aminoethyl)benzoate hydrochloride in a manner similar to the Example 4 above.

Example 40

ER-885302

Example 40 was prepared using 5-(4-fluorophenoxy)-1,3-dimethyl-1H-pyrazole-4-carboxylic acid and (S)-methyl 4-(1-aminoethyl)benzoate hydrochloride in a manner similar to the Example 4 above.

Example 41

ER-885311

Example 41 was prepared using 1,3-dimethyl-5-(4-(trifluoromethyl)phenoxy)-1H-pyrazole-4-carboxylic acid and (S)-methyl 4-(1-aminoethyl)benzoate hydrochloride in a manner similar to the Example 4 above.

Example 42

ER-886023

Example 42 was prepared using 5-(2-chloro-4-fluorophenoxy)-1,3-dimethyl-1H-pyrazole-4-carboxylic acid and (S)-methyl 4-(1-aminoethyl)benzoate hydrochloride in a manner similar to the Example 4 above.

Example 43

ER-885749

Example 43 was prepared using 1,3-dimethyl-5-(p-tolyloxy)-1H-pyrazole-4-carboxylic acid and (S)-methyl 4-(1-aminoethyl)benzoate hydrochloride in a manner similar to the Example 4 above.

Example 44

ER-888365

Example 44 was prepared using 1-methyl-3-(trifluoromethyl)-5-(4-(trifluoromethyl)phenoxy)-1H-pyrazole-4-carboxylic acid and (S)-methyl 4-(1-aminoethyl)benzoate hydrochloride in a manner similar to the Example 38.

Example 45

ER-888367

Example 45 was prepared using 3-(difluoromethyl)-1-methyl-5-(4-(trifluoromethyl)phenoxy)-1H-pyrazole-4-carboxylic acid and (S)-methyl 4-(1-aminoethyl)benzoate hydrochloride in a manner similar to the Example 38 above except hydrolysis was carried out at 60° C. for 12 hours.

Example 46

ER-888369

Example 46 was prepared using 5-(4-chlorophenoxy)-1-methyl-3-(trifluoromethyl)-1H-pyrazole-4-carboxylic acid and (S)-methyl 4-(1-aminoethyl)benzoate hydrochloride in a manner similar to the Example 38 above except the product was obtained after purification using heptane/ethyl acetate/formic acid as mobile phase.

Example 47

ER-888371

Example 47 was prepared using 5-(4-chlorophenoxy)-3-(difluoromethyl)-1-methyl-1H-pyrazole-4-carboxylic acid and (S)-methyl 4-(1-aminoethyl)benzoate hydrochloride in a manner similar to the Example 38 above.

Example 48

ER-888364

Example 48 was prepared using 1-methyl-3-(trifluoromethyl)-5-(4-(trifluoromethyl)phenoxy)-1H-pyrazole-4-carboxylic acid and methyl 4-(1-aminocyclopropyl)benzoate hydrochloride in a manner similar to the Example 38 above.

Example 49

ER-888366

Example 49 was prepared using 3-(difluoromethyl)-1-methyl-5-(4-(trifluoromethyl)phenoxy)-1H-pyrazole-4-carboxylic acid and methyl 4-(1-aminocyclopropyl)benzoate hydrochloride in a manner similar to the Example 38 above.

Example 50

ER-888368

Example 50 was prepared using 5-(4-chlorophenoxy)-1-methyl-3-(trifluoromethyl)-1H-pyrazole-4-carboxylic acid and methyl 4-(1-aminocyclopropyl)benzoate hydrochloride in a manner similar to the Example 38 above.

Example 51

ER-888370

Example 51 was prepared using 5-(4-chlorophenoxy)-3-(difluoromethyl)-1-methyl-1H-pyrazole-4-carboxylic acid and methyl 4-(1-aminocyclopropyl)benzoate hydrochloride in a manner similar to the Example 38 above.

Example 10

ER-885740

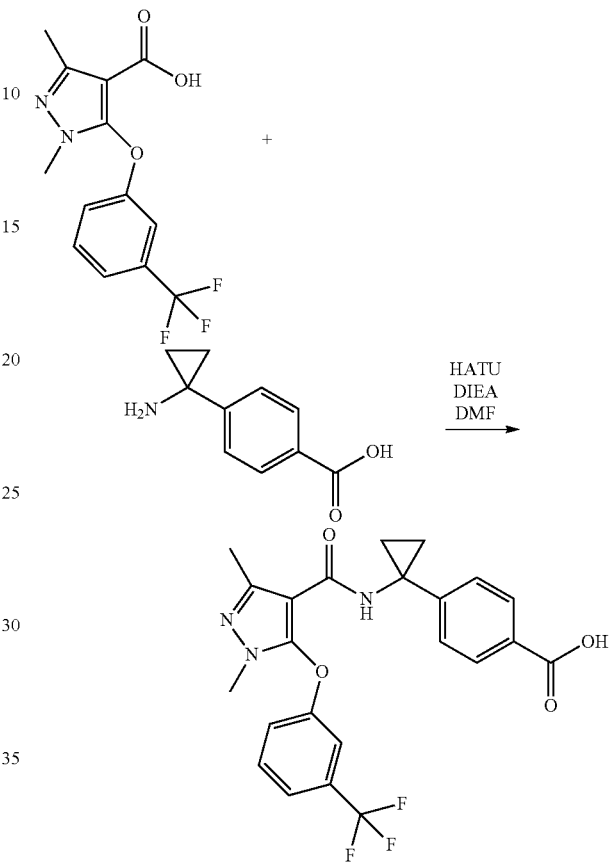

1,3-dimethyl-5-(3-(trifluoromethyl)phenoxy)-1H-pyrazole-4-carboxylic acid (20 mg, 0.00007 mol), HATU (28 mg, 0.000073 mol) and DIEA (13 µL, 0.000073 mol) were stirred in DMF (0.5 mL) for 20 min at rt. Solution of 4-(1-aminocyclopropyl)benzoic acid (14 mg, 0.000080 mol) and DIEA (14 µL, 0.000080 mol) in DMF (0.5 mL) was added dropwise and the reaction mixture was stirred at room temperature for 12 hours. The reaction mixture was diluted to 3 mL with methanol and purified by LC/MS (0.1% TFA Acetonitrile/water mobile phase). The desired fractions were evaporated by Genevac to give the title compound (15 mg, 50%).

Example 11

ER-885741

Example 11 was prepared using 1-methyl-3-(trifluoromethyl)-5-(3-(trifluoromethyl)phenoxy)-1H-pyrazole-4-carboxylic acid and 4-(1-aminocyclopropyl)benzoic acid in a manner similar to the Example 10 above.

Example 12

ER-885743

Example 12 was prepared using 5-(3-chlorophenoxy)-1-methyl-3-(trifluoromethyl)-1H-pyrazole-4-carboxylic acid and 1 4-(1-aminocyclopropyl)benzoic acid in a manner similar to the Example 10 above.

Preparation procedure for methyl 4-(1-aminocyclopropyl)benzoate hydrochloride Step 1:

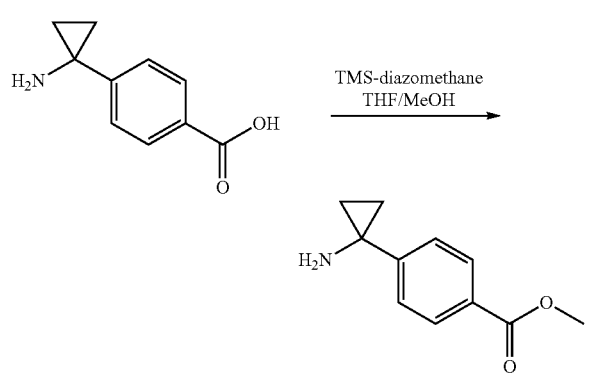

4-(1-aminocyclopropyl)benzoic acid (1.75 g, 0.00988 mol) was stirred in THF (20 mL) and Methanol (10 mL) over ice/water bath. 2.00 M of trimethylsilyldiazomethane in hexane (9.9 mL, 0.020 mol) was added and the mixture was stirred at room temperature for 12 hours. The reaction mixture was concentrated down to viscous oil which solidified upon standing to give a crystalline solid. Crude material was dried on high vacuum line for 12 hours to give methyl 4-(1-aminocyclopropyl)benzoate (1.65 g, 87%) as pale brown solid.

Step 2:

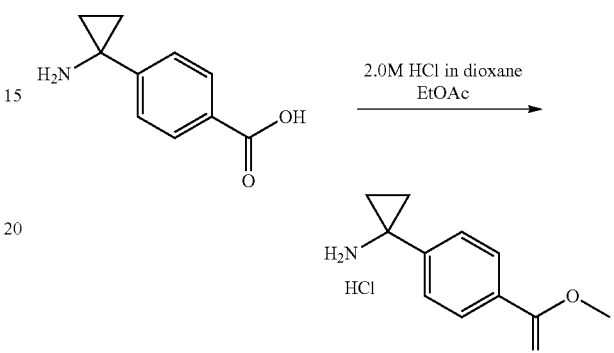

To a solution of ER-886774-00 (1.63 g, 0.0085 mol) in ethyl acetate (10 mL) was added 2.0 M of hydrogen chloride in Ether (6.0 mL, 0.012 mol). After stirring for several minutes, the reaction mixture was concentrated to give the title compound (quantitative yield) as pale brown solid.

TABLE 1

Analytical Data for Exemplary Compounds of Formula I

| Example | Structure | ER number | 1H NMR assignment |
|---|---|---|---|
| 1 | 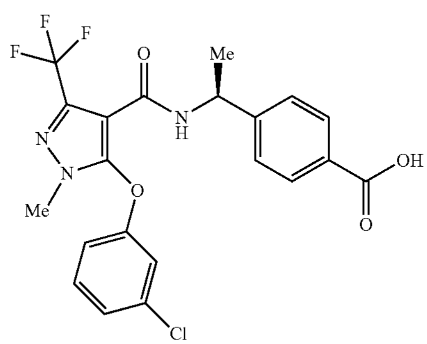 [SMILES: C[C@H](NC(=O)c1c(C(F)(F)F)nn(C)c1Oc1cccc(Cl)c1)c1ccc(C(=O)O)cc1] | ER-885289-00 | 1H NMR (400 MHz, CD3OD) δ ppm 8.56 (1H, d), 7.87 (2H, m), 7.30 (1H, m), 7.18 (2H, d), 7.08 (1H, t), 6.88 (1H, m), 4.96 (1H, m), 3.78 (3H, s), 1.34 (3H, d) |
| 2 | 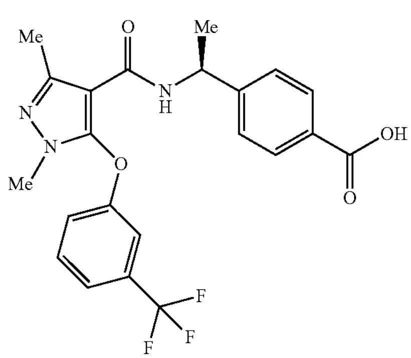 [SMILES: Cc1nn(C)c(Oc2cccc(C(F)(F)F)c2)c1C(=O)N[C@@H](C)c1ccc(C(=O)O)cc1] | ER-885290-00 | 1H NMR (400 MHz, CD3OD) δ ppm 7.88 (1H, d), 7.80 (2H, d), 7.49 (2H, m), 7.30 (1H, br. s.), 7.13 (2H, d), 4.99 (1H, m), 3.64 (3H, s), 2.37 (3H, m), 1.32 (3H, d) |

TABLE 1-continued

Analytical Data for Exemplary Compounds of Formula I

| Example | Structure | ER number | 1H NMR assignment |
|---|---|---|---|
| 3 | 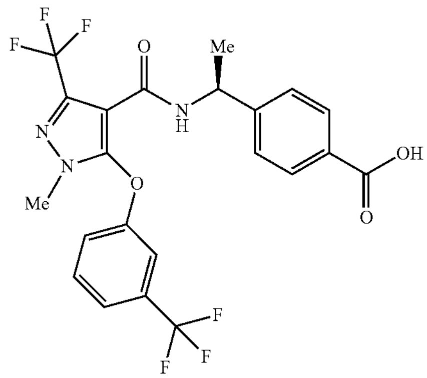 [SMILES: C[C@H](NC(=O)c1c(C(F)(F)F)nn(C)c1Oc1cccc(C(F)(F)F)c1)c1ccc(C(=O)O)cc1] | ER-885291-00 | 1H NMR (400 MHz, CD3OD) δ ppm 8.60 (1H, d), 7.81 (2H, d), 7.51 (2H, m), 7.39 (1H, s), 7.18 (3H, m), 4.92 (1H, m), 3.79 (3H, s), 1.30 (3H, d) |
| 4 | 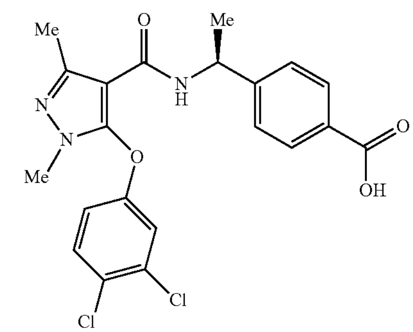 [SMILES: Cc1nn(C)c(Oc2ccc(Cl)c(Cl)c2)c1C(=O)N[C@@H](C)c1ccc(C(=O)O)cc1] | ER-885716-00 | 1H NMR (400 MHz, CD3OD) δ ppm 7.84 (2H, d), 7.42 (1H, d), 7.15 (2H, d), 7.13 (1H, d), 6.83 (1H, dd), 5.01 (1H, q), 3.62 (3H, s), 2.35 (3H, s), 1.36 (3H, d) |
| 5 | 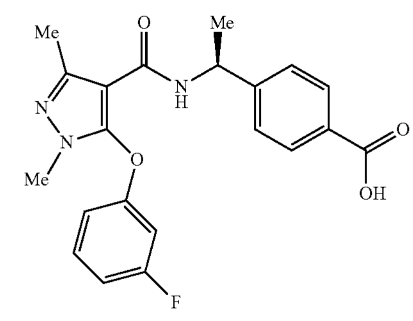 [SMILES: Cc1nn(C)c(Oc2cccc(F)c2)c1C(=O)N[C@@H](C)c1ccc(C(=O)O)cc1] | ER-885717-00 | 1H NMR (400 MHz, CD3OD) δ ppm 7.8 (3H, m), 7.34 (1H, m), 7.14 (2H, d), 6.91 (1H, m), 6.73 (2H, m), 5 (1H, q), 3.61 (3H, s), 2.35 (3H, s), 1.34 (3H, d) |
| 6 | 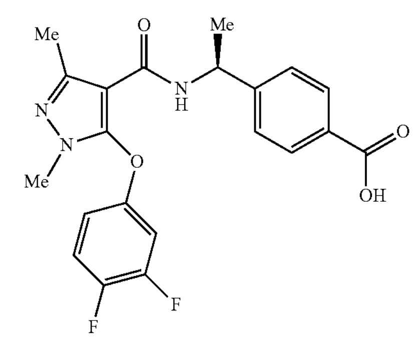 [SMILES: Cc1nn(C)c(Oc2ccc(F)c(F)c2)c1C(=O)N[C@@H](C)c1ccc(C(=O)O)cc1] | ER-885718-00 | 1H NMR (400 MHz, CD3OD) δ ppm 7.86 (3H, m), 7.19 (3H, m), 6.92 (1H, m), 6.68 (1H, m), 5.02 (1H, q), 3.61 (3H, s), 2.34 (3H, s), 1.37 (3H, d) |

TABLE 1-continued

Analytical Data for Exemplary Compounds of Formula I

| Example | Structure | ER number | 1H NMR assignment |
|---|---|---|---|
| 7 | 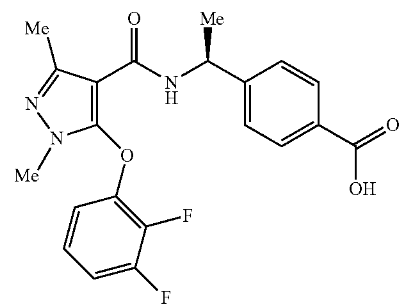 [SMILES: Cc1nn(C)c(Oc2cccc(F)c2F)c1C(=O)N[C@@H](C)c1ccc(C(=O)O)cc1] | ER-885719-00 | 1H NMR (400 MHz, CD3OD) δ ppm 8.01 (1H, d), 7.84 (2H, d), 7.19 (2H, d), 7.01 (2H, m), 6.58 (1H, m), 4.99 (1H, q), 3.66 (3H, s), 2.33 (3H, s), 1.37 (3H, d) |
| 8 | 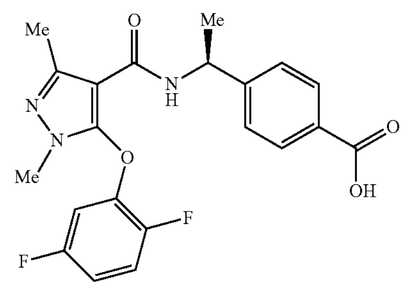 [SMILES: Cc1nn(C)c(Oc2cc(F)ccc2F)c1C(=O)N[C@@H](C)c1ccc(C(=O)O)cc1] | ER-885720-00 | 1H NMR (400 MHz, CD3OD) δ ppm 8.06 (1H, d), 7.85 (2H, d), 7.22 (3H, m), 6.87 (1H, m), 6.63 (1H, m), 5 (1H, q), 3.66 (3H, s), 2.32 (3H, s), 1.37 (3H, d) |
| 9 | 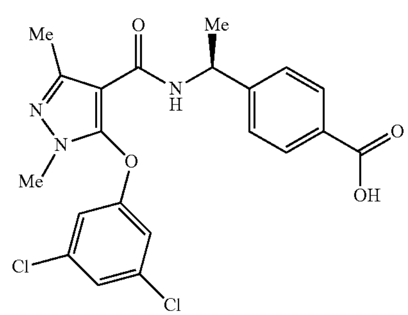 [SMILES: Cc1nn(C)c(Oc2cc(Cl)cc(Cl)c2)c1C(=O)N[C@@H](C)c1ccc(C(=O)O)cc1] | ER-885721-00 | 1H NMR (400 MHz, CD3OD) δ ppm 7.97 (1H, d), 7.85 (2H, d), 7.18 (3H, m), 6.89 (1H, d), 5.03 (1H, q), 3.62 (3H, s), 2.35 (3H, s), 1.38 (3H, d) |
| 10 | 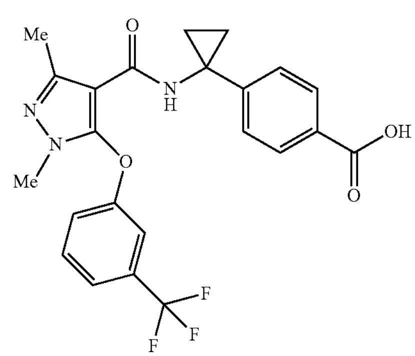 [SMILES: Cc1nn(C)c(Oc2cccc(C(F)(F)F)c2)c1C(=O)NC1(c2ccc(C(=O)O)cc2)CC1] | ER-885740-00 | 1H NMR (400 MHz, CD3OD) δ ppm 8.45 (1H, s), 7.79 (2H, d), 7.59 (1H, m), 7.52 (1H, m), 7.36 (1H, s), 7.21 (1H, dd), 7.03 (2H, d), 3.67 (3H, s), 2.38 (3H, s), 1.22 (2H, m), 0.91 (2H, m) |

TABLE 1-continued

Analytical Data for Exemplary Compounds of Formula I

| Example | Structure | ER number | 1H NMR assignment |
|---|---|---|---|
| 11 | 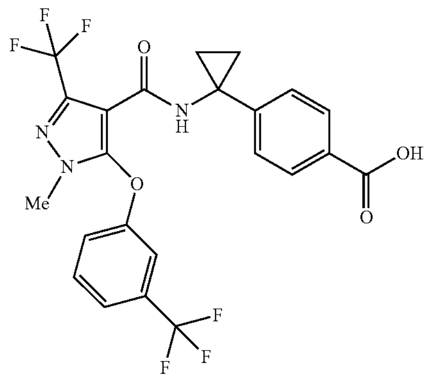 [SMILES: Cn1nc(C(F)(F)F)c(C(=O)NC2(c3ccc(C(=O)O)cc3)CC2)c1Oc1cccc(C(F)(F)F)c1] | ER-885741-00 | 1H NMR (400 MHz, CD3OD) δ ppm 9.03 (1H, s), 7.77 (2H, d), 7.58 (2H, m), 7.46 (1H, s), 7.26 (1H, d), 7.03 (2H, d), 3.83 (3H, s), 1.20 (2H, m), 0.84 (2H, m) |
| 12 | 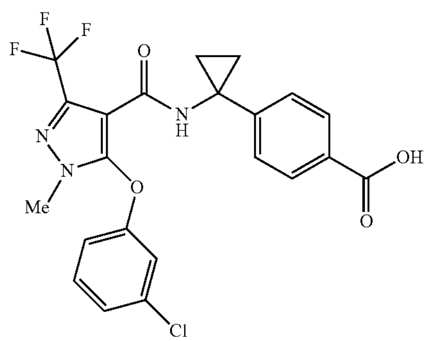 [SMILES: Cn1nc(C(F)(F)F)c(C(=O)NC2(c3ccc(C(=O)O)cc3)CC2)c1Oc1cccc(Cl)c1] | ER-885743-00 | 1H NMR (400 MHz, CD3OD) δ ppm 7.80 (2H, d), 7.39 (1H, m), 7.26 (1H, d), 7.17 (1H, t), 7.04 (2H, d), 6.97 (1H, dd), 3.82 (3H, s), 1.23 (2H, m), 0.92 (2H, m) |
| 13 | 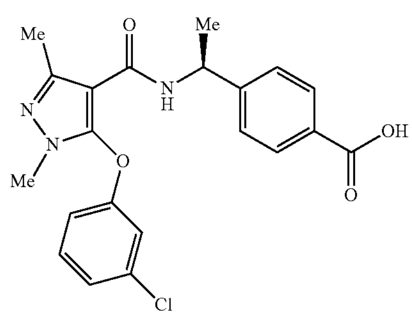 [SMILES: Cc1nn(C)c(Oc2cccc(Cl)c2)c1C(=O)N[C@@H](C)c1ccc(C(=O)O)cc1] | ER-885744-00 | 1H NMR (400 MHz, CD3OD) δ ppm 7.83 (2H, d), 7.32 (1H, m), 7.19 (1H, m), 7.14 (2H, d), 7.00 (1H, t), 6.85 (1H, dd), 5.01 (1H, m), 3.63 (3H, s), 2.36 (3H, s), 1.35 (3H, d) |
| 14 | 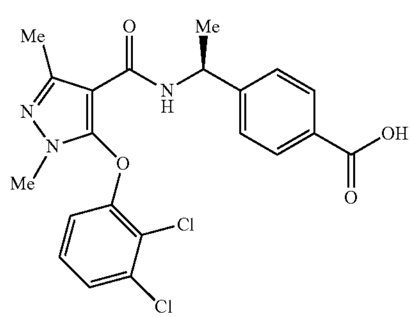 [SMILES: Cc1nn(C)c(Oc2cccc(Cl)c2Cl)c1C(=O)N[C@@H](C)c1ccc(C(=O)O)cc1] | ER-886022-00 | 1H NMR (400 MHz, CD3OD) δ ppm 7.81 (2H, d), 7.72 (1H, d), 7.31 (1H, d), 7.14 (3H, m), 6.64 (1H, d), 5 (1H, q), 3.63 (3H, s), 2.35 (3H, s), 1.37 (3H, d) |

TABLE 1-continued

Analytical Data for Exemplary Compounds of Formula I

| Example | Structure | ER number | 1H NMR assignment |
|---|---|---|---|
| 15 | 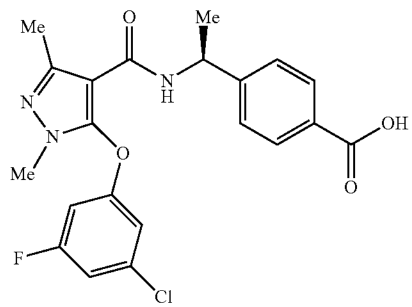 [SMILES: Cc1nn(C)c(Oc2cc(F)cc(Cl)c2)c1C(=O)N[C@@H](C)c1ccc(C(=O)O)cc1] | ER-886024-00 | 1H NMR (400 MHz, CD3OD) δ ppm 7.96 (1H, d), 7.85 (2H, d), 7.19 (2H, d), 6.98 (1H, dt), 6.79 (1H, m), 6.67 (1H, dt), 5.03 (1H, q), 3.62 (3H, s), 2.35 (3H, s), 1.38 (3H, d) |
| 16 | 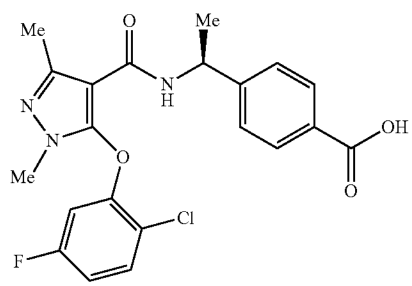 [SMILES: Cc1nn(C)c(Oc2cc(F)ccc2Cl)c1C(=O)N[C@@H](C)c1ccc(C(=O)O)cc1] | ER-886025-00 | 1H NMR (400 MHz, CD3OD) δ ppm 7.83 (3H, m), 7.49 (1H, dd), 7.18 (2H, m), 6.91 (1H, m), 6.53 (1H, dd), 5.01 (1H, q), 3.64 (3H, s), 2.34 (3H, s), 1.38 (3H, d) |
| 17 | 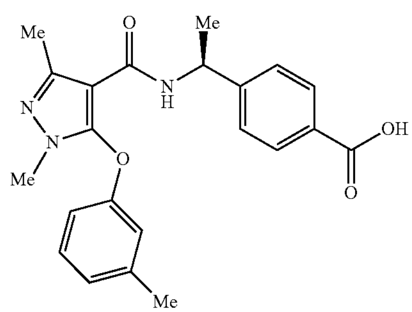 [SMILES: Cc1cccc(Oc2c(C(=O)N[C@@H](C)c3ccc(C(=O)O)cc3)c(C)nn2C)c1] | ER-886032-00 | 1H NMR (400 MHz, CD3OD) δ ppm 7.78 (2H,d), 7.53 (1H, d), 7.24 (1H, t), 7.07 (1H, m), 7.00 (1H, d), 6.72 (2H, m), 4.99 (1H, m), 3.59 (3H, s), 2.35 (3H, s), 2.29 (3H, s), 1.32 (3H, d) |
| 18 | 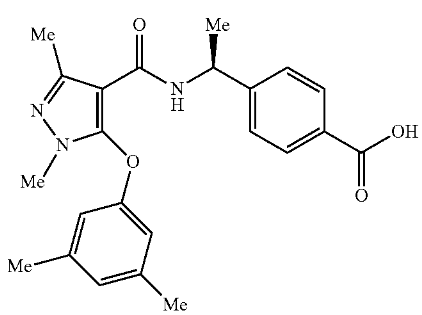 [SMILES: Cc1cc(C)cc(Oc2c(C(=O)N[C@@H](C)c3ccc(C(=O)O)cc3)c(C)nn2C)c1] | ER-886033-00 | 1H NMR (400 MHz, CD3OD) δ ppm 7.77 (2H, d), 7.47 (1H, d), 7.05 (2H, d), 6.83 (1H, s), 6.52 (2H, s), 5.00 (1H, m), 3.58 (3Hs), 2.35 (3H, s), 2.24 (3H, s), 1.33 (3H, d) |
| 19 | 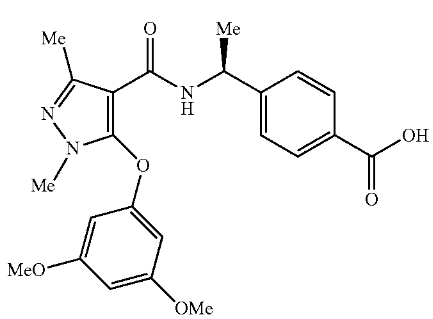 [SMILES: COc1cc(OC)cc(Oc2c(C(=O)N[C@@H](C)c3ccc(C(=O)O)cc3)c(C)nn2C)c1] | ER-886035-00 | 1H NMR (400 MHz, CD3OD) δ ppm 7.79 (2H, d), 7.11 (2H, d), 6.29 (1H, t), 6.04 (2H, d), 5.00 (1H, m), 3.71 (6H, s), 3.60 (3H, s), 2.35 (3H, s), 1.36 (3H, d) |

TABLE 1-continued

Analytical Data for Exemplary Compounds of Formula I

| Example | Structure | ER number | 1H NMR assignment |
|---|---|---|---|
| 20 | 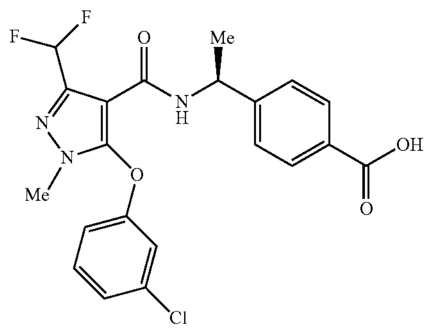 [SMILES: C[C@H](NC(=O)c1c(C(F)F)nn(C)c1Oc1cccc(Cl)c1)c1ccc(C(=O)O)cc1] | ER-886045-00 | 1H NMR (400 MHz, CD3OD) δ ppm 8.05 (1H, m), 7.84 (2H, d), 7.32 (1H, t), 7.20 (1H, m), 7.15 (2H, d), 6.96 (3H, m), 4.99 (1H, q), 3.75 (3H, s), 1.36 (3H, d) |
| 21 | 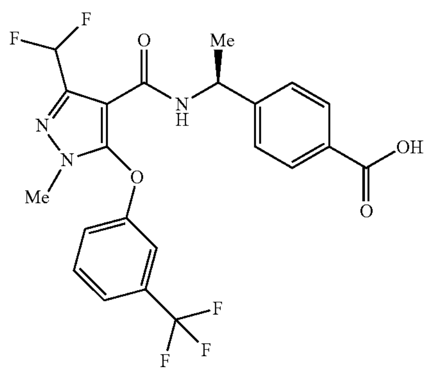 [SMILES: C[C@H](NC(=O)c1c(C(F)F)nn(C)c1Oc1cccc(C(F)(F)F)c1)c1ccc(C(=O)O)cc1] | ER-886046-00 | 1H NMR (400 MHz, CD3OD) δ ppm 8.11 (1H, m), 7.81 (2H, d), 7.52 (2H, m), 7.37 (1H, s), 7.15 (3H, m), 6.96 (1H, m), 4.97 (1H, q), 3.76 (3H, s), 1.32 (3H, d) |
| 22 | 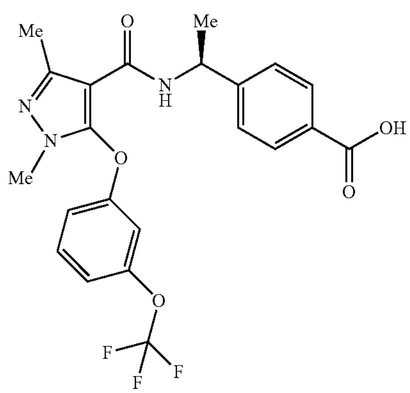 [SMILES: Cc1nn(C)c(Oc2cccc(OC(F)(F)F)c2)c1C(=O)N[C@@H](C)c1ccc(C(=O)O)cc1] | ER-886061-00 | 1H NMR (400 MHz, CD3OD) δ ppm 7.83 (3H, m), 7.43 (1H, t), 7.12 (3H, m), 6.95 (1H, s), 6.87 (1H, dd), 5.00 (1H, quin), 3.63 (3H, s), 2.36 (3H, s), 1.33 (3H, d) |
| 23 | 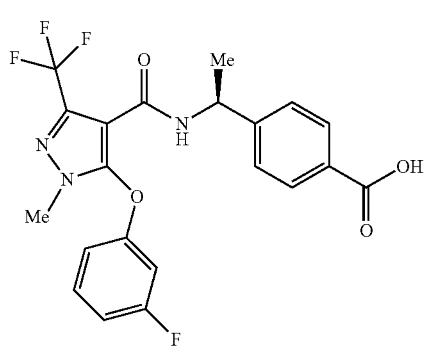 [SMILES: C[C@H](NC(=O)c1c(C(F)(F)F)nn(C)c1Oc1cccc(F)c1)c1ccc(C(=O)O)cc1] | ER-886072-00 | 1H NMR (400 MHz, CD3OD) δ ppm 8.56 (1H, d), 7.82 (2H, d), 7.33 (1H, m), 7.18 (2H, d), 6.91 (1H, m), 6.79 (2H, m), 4.95 (1H, m), 3.77 (3H, s), 1.34 (3H, d) |

TABLE 1-continued

Analytical Data for Exemplary Compounds of Formula I

| Example | Structure | ER number | 1H NMR assignment |
|---|---|---|---|
| 24 | 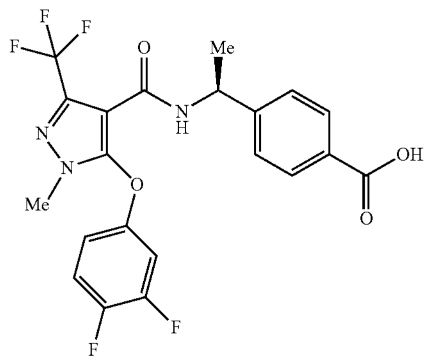 | ER-886073-00 | 1H NMR (400 MHz, CD3OD) δ ppm 8.60 (1H, d), 7.86 (2H, d), 7.19 (3H, m), 6.99 (1H, m), 6.75 (1H, m), 4.97 (1H, m), 3.77 (3H, s), 1.35 (3H, d) |
| 25 | 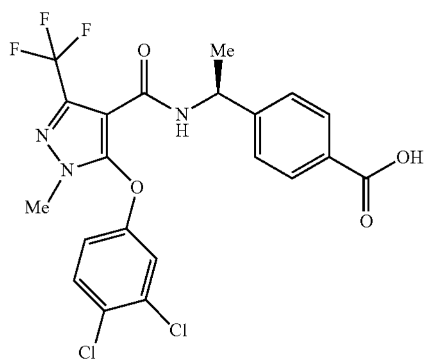 | ER-886074-00 | 1H NMR (400 MHz, CD3OD) δ ppm 8.61 (1H, d), 7.86 (2H, d), 7.40 (1H, d), 7.22 (1H, d), 7.18 (2H, d), 6.91 (1H, m), 6.89 (1H, dd), 4.96 (1H, m), 3.78 (3H, s), 1.35 (3H, d) |
| 26 | 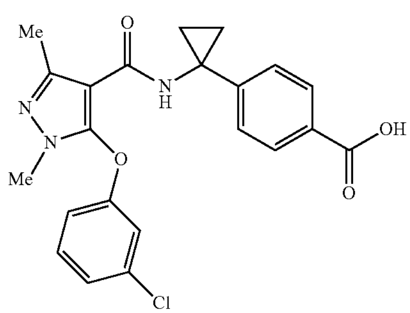 [SMILES: Cc1nn(C)c(Oc2cccc(Cl)c2)c1C(=O)NC1(c2ccc(C(=O)O)cc2)CC1] | ER-886077-00 | 1H NMR (400 MHz, CD3OD) δ ppm 8.40 (1H, s), 7.81 (2H, d), 7.38 (1H, t), 7.24 (1H, m), 7.06 (3H, m), 6.92 (1H, dd), 3.66 (3H, s), 2.37 (3H, s), 1.24 (2H, m), 0.98 (2H, m) |
| 27 | 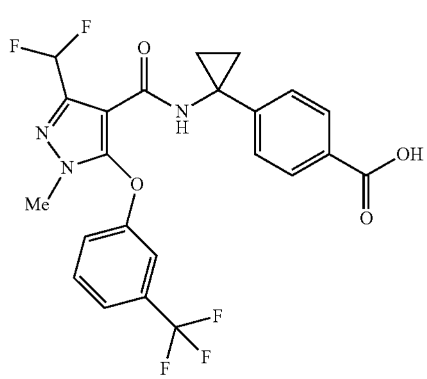 [SMILES: Cn1nc(C(F)F)c(C(=O)NC2(c3ccc(C(=O)O)cc3)CC2)c1Oc1cccc(C(F)(F)F)c1] | ER-886078-00 | 1H NMR (400 MHz, CD3OD) δ ppm 7.78 (2H, d), 7.59 (2H, m), 7.44 (1H, s), 7.24 (1H, m), 7.00 (3H, m), 3.80 (3H, s), 1.21 (2H, m), 0.89 (2H, m) |

TABLE 1-continued

Analytical Data for Exemplary Compounds of Formula I

| Example | Structure | ER number | 1H NMR assignment |
|---|---|---|---|
| 28 | 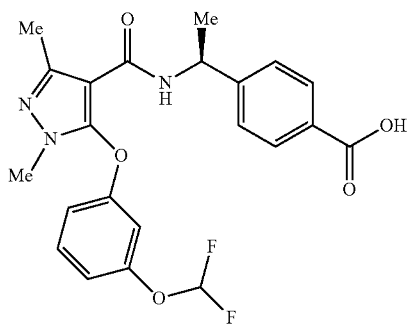 [SMILES: Cc1nn(C)c(Oc2cccc(OC(F)F)c2)c1C(=O)N[C@@H](C)c1ccc(C(=O)O)cc1] | ER-886080-00 | 1H NMR (400 MHz, CD3OD) δ ppm 7.81 (2H, d), 7.77 (1H, d), 7.35 (1H, t), 7.14 (2H, d), 6.95 (1H, m), 6.80 (1H, t), 6.78 (1H, m), 6.73 (1H, m), 5.00 (1H, m), 3.61 (3H, s), 2.35 (3H, s), 1.33 (3H, s) |
| 29 | 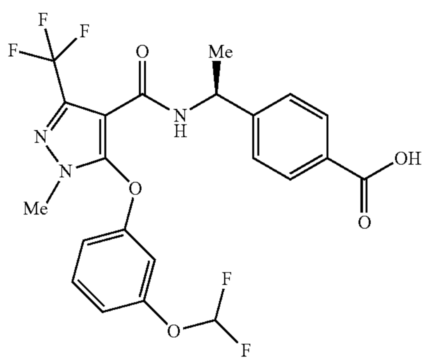 [SMILES: C[C@H](NC(=O)c1c(C(F)(F)F)nn(C)c1Oc1cccc(OC(F)F)c1)c1ccc(C(=O)O)cc1] | ER-886082-00 | 1H NMR (400 MHz, CD3OD) δ ppm 8.55 (1H, d), 7.82 (2H, d), 7.34 (1H, t), 7.17 (2H, d), 6.95 (1H, m), 6.83 (1H, t), 6.80 (1H, t), 6.78 (2H, dd), 4.94 (1H, m), 3.76 (3H, s), 3.65 (3H, s), 1.32 (3H, s) |
| 30 | 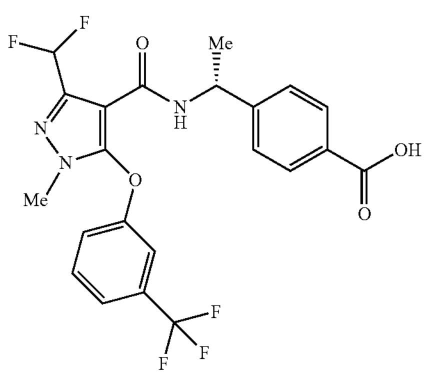 [SMILES: C[C@@H](NC(=O)c1c(C(F)F)nn(C)c1Oc1cccc(C(F)(F)F)c1)c1ccc(C(=O)O)cc1] | ER-886083-00 | 1H NMR (400 MHz, CD3OD) δ ppm 8.10 (1H, d), 7.81 (2H, d), 7.52 (2H, m), 7.37 (1H, m), 7.08 (4H, m), 4.97 (1H, q), 3.76 (3H, s), 1.32 (3H, d) |
| 31 | 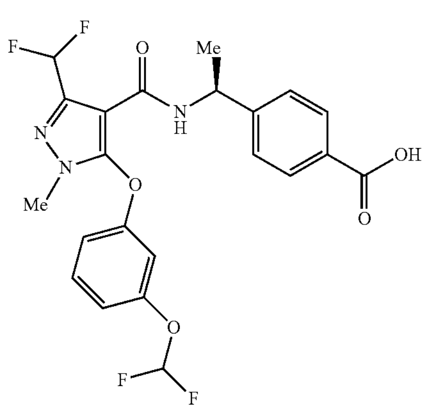 [SMILES: C[C@H](NC(=O)c1c(C(F)F)nn(C)c1Oc1cccc(OC(F)F)c1)c1ccc(C(=O)O)cc1] | ER-886090-00 | 1H NMR (400 MHz, CD3OD) δ ppm 8.02 (1H, d), 7.81 (2H, d), 7.36 (1H, t), 7.15 (2H, d), 6.98 (1H, m), 6.83 (1H, m), 6.81 (1H, t), 6.76 (2H, dd), 4.99 (1H, m), 3.73 (3H, s), 1.34 (3H, s) |

TABLE 1-continued

Analytical Data for Exemplary Compounds of Formula I

| Example | Structure | ER number | 1H NMR assignment |
|---|---|---|---|
| 32 | 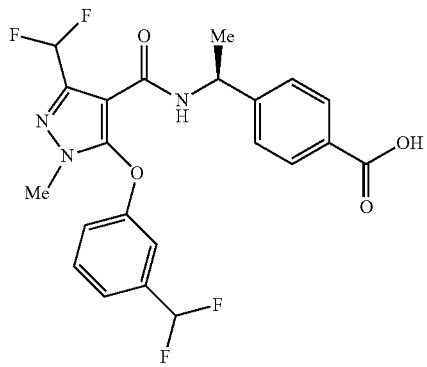 | ER-887480-00 | 1H NMR (400 MHz, CD3OD) δ ppm 8.01 (1H, d), 7.79 (2H, d), 7.46 (1H, t), 7.36 (1H, d), 7.19 (1H, s), 7.11 (2H, d), 7.06 (1H, m), 6.96 (1H, t), 6.73 (1H, t), 4.95 (1H, m), 3.74 (3H, s), 1.31 (3H, s) |
| 33 | 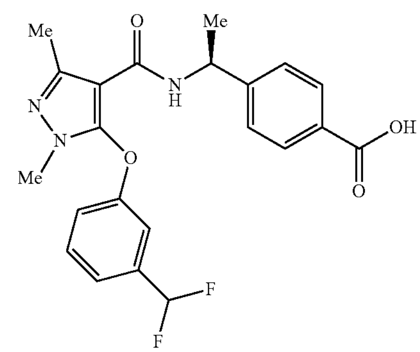 | ER-887495-00 | 1H NMR (400 MHz, CD3OD) δ ppm 7.77 (3H, m), 7.46 (1H, t), 7.34 (1H, d), 7.14 (1H, s), 7.10 (1H, d), 7.04 (1H, m), 6.73 (1H, t), 4.97 (1H, q), 3.62 (3H, s), 2.35 (3H, s), 1.31 (3H, d) |
| 34 | 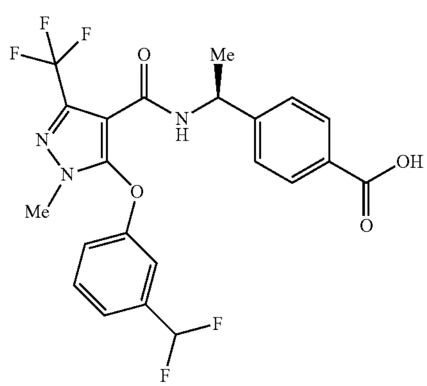 | ER-887995-00 | 1H NMR (400 MHz, CD3OD) δ ppm 8.53 (1H, d), 7.79 (2H, d), 7.43 (1H, t), 7.34 (1H, d), 7.20 (1H, s), 7.13 (2H, d), 7.06 (1H, m), 6.72 (1H, t), 4.91 (1H, m), 3.76 (3H, s), 1.28 (3H, d) |
| 35 | 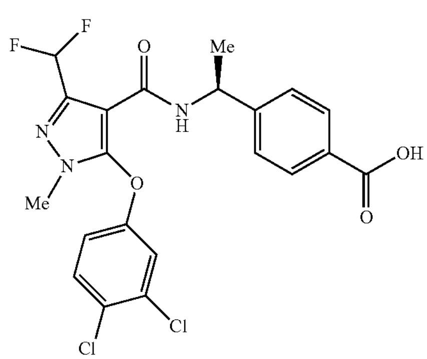 | ER-888024-00 | 1H NMR (400 MHz, CD3OD) δ ppm 8.12 (1H, d), 7.86 (2 H, d), 7.44 (1 H, d), 7.17 (5 H, d), 5.00 (1 H, q), 3.76 (3 H, s), 1.38 (3 H, d) |

TABLE 1-continued

Analytical Data for Exemplary Compounds of Formula I

| Example | Structure | ER number | 1H NMR assignment |
|---|---|---|---|
| 36 | 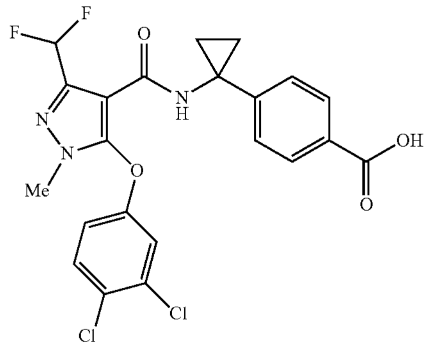 | ER-888348-00 | 1H NMR (400 MHz, CD3OD) δ ppm 8.65 (1H, s), 7.81 (2H, d), 7.52 (1H, d), 7.30 (1H, d), 7.03 (2H, d), 6.97 (1H, m), 6.91 (1H, t), 3.77 (3H, s), 1.24 (2H, dd), 0.99 (2H, dd) |
| 37 | 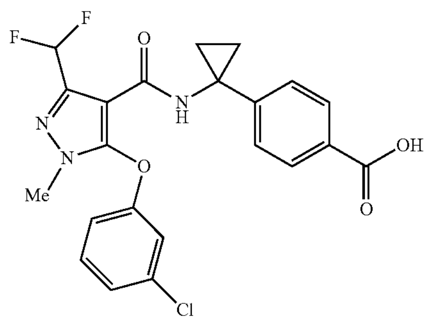 [SMILES: Cn1nc(C(F)F)c(C(=O)NC2(c3ccc(C(=O)O)cc3)CC2)c1Oc1cccc(Cl)c1] | ER-888355-00 | 1H NMR (400 MHz, CD3OD) δ ppm 8.63 (1H, s), 7.79 (2H, d), 7.38 (1H, t), 7.25 (1H, m), 7.14 (1H, t), 7.03 (2H, d), 6.95 (1H, m), 6.93 (1H, t), 3.77 (3H, s), 1.23 (2H, dd), 0.96 (2H, dd) |
| 38 | 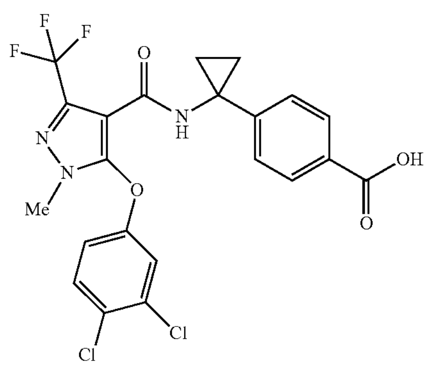 | ER-888363-00 | 1H NMR (400 MHz, CD3OD) δ ppm 7.81 (2H, d), 7.52 (1H, d), 7.33 (1H, d), 7.06 (2H, d), 7.00 (1H, dd), 3.82 (3H, s), 1.24 (2H, m), 0.95 (2H, m) |
| 39 | 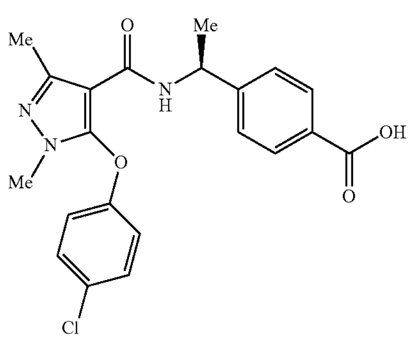 [SMILES: Cc1nn(C)c(Oc2ccc(Cl)cc2)c1C(=O)N[C@@H](C)c1ccc(C(=O)O)cc1] | ER-880663-00 | 1H NMR (400 MHz, CD3OD) δ ppm 7.83 (2 H, s), 7.74 (1 H, d), 7.33 (2 H, m), 7.13 (2 H, d), 6.93 (2 H, m), 5.01 (1 H, m), 3.62 (3 H, s), 2.35 (3 H, s), 1.35 (3H, d |

TABLE 1-continued

Analytical Data for Exemplary Compounds of Formula I

| Example | Structure | ER number | 1H NMR assignment |
|---|---|---|---|
| 40 | 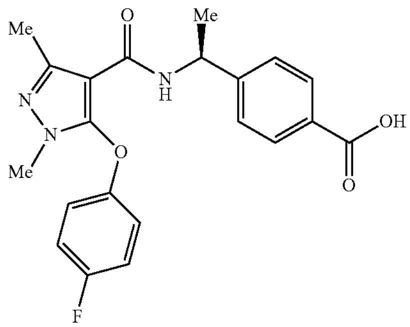 [SMILES: Cc1nn(C)c(Oc2ccc(F)cc2)c1C(=O)N[C@@H](C)c1ccc(C(=O)O)cc1] | ER-885302-00 | 1H NMR (400 MHz, CD3OD) δ ppm 7.78 (3 H, m) 7.05 (6 H, m) 5.01 (1 H, m) 3.62 (3 H, s) 2.35 (3 H, s) 1.35 (3 H, d) |
| 41 | 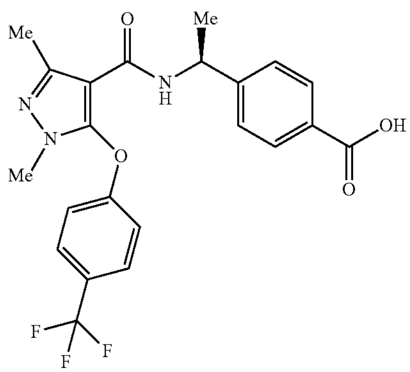 [SMILES: Cc1nn(C)c(Oc2ccc(C(F)(F)F)cc2)c1C(=O)N[C@@H](C)c1ccc(C(=O)O)cc1] | ER-885311-00 | 1H NMR (400 MHz, CD3OD) δ ppm 7.75 (5 H, m) 7.12 (4 H, m) 5.01 (1 H, m) 3.63 (3 H, s) 2.37 (3 H, s) 1.33 (3 H, d) |
| 42 | 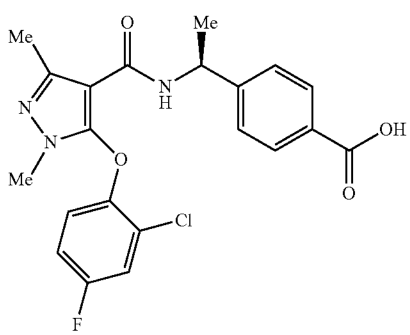 [SMILES: Cc1nn(C)c(Oc2ccc(F)cc2Cl)c1C(=O)N[C@@H](C)c1ccc(C(=O)O)cc1] | ER-886023-00 | 1H NMR (400 MHz, CD3OD) δ ppm 7.83 (2H, m), 7.30 (1H, m), 7.17 (2H, m), 6.95 (1H, m), 6.73 (1H, m), 5.00 (1H, m), 3.63 (3H, s), 2.33 (3H, s), 1.38 (3H, d) |
| 43 | 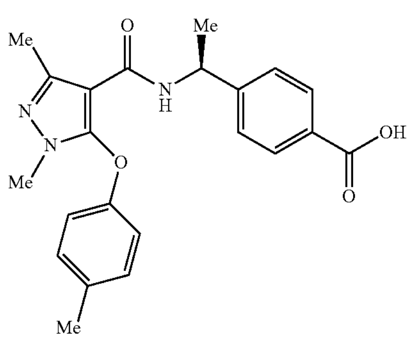 [SMILES: Cc1ccc(Oc2c(C(=O)N[C@@H](C)c3ccc(C(=O)O)cc3)c(C)nn2C)cc1] | ER-885749-00 | 1H NMR (400 MHz, CD3OD) δ ppm 7.77 (2H, d), 7.54 (1H, d), 7.14 (2H, d), 7.06 (2H, d), 6.80 (2H, d), 4.99 (1H, p), 3.59 (3H, s), 2.34 (3H, s), 2.32 (3H, s), 1.32 (3H, d) |

TABLE 1-continued

Analytical Data for Exemplary Compounds of Formula I

| Example | Structure | ER number | 1H NMR assignment |
|---------|-----------|-----------|-------------------|
| 44 | 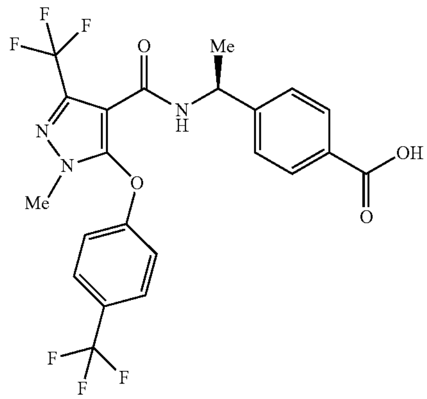 [SMILES: C[C@H](NC(=O)c1c(C(F)(F)F)nn(C)c1Oc1ccc(C(F)(F)F)cc1)c1ccc(C(=O)O)cc1] | ER-888365-00 | 1H NMR (400 MHz, CD3OD) δ ppm 8.60 (1H, d), 7.81 (2H, d), 7.64 (2H, d), 7.15 (4H, m), 4.94 (1H, m), 3.77 (3H, s), 1.31 (3H, d) |
| 45 | 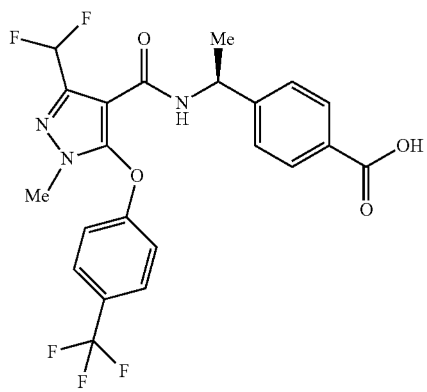 [SMILES: C[C@H](NC(=O)c1c(C(F)F)nn(C)c1Oc1ccc(C(F)(F)F)cc1)c1ccc(C(=O)O)cc1] | ER-888367-00 | 1H NMR (400 MHz, CD3OD) δ ppm 8.07 (1H, d), 7.81 (2H, d), 7.66 (2H, d), 7.14 (4H, m), 6.96 (1H, t), 4.99 (1H, m), 3.75 (3H, s), 1.34 (3H, d) |
| 46 | 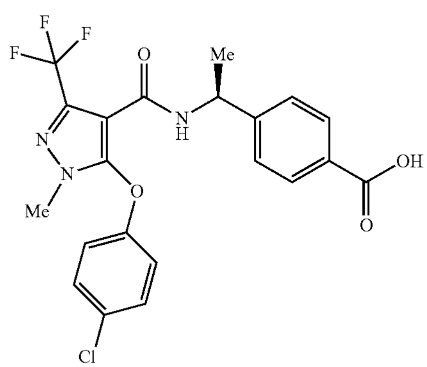 | ER-888369-00 | 1H NMR (400 MHz, CD3OD) δ ppm 8.53 (1H, d), 7.85 (2H, d), 7.30 (2H, d), 7.17 (2H, d), 6.97 (2H, d), 4.95 (1H, m), 3.77 (3H, s), 1.34 (3H, d) |
| 47 | 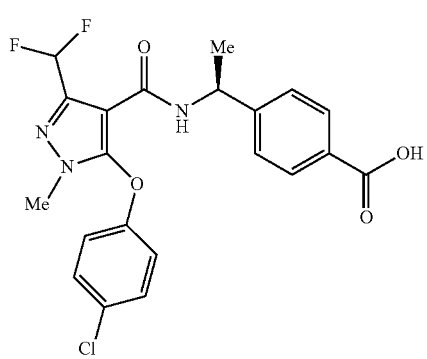 | ER-888371-00 | 1H NMR (400 MHz, CD3OD) δ ppm 7.99 (1H, d), 7.85 (2H, d), 7.33 (2H, d), 7.15 (2H, d), 6.96 (3H, m), 4.99 (1H, m), 3.74 (3H, s), 1.36 (3H, d) |

TABLE 1-continued

Analytical Data for Exemplary Compounds of Formula I

| Example | Structure | ER number | 1H NMR assignment |
| --- | --- | --- | --- |
| 48 | 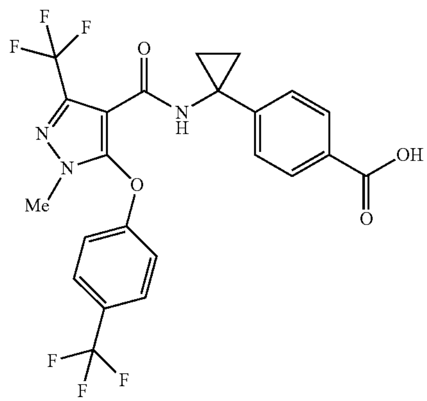 [SMILES: Cn1nc(C(F)(F)F)c(C(=O)NC2(c3ccc(C(=O)O)cc3)CC2)c1Oc1ccc(C(F)(F)F)cc1] | ER-888364-00 | 1H NMR (400 MHz, CD3OD) δ ppm 9.02 (1H, s), 7.76 (4H, m), 7.24 (2H, d), 7.03 (2H, d), 3.82 (3H, s), 1.21 (2H, m), 0.88 (2H, m) |
| 49 | 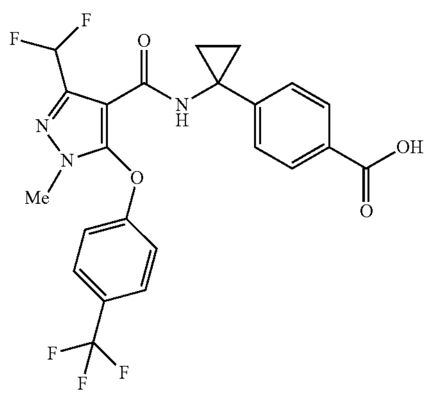 [SMILES: Cn1nc(C(F)F)c(C(=O)NC2(c3ccc(C(=O)O)cc3)CC2)c1Oc1ccc(C(F)(F)F)cc1] | ER-888366-00 | 1H NMR (400 MHz, CD3OD) δ ppm 8.64 (1H, s), 7.76 (4H, m), 7.22 (2H, d), 7.04 (2H, d), 6.95 (1H, t), 3.78 (3H, s), 1.23 (2H, m), 0.94 (2H, m) |
| 50 | 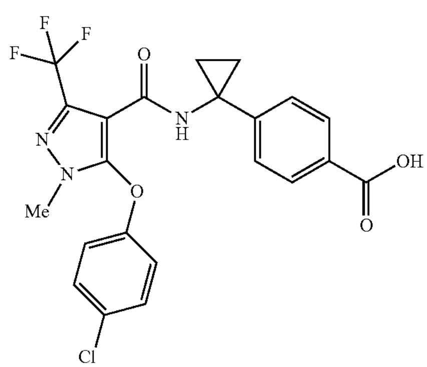 | ER-888368-00 | 1H NMR (400 MHz, CD3OD) δ ppm 7.81 (2H, d), 7.40 (2H, d), 7.04 (4H, m), 3.81 (3H, s), 1.23 (2H, m), 0.94 (2H, m) |
| 51 | 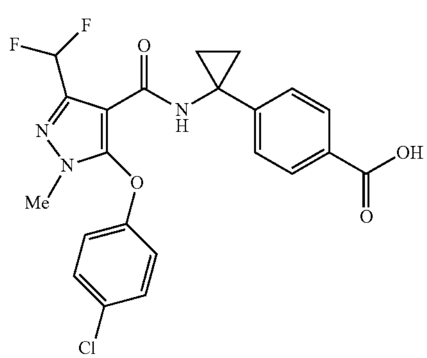 | ER-888370-00 | 1H NMR (400 MHz, CD3OD) δ ppm 7.81 (2H, d), 7.41 (2H, d), 7.03 (4H, m), 6.94 (1H, t), 3.77 (3H, s), 1.24 (2H, m), 1.00 (2H, m) |

Examples 52-111

In Vitro Biological Activity

CRE-PLAP Reporter Assay:

SE302 is a clone of the HEK/293 cell line that harbors a reporter construct containing a promoter with cAMP response elements (CRE) driving secreted alkaline phosphatase (PLAP), constructed by T. Arai, Eisai Pharamceuticals, Japan. These cells express endogenous EP4 and show induction of PLAP in response to PGE2 and other agonists of EP4, but not of EP1, 2 or 3 (data not shown). Cells were maintained in DMEM/F12 (50:50) (MediaTech) supplemented with 10% FBS (Tissue Culture Biologicals) plus penicillin/streptomycin. When used for assays, cells were plated in a 96-well plate at $2\times10^4$ cells/100 µL/well in serum-free assay medium (DMEM/F12 supplemented with 0.1% BSA plus penicillin/streptomycin) and incubated for 4-6 h. Cells were then stimulated with 3 $ng.mL^{-1}$ of PGE2 in the presence or absence of various concentrations of ER-819762 overnight, and PLAP activity was measured by mixing 15 µL of culture supernatants with 75 µL of Lumi-phos (Lumigen, Inc.) and 60 µL of assay buffer containing 8 $mmol.L^{-1}$ $MgSO_4$ in 0.1 $mol.L^{-1}$ carbonate-bicarbonate buffer pH11 in a new 96-well black plate and incubated for 2 h at room temperature. Luminescence was read with an Envision 2102 Multilabel reader.

Exemplary compounds of the present invention were assayed according to the methods set forth above in the CRE-PLAP reporter assay described above. Table 2 below sets forth exemplary compounds of the present invention having an $IC_{50}$ of up to 5.0 µM as determined by the normalized CRE-PLAP assay described above.

TABLE 2

$IC_{50}$ Values Exemplary Compounds

| Example | Structure | ER number | CRE-PLAP IC50 (µM) |
|---------|-----------|-----------|--------------------|
| 52 | 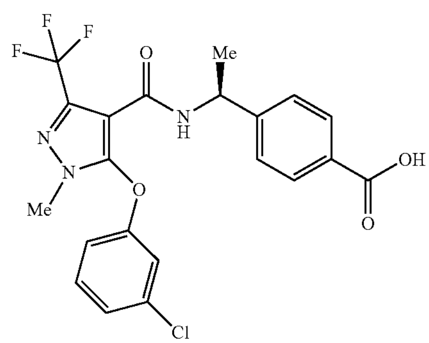 [SMILES: C[C@H](NC(=O)c1c(C(F)(F)F)nn(C)c1Oc1cccc(Cl)c1)c1ccc(C(=O)O)cc1] | ER-885289-00 | 0.045 |
| 53 | 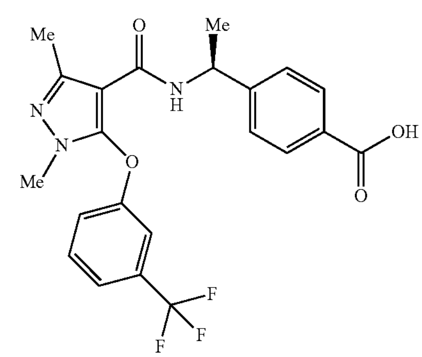 [SMILES: Cc1nn(C)c(Oc2cccc(C(F)(F)F)c2)c1C(=O)N[C@@H](C)c1ccc(C(=O)O)cc1] | ER-885290-00 | 0.018 |
| 54 | 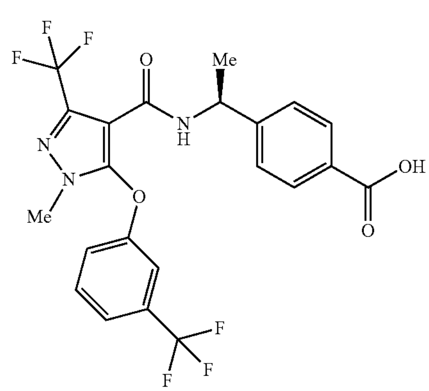 [SMILES: C[C@H](NC(=O)c1c(C(F)(F)F)nn(C)c1Oc1cccc(C(F)(F)F)c1)c1ccc(C(=O)O)cc1] | ER-885291-00 | 0.027 |

TABLE 2-continued

IC$_{50}$ Values Exemplary Compounds

| Example | Structure | ER number | CRE-PLAP IC50 (μM) |
|---|---|---|---|
| 55 | 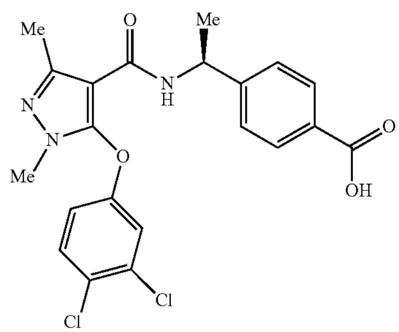 [SMILES: Cc1nn(C)c(Oc2ccc(Cl)c(Cl)c2)c1C(=O)N[C@@H](C)c1ccc(C(=O)O)cc1] | ER-885716-00 | 0.092 |
| 56 | 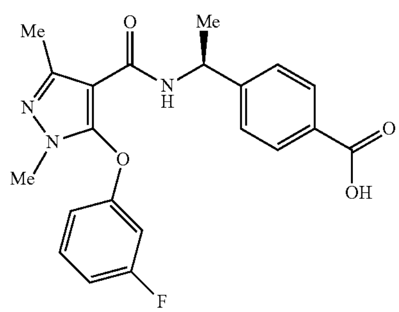 [SMILES: Cc1nn(C)c(Oc2cccc(F)c2)c1C(=O)N[C@@H](C)c1ccc(C(=O)O)cc1] | ER-885717-00 | 0.974 |
| 57 | 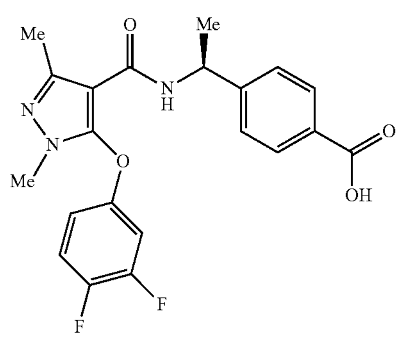 [SMILES: Cc1nn(C)c(Oc2ccc(F)c(F)c2)c1C(=O)N[C@@H](C)c1ccc(C(=O)O)cc1] | ER-885718-00 | 0.467 |
| 58 | 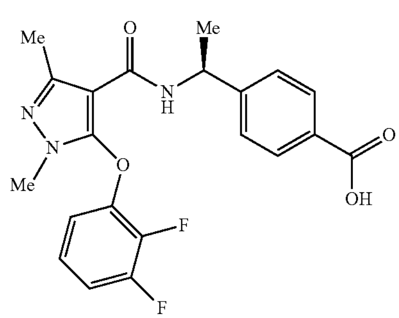 [SMILES: Cc1nn(C)c(Oc2cccc(F)c2F)c1C(=O)N[C@@H](C)c1ccc(C(=O)O)cc1] | ER-885719-00 | 2.666 |

TABLE 2-continued

| | IC$_{50}$ Values Exemplary Compounds | | |
|---|---|---|---|
| Example | Structure | ER number | CRE-PLAP IC50 (μM) |
| 59 | | ER-885720-00 | 2.219 |
| 60 | | ER-885721-00 | 0.846 |
| 61 | | ER-885740-00 | 0.012 |
| 62 | | ER-885741-00 | 0.013 |

TABLE 2-continued

IC₅₀ Values Exemplary Compounds

| Example | Structure | ER number | CRE-PLAP IC50 (μM) |
|---|---|---|---|
| 63 | 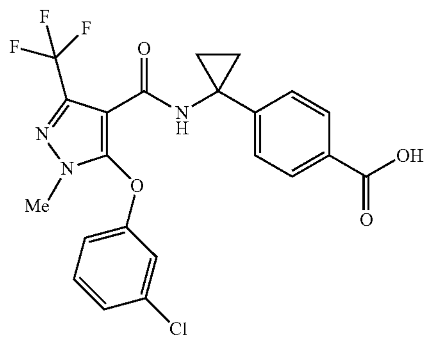 [SMILES: Cn1nc(C(F)(F)F)c(C(=O)NC2(c3ccc(C(=O)O)cc3)CC2)c1Oc1cccc(Cl)c1] | ER-885743-00 | 0.038 |
| 64 | 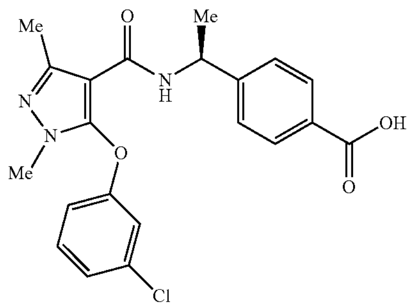 [SMILES: Cc1nn(C)c(Oc2cccc(Cl)c2)c1C(=O)N[C@@H](C)c1ccc(C(=O)O)cc1] | ER-885744-00 | 0.168 |
| 65 | 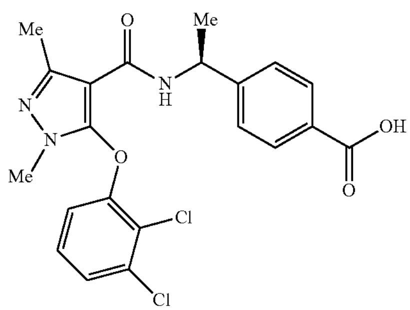 [SMILES: Cc1nn(C)c(Oc2cccc(Cl)c2Cl)c1C(=O)N[C@@H](C)c1ccc(C(=O)O)cc1] | ER-886022-00 | 0.719 |
| 66 | 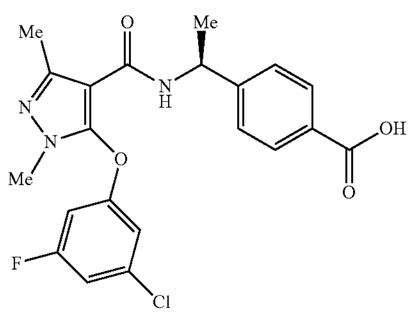 [SMILES: Cc1nn(C)c(Oc2cc(F)cc(Cl)c2)c1C(=O)N[C@@H](C)c1ccc(C(=O)O)cc1] | ER-886024-00 | 0.637 |
| 67 | 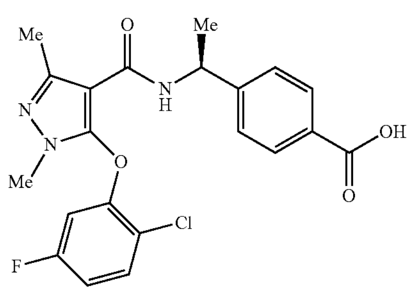 [SMILES: Cc1nn(C)c(Oc2cc(F)ccc2Cl)c1C(=O)N[C@@H](C)c1ccc(C(=O)O)cc1] | ER-886025-00 | 4.914 |

TABLE 2-continued

| | IC$_{50}$ Values Exemplary Compounds | | |
|---|---|---|---|
| Example | Structure | ER number | CRE-PLAP IC50 (μM) |
| 68 | | ER-886032-00 | 0.356 |
| 69 | | ER-886033-00 | 2.122 |
| 70 | | ER-886035-00 | 3.665 |
| 71 | | ER-886045-00 | 0.018 |

TABLE 2-continued
| Example | Structure | ER number | CRE-PLAP IC50 (μM) |
|---|---|---|---|
| 72 | 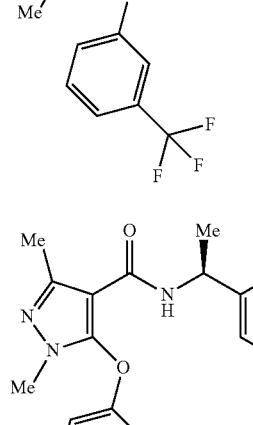 | ER-886046-00 | 0.011 |
| 73 | 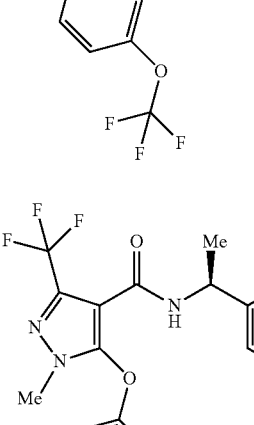 | ER-886061-00 | 0.089 |
| 74 | 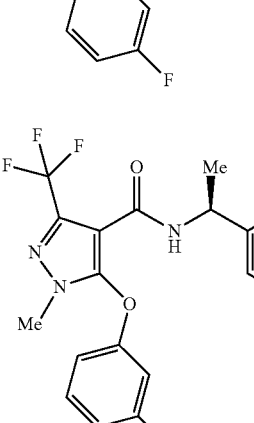 | ER-886072-00 | 0.132 |
| 75 | 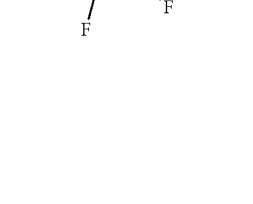 | ER-886073-00 | 0.109 |

TABLE 2-continued

| | IC$_{50}$ Values Exemplary Compounds | | |
|---|---|---|---|
| Example | Structure | ER number | CRE-PLAP IC50 (μM) |
| 76 | | ER-886074-00 | 0.01 |
| 77 | | ER-886077-00 | 0.085 |
| 78 | | ER-886078-00 | 0.009 |
| 79 | | ER-886080-00 | 0.058 |

TABLE 2-continued

IC$_{50}$ Values Exemplary Compounds

| Example | Structure | ER number | CRE-PLAP IC50 (μM) |
|---------|-----------|-----------|---------------------|
| 80 | 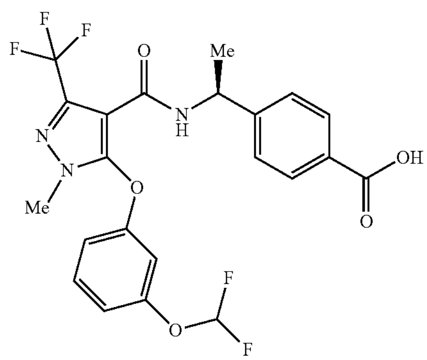 [SMILES: C[C@H](NC(=O)c1c(C(F)(F)F)nn(C)c1Oc1cccc(OC(F)F)c1)c1ccc(C(=O)O)cc1] | ER-886082-00 | 0.088 |
| 81 | 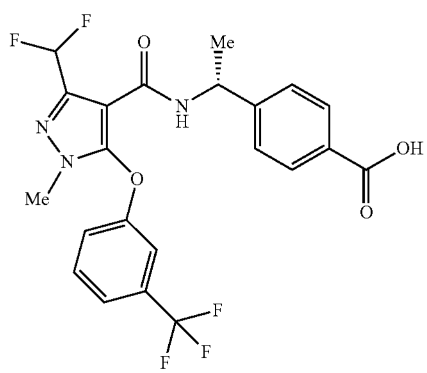 [SMILES: C[C@@H](NC(=O)c1c(C(F)F)nn(C)c1Oc1cccc(C(F)(F)F)c1)c1ccc(C(=O)O)cc1] | ER-886083-00 | 0.827 |
| 82 | 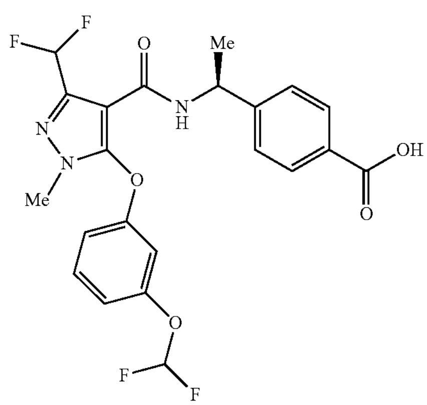 [SMILES: C[C@H](NC(=O)c1c(C(F)F)nn(C)c1Oc1cccc(OC(F)F)c1)c1ccc(C(=O)O)cc1] | ER-886090-00 | 0.017 |
| 83 | 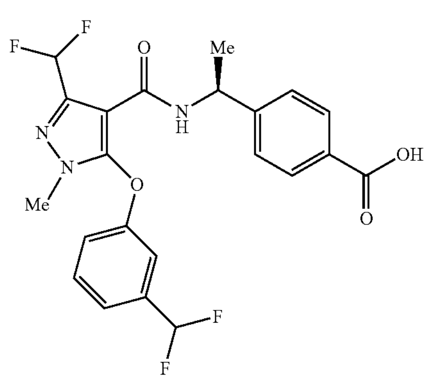 [SMILES: C[C@H](NC(=O)c1c(C(F)F)nn(C)c1Oc1cccc(C(F)F)c1)c1ccc(C(=O)O)cc1] | ER-887480-00 | 0.051 |

TABLE 2-continued

IC$_{50}$ Values Exemplary Compounds

| Example | Structure | ER number | CRE-PLAP IC50 (μM) |
|---------|-----------|-----------|--------------------|
| 84 | 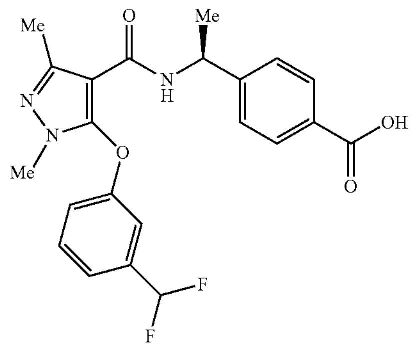 [SMILES: Cc1nn(C)c(Oc2cccc(C(F)F)c2)c1C(=O)N[C@@H](C)c1ccc(C(=O)O)cc1] | ER-887495-00 | 0.219 |
| 85 | 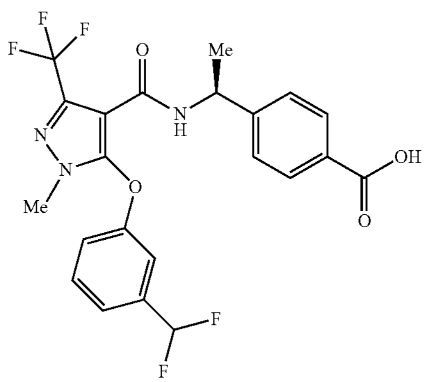 [SMILES: C[C@H](NC(=O)c1c(C(F)(F)F)nn(C)c1Oc1cccc(C(F)F)c1)c1ccc(C(=O)O)cc1] | ER-887995-00 | 0.187 |
| 86 | 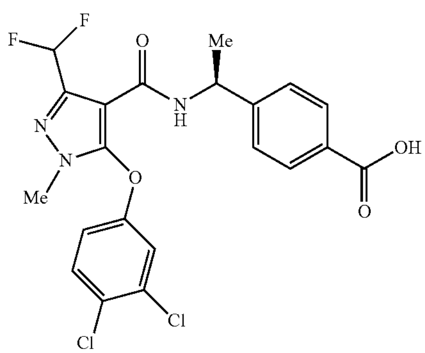 [SMILES: C[C@H](NC(=O)c1c(C(F)F)nn(C)c1Oc1ccc(Cl)c(Cl)c1)c1ccc(C(=O)O)cc1] | ER-888024-00 | 0.031 |
| 87 | 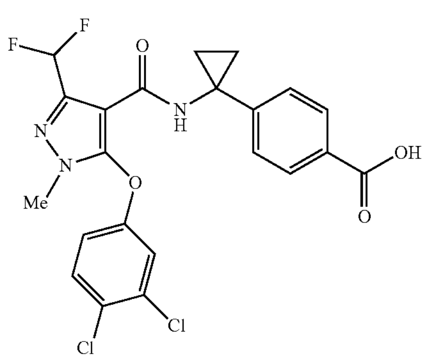 [SMILES: Cn1nc(C(F)F)c(C(=O)NC2(c3ccc(C(=O)O)cc3)CC2)c1Oc1ccc(Cl)c(Cl)c1] | ER-888348-00 | 0.017 |

TABLE 2-continued

| | IC$_{50}$ Values Exemplary Compounds | | |
|---|---|---|---|
| Example | Structure | ER number | CRE-PLAP IC50 (μM) |
| 88 | | ER-888355-00 | 0.157 |
| 89 | | ER-888363-00 | 0.008 |
| 90 | | ER-880663-00 | 0619 |
| 91 | | ER-885302-00 | 0.261 |

TABLE 2-continued

IC$_{50}$ Values Exemplary Compounds

| Example | Structure | ER number | CRE-PLAP IC50 (μM) |
|---|---|---|---|
| 92 | 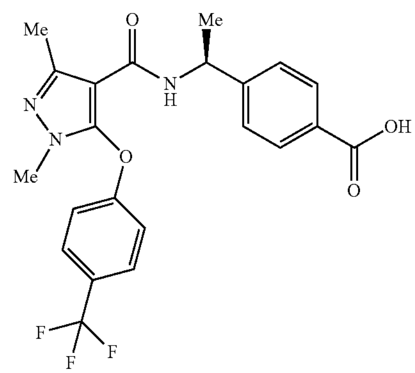 [SMILES: Cc1nn(C)c(Oc2ccc(C(F)(F)F)cc2)c1C(=O)N[C@@H](C)c1ccc(C(=O)O)cc1] | ER-885311-00 | 0.273 |
| 93 | 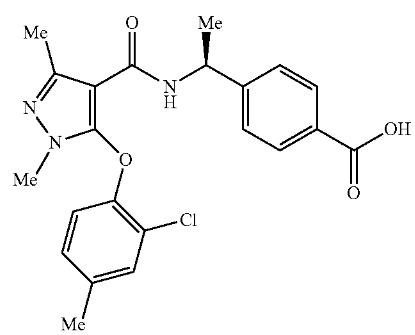 [SMILES: Cc1ccc(Oc2c(C(=O)N[C@@H](C)c3ccc(C(=O)O)cc3)c(C)nn2C)c(Cl)c1] | ER-886023-00 | 4.403 |
| 94 | 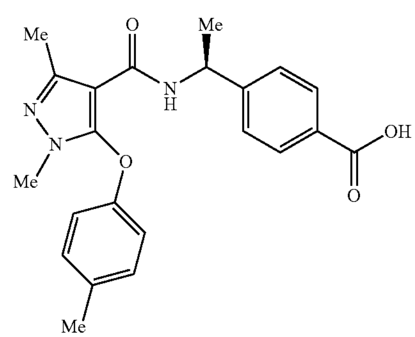 [SMILES: Cc1ccc(Oc2c(C(=O)N[C@@H](C)c3ccc(C(=O)O)cc3)c(C)nn2C)cc1] | ER-885749-00 | 0.451 |
| 95 | 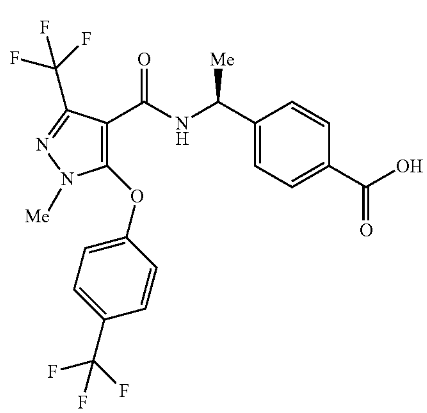 [SMILES: C[C@H](NC(=O)c1c(C(F)(F)F)nn(C)c1Oc1ccc(C(F)(F)F)cc1)c1ccc(C(=O)O)cc1] | ER-888365-00 | 0.028 |

TABLE 2-continued

| | IC$_{50}$ Values Exemplary Compounds | | |
|---|---|---|---|
| Example | Structure | ER number | CRE-PLAP IC50 (μM) |
| 96 | | ER-888367-00 | 0.023 |
| 97 | | ER-888369-00 | 0.089 |
| 98 | | ER-888371-00 | 0.089 |
| 99 | | ER-888364-00 | 0.012 |

TABLE 2-continued

IC$_{50}$ Values Exemplary Compounds

| Example | Structure | ER number | CRE-PLAP IC50 (μM) |
|---|---|---|---|
| 100 | 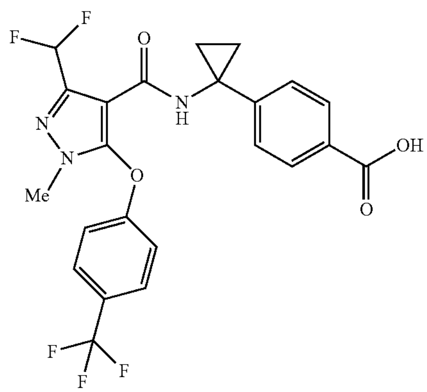 [SMILES: Cn1nc(C(F)F)c(C(=O)NC2(c3ccc(C(=O)O)cc3)CC2)c1Oc1ccc(C(F)(F)F)cc1] | ER-888366-00 | 0.015 |
| 101 | 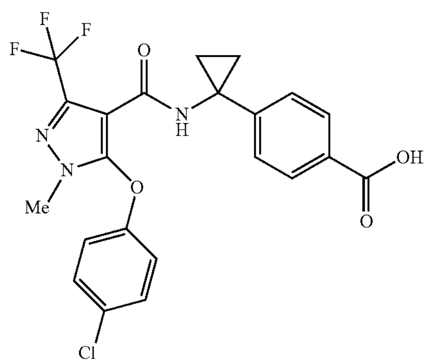 [SMILES: Cn1nc(C(F)(F)F)c(C(=O)NC2(c3ccc(C(=O)O)cc3)CC2)c1Oc1ccc(Cl)cc1] | ER-888368-00 | 0.018 |
| 102 | 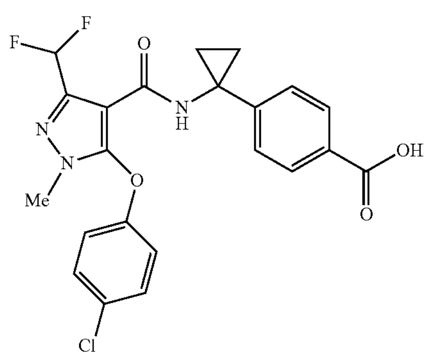 [SMILES: Cn1nc(C(F)F)c(C(=O)NC2(c3ccc(C(=O)O)cc3)CC2)c1Oc1ccc(Cl)cc1] | ER-888370-00 | 0.035 |

Radioligand EP4 Receptor Binding Assay:

The radioligand EP$_4$ binding assay was performed using ChemiScreen recombinant human EP$_4$ receptor membrane preparations from Millipore, according to manufacturer's instructions. Briefly, membranes prepared from Chem-1 cells overexpressing human EP$_4$ cDNA (Millipore) were mixed with 1.8 nmol.L$^{-1}$ [$^3$H]-PGE$_2$ and 5 μmol.L$^{-1}$ unlabelled PGE$_2$ in the presence or absence of various concentrations of testing compounds in binding buffer (50 mmol.L$^{-1}$ HEPES, pH 7.4, 5 mmol.L$^{-1}$ MgCl$_2$, 1 mmol.L$^{-1}$ CaCl$_2$, 0.2% BSA) in a nonbinding 96-well plate, and incubated for 1-2 h at room temperature. Prior to filtration, a GF/C 96-well filter plate was coated with 0.33% polyethyleneimine for 30 min, then washed with 50 mmol.L$^{-1}$ HEPES, pH 7.4, 0.5% BSA. Binding reactions were transferred to the filter plate, and washed 3 times with Wash Buffer (1 mL per well per wash). The plate was dried and radioactivity counted. Binding of testing compounds to other related prostanoid receptors was performed by MDS Pharma Services (Bothell, Wash.) using a similar radiolabeled ligand displacement method.

Exemplary compounds of the present invention were assayed according to the methods set forth above in the radioligand EP4 receptor binding assay described above. Table 3 below sets forth exemplary compounds of the present invention having Ki values as determined by the radioligand EP4 receptor binding assay described above.

TABLE 3

| Example | Structure | ER-number | EP4 binding Ki (μM) |
|---|---|---|---|
| 103 | 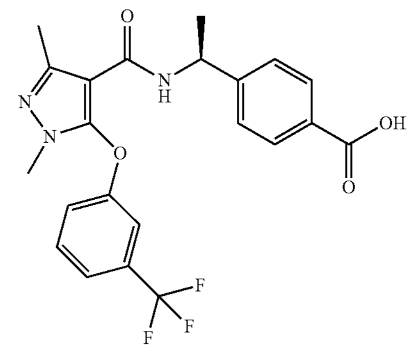 [SMILES: Cc1nn(C)c(Oc2cccc(C(F)(F)F)c2)c1C(=O)N[C@@H](C)c1ccc(C(=O)O)cc1] | ER-885290-00 | 0.014 |
| 104 | 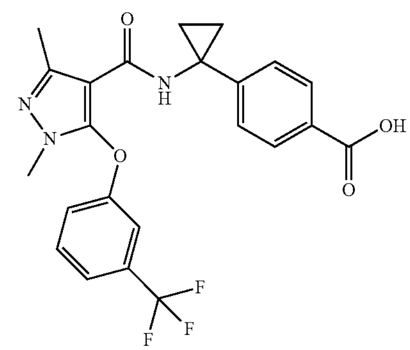 [SMILES: Cc1nn(C)c(Oc2cccc(C(F)(F)F)c2)c1C(=O)NC1(c2ccc(C(=O)O)cc2)CC1] | ER-885740-00 | 0.043 |
| 105 | 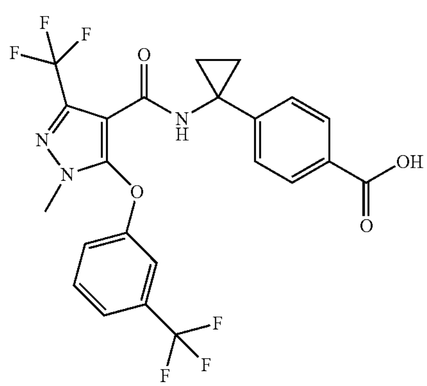 [SMILES: Cn1nc(C(F)(F)F)c(C(=O)NC2(c3ccc(C(=O)O)cc3)CC2)c1Oc1cccc(C(F)(F)F)c1] | ER-885741-00 | 0.016 |
| 106 | 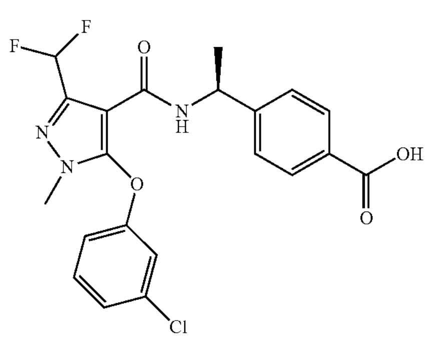 [SMILES: C[C@H](NC(=O)c1c(C(F)F)nn(C)c1Oc1cccc(Cl)c1)c1ccc(C(=O)O)cc1] | ER-886045-00 | 0.050 |

TABLE 3-continued

Ki Values of Exemplary Compounds

| Example | Structure | ER-number | EP4 binding Ki (μM) |
|---------|-----------|-----------|---------------------|
| 107 | 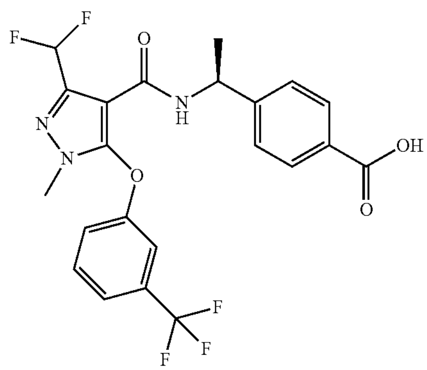 [SMILES: C[C@H](NC(=O)c1c(C(F)F)nn(C)c1Oc1cccc(C(F)(F)F)c1)c1ccc(C(=O)O)cc1] | ER-886046-00 | 0.008 |
| 108 | 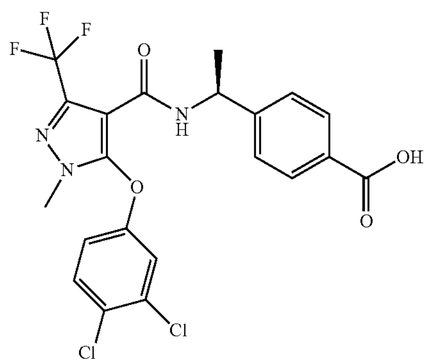 [SMILES: C[C@H](NC(=O)c1c(C(F)(F)F)nn(C)c1Oc1ccc(Cl)c(Cl)c1)c1ccc(C(=O)O)cc1] | ER-886074-00 | 0.013 |
| 109 | 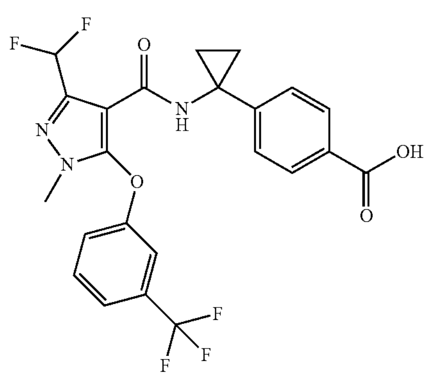 [SMILES: Cn1nc(C(F)F)c(C(=O)NC2(c3ccc(C(=O)O)cc3)CC2)c1Oc1cccc(C(F)(F)F)c1] | ER-886078-00 | 0.008 |
| 110 | 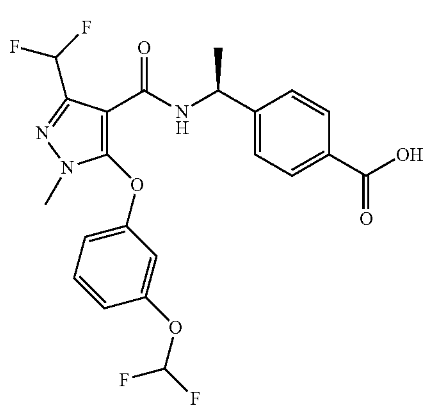 [SMILES: C[C@H](NC(=O)c1c(C(F)F)nn(C)c1Oc1cccc(OC(F)F)c1)c1ccc(C(=O)O)cc1] | ER-886090-00 | 0.010 |

TABLE 3-continued

Ki Values of Exemplary Compounds

| Example | Structure | ER-number | EP4 binding Ki (μM) |
|---|---|---|---|
| 111 | ![structure] | ER-887480-00 | 0.026 |

Examples 112-113

In Vivo Biological Activity

Example 112

Suppression of Arthritis Development in CIA Model

Male DBA/1 mice were immunized by injection at the base of the tail with 0.1 mL emulsion containing 150 μg bovine type II collagen (bCII) emulsified in CFA. Three weeks after the $1^{st}$ immunization, all mice were boosted with bovine type II collagen emulsified in Freund's incomplete adjuvant, ER-886046 was orally administered daily at a dose of 10, 30 or 100 mg.kg$^{-1}$ from day 20 after primary immunization but before disease onset (prophylactic evaluation) or after the disease induction (therapeutic evaluation). The severity of arthritic symptoms in the paws of each mouse was graded every other days, double-blind, according to Williams R O (Collagen-induced arthritis as a model for rheumatoid arthritis. *Methods Mol Med* 2004, 98:207-216). Results are given in FIG. 1.

Example 113

Figure 2:
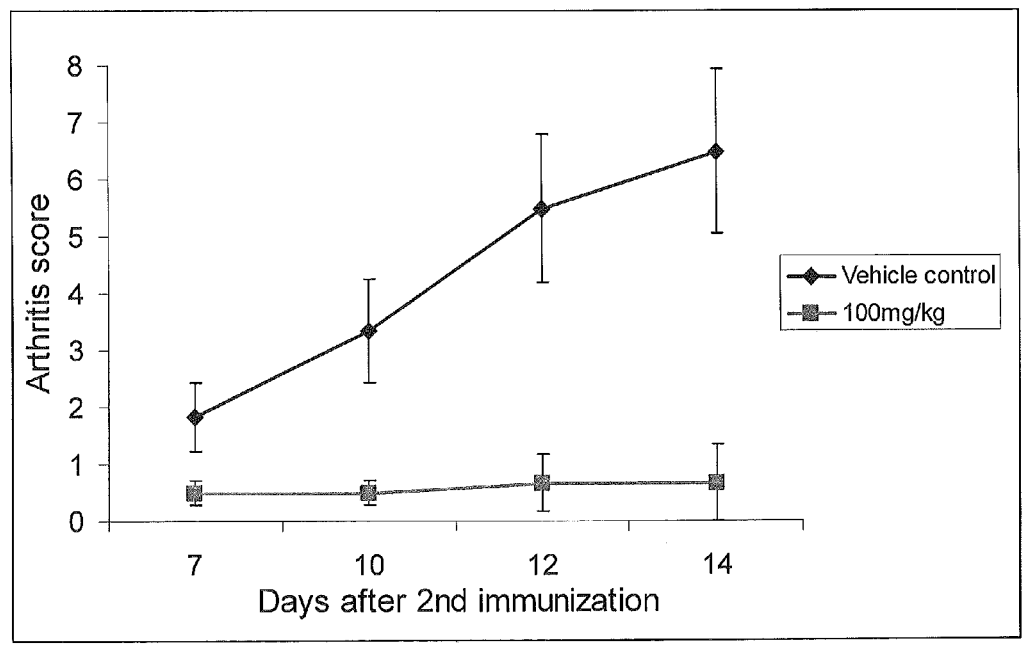
FIG. 2: Suppression of arthritis development in a glucose-6-phosphate isomerase (G6PI) model with a compound of the present invention.

Suppression of Arthritis Development in Glucose-6-Phosphate Isomerase (G6PI) Model Male DBA/1 mice were immunized by injecting at the base of the tail 0.15 mL of emulsion containing 300 μg recombinant human GPI-glutathione-S-transferase (GST) fusion protein (hGPI) in CFA. ER-886046 was orally administered daily at a dose of 100 mg.kg$^{-1}$ from day 6 after primary immunization but before disease onset (prophylactic evaluation) or after the disease induction (therapeutic evaluation). Each treatment group consisted of 6-8 mice. Arthritic animals were clinically assessed every other day by an arthritis scoring system as follows (Iwanami K, Matsumoto I, Tanaka-Watanabe Y, Mihira M, Ohsugi Y, Mamura M et al. Crucial role of IL-6/IL-17 axis in the induction of arthritis by glucose-6-phosphate isomerase. *Arthritis Rheum* 2008, 58:754-763): 0=no evidence of inflammation, 1=subtle inflammation or localized edema, 2=easily identified swelling but localized to dorsal or ventral surface of paws, and score 3=swelling on all aspects of paws. Results are given in FIG. 2.

Certain Embodiments of the Invention

1. A compound of formula I:

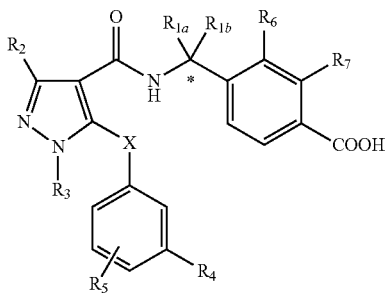

wherein:
one of $R_{1a}$ and $R_{1b}$ is hydrogen, and the other is methyl; or $R_{1a}$ and $R_{1b}$ are taken together to form a cyclopropyl ring;
$R_2$ is methyl or fluoromethyl (e.g., monofluoromethyl, difluoromethyl, or trifluoromethyl);
$R_3$ is methyl;
$R_4$ is hydrogen, halo, fluoromethyl, methoxy, or fluoromethoxy (e.g., monofluoromethoxy, difluoromethoxy, or trifluoromethoxy);
$R_5$ is hydrogen, halo, fluoromethyl, methoxy, or fluoromethoxy;
$R_6$ is hydrogen, halo, methyl, or methoxy;
$R_7$ is hydrogen, halo, methyl, or methoxy; and
X is oxygen;
or pharmaceutically acceptable salts thereof.

2. The compound of embodiment 1, wherein
one of $R_{1a}$ and $R_{1b}$ is hydrogen, and the other is methyl; $R_2$ is methyl, difluoromethyl, or trifluoromethyl;
$R_3$ is methyl;
$R_4$ is chloro, fluoro, trifluoromethyl, difluoromethyl, methyl, methoxy, difluoromethoxy, or trifluoromethoxy;
$R_5$ is hydrogen, chloro, fluoro, methyl, or methoxy;
$R_6$ and $R_7$ are hydrogen;
or a pharmaceutically acceptable salt thereof.

3. The compound of embodiment 2, wherein $R_5$ is hydrogen; or a
pharmaceutically acceptable salt thereof
4. The compound of embodiment 3, wherein $R_4$ is selected from chloro, trifluoromethyl, difluoromethyl, difluoromethoxy, and trifluoromethoxy;
or a pharmaceutically acceptable salt thereof.
5. The compound of any one of embodiments 1-4, wherein, one of $R_{1a}$ and $R_{1b}$ is hydrogen, and the other is methyl, and the compound of Formula I consists of a mixture of stereoisomers;
or a pharmaceutically acceptable salt thereof.
6. The compound of any one of embodiments 1-4, wherein, one of $R_{1a}$ and $R_{1b}$ is hydrogen, and the other is methyl, and the compound of Formula I consists of a substantially pure stereoisomer;
or a pharmaceutically acceptable salt thereof.
7. The compound of embodiment 6, wherein,
one of $R_{1a}$ and $R_{1b}$ is hydrogen, and the other is methyl, and the carbon of the compound of Formula I marked with a * has substantially the S-configuration;
or a pharmaceutically acceptable salt thereof.
8. The compound of embodiment 6, wherein,
one of $R_{1a}$ and $R_{1b}$ is hydrogen, and the other is methyl, and the carbon of the compound of Formula I marked with a * has substantially the R-configuration;
or a pharmaceutically acceptable salt thereof.
9. The compound of embodiment 1, wherein
$R_{1a}$ and $R_{1b}$ are taken together to form a cyclopropyl ring;
$R_2$ is methyl, trifluoromethyl, or difluoromethyl;
$R_3$ is methyl;
$R_4$ is trifluoromethyl, difluoromethyl, chloro, or fluoro;
$R_6$ and $R_7$ are hydrogen;
or a pharmaceutically acceptable salt thereof.
10. The compound of embodiment 1, selected from the group consisting of:

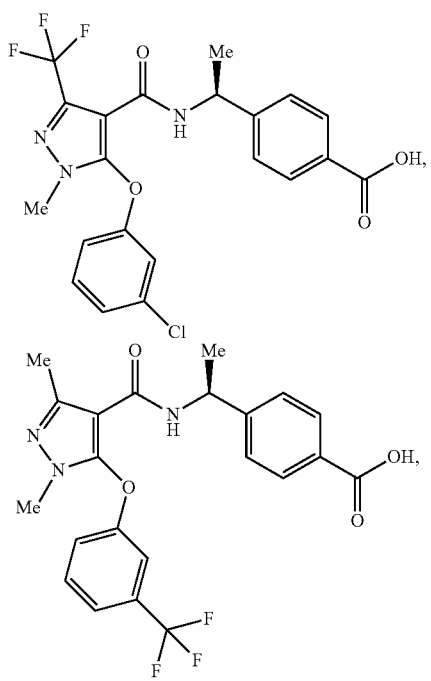

-continued

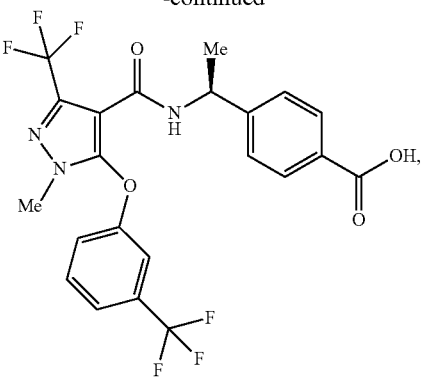

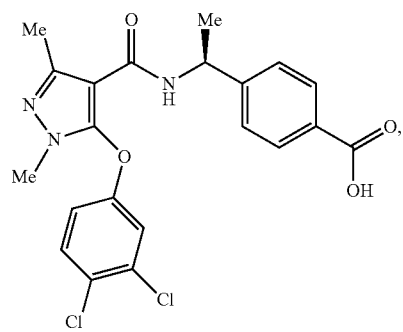

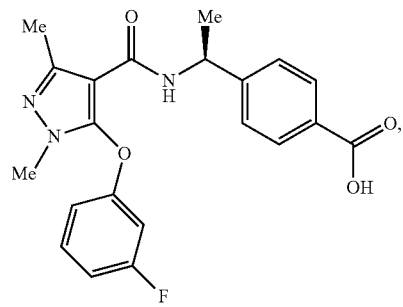

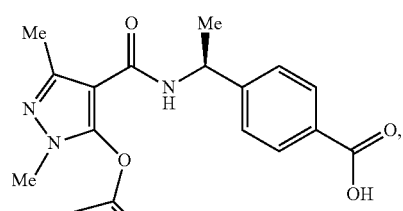

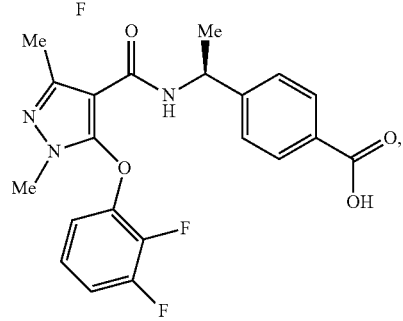

93
-continued
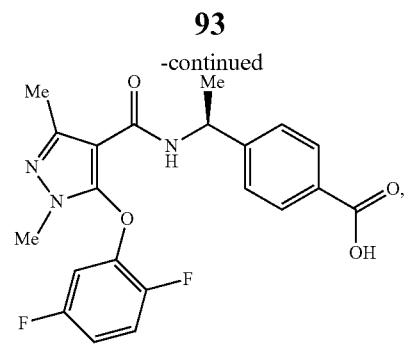
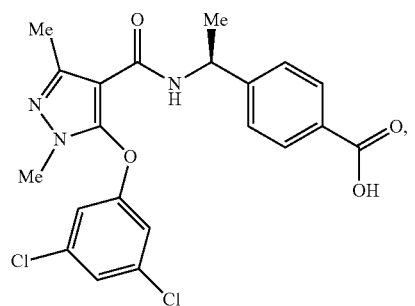
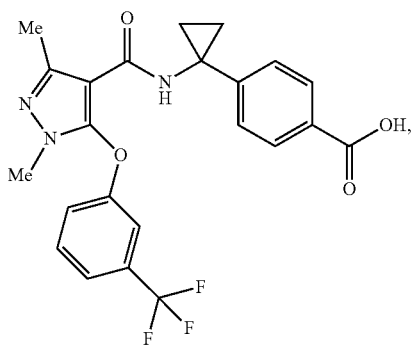
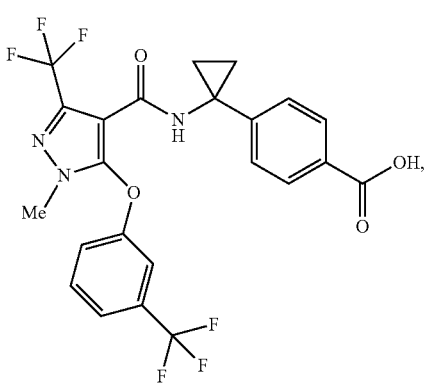
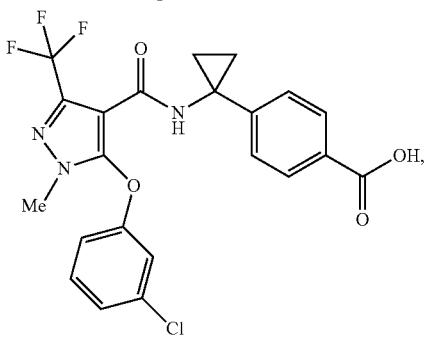
94
-continued
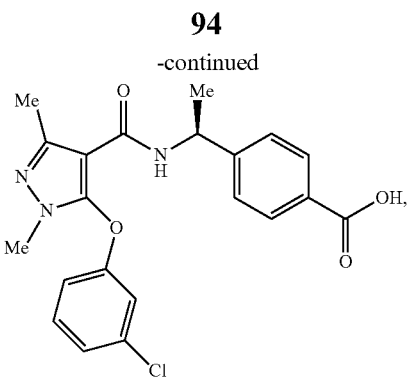
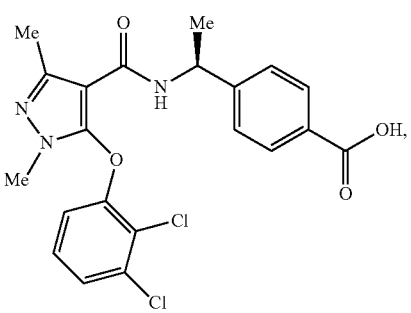
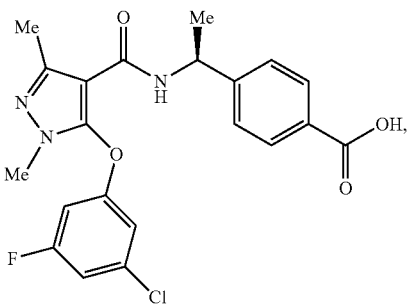
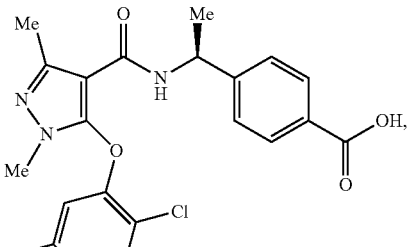
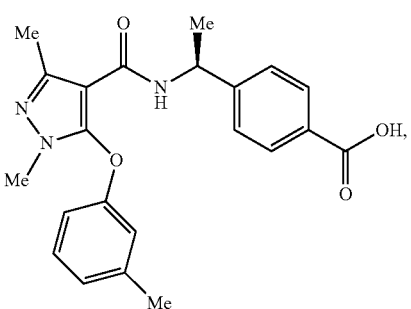

-continued
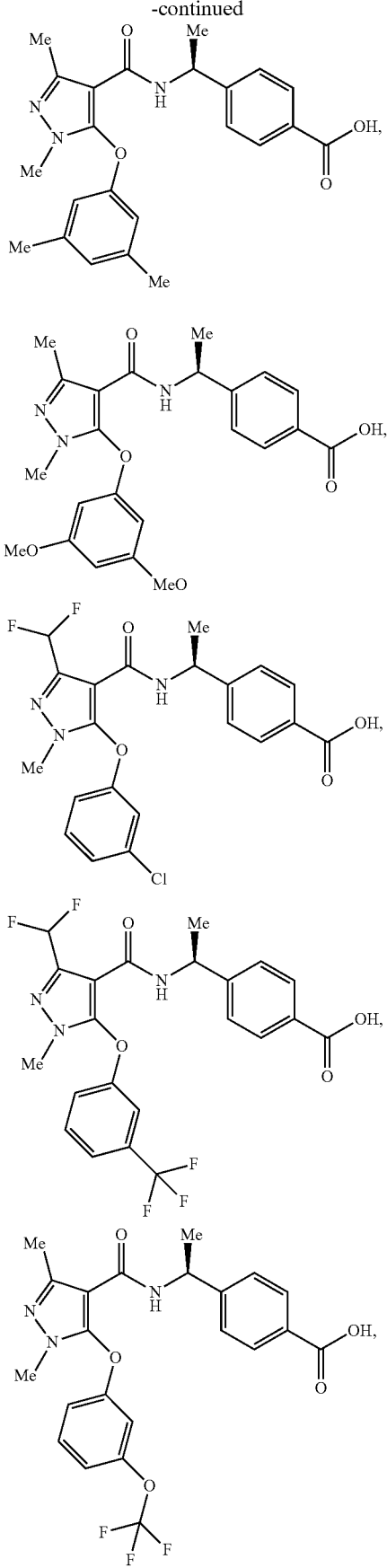
-continued
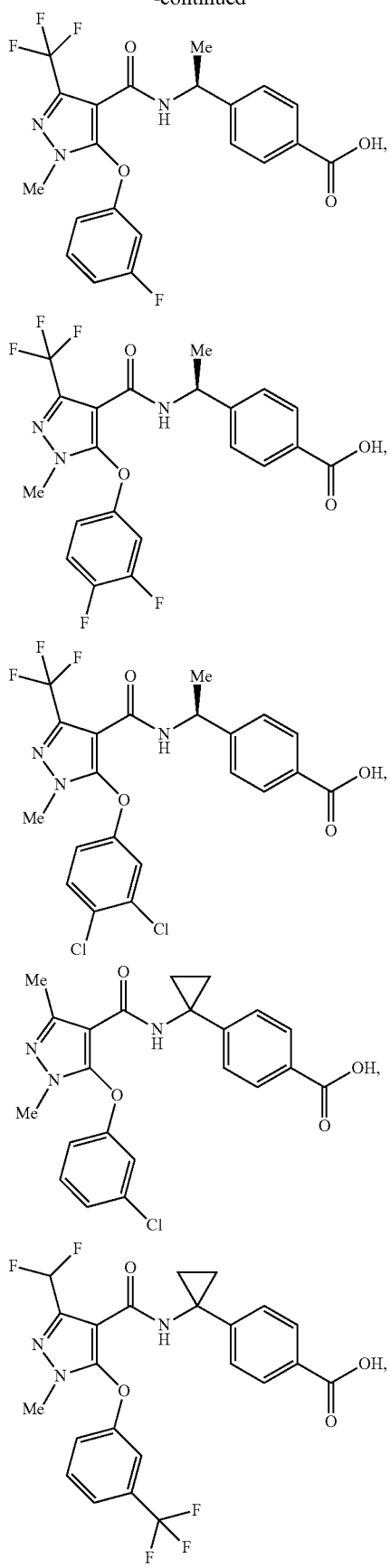

97
-continued
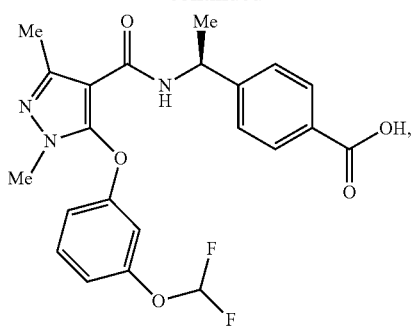
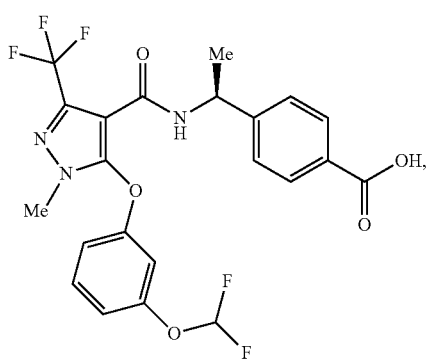
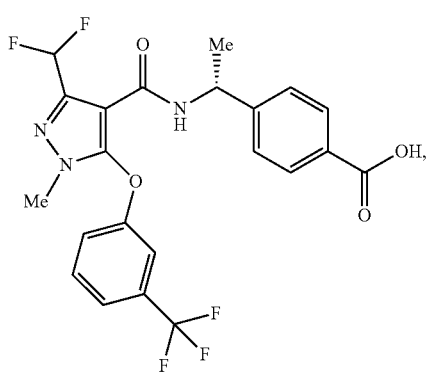
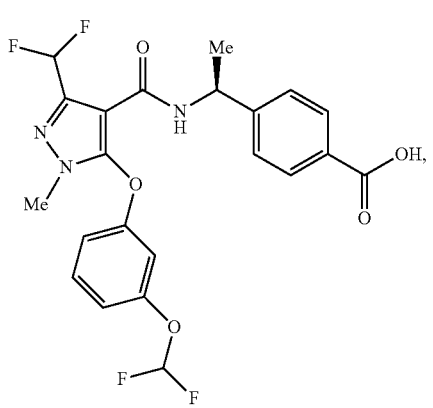
98
-continued
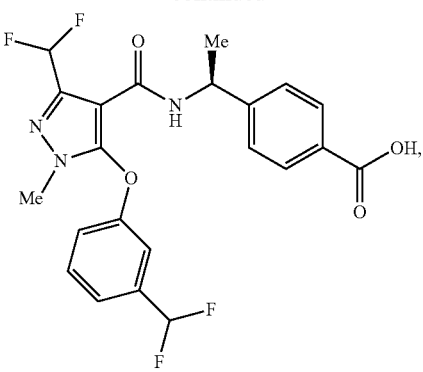 [SMILES: C[C@H](NC(=O)c1c(C(F)F)nn(C)c1Oc1cccc(C(F)(F)F)c1)c1ccc(C(=O)O)cc1]
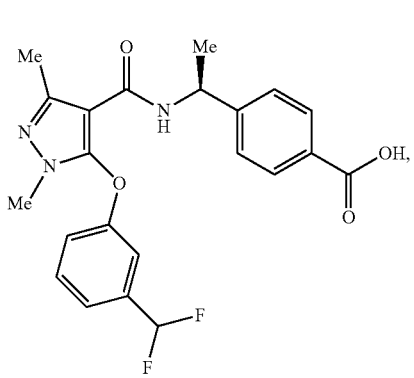
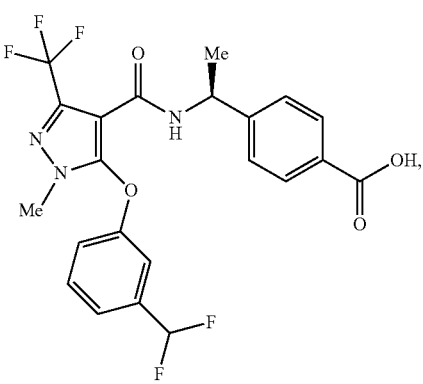
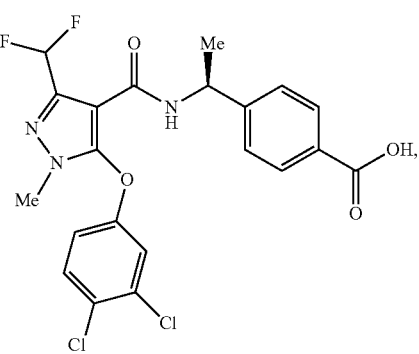

99
-continued
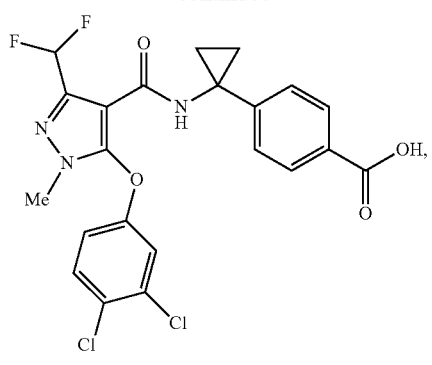
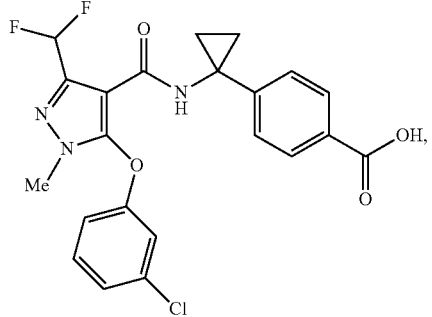
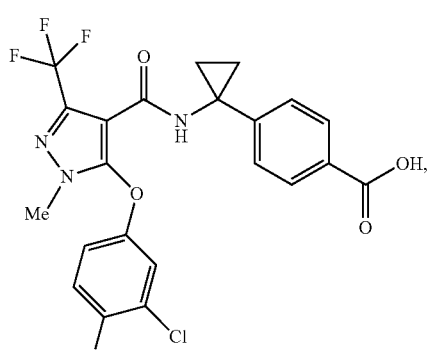
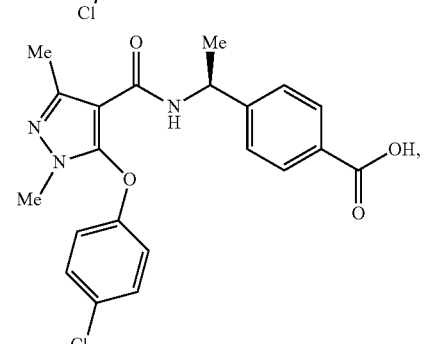
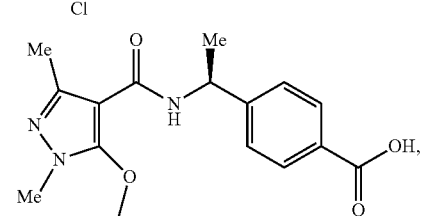
100
-continued
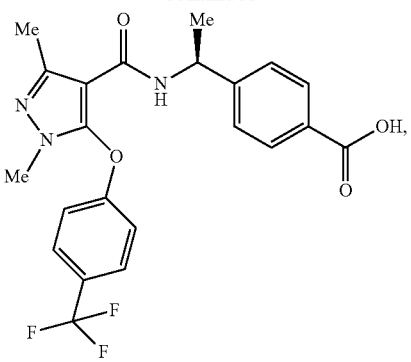
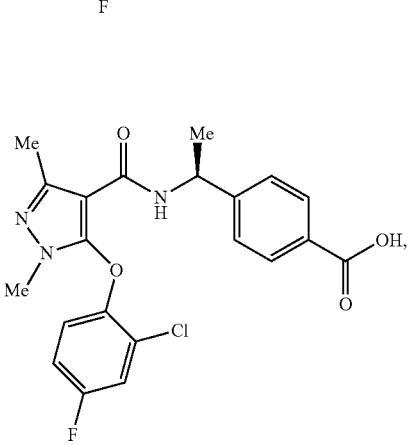
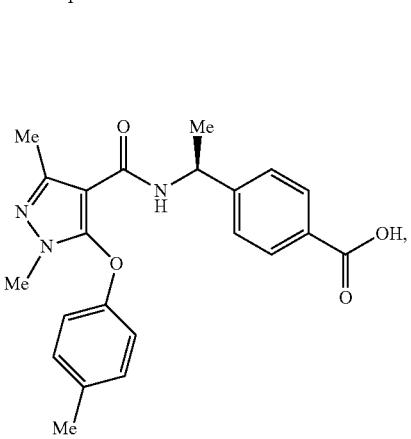
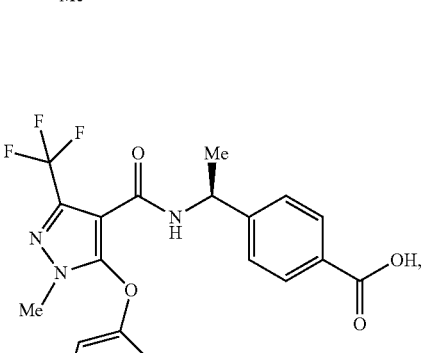

-continued
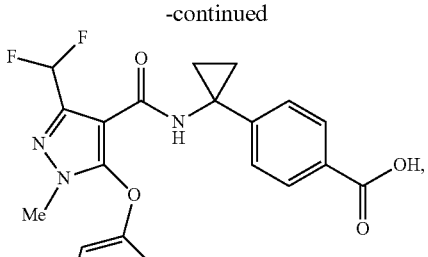
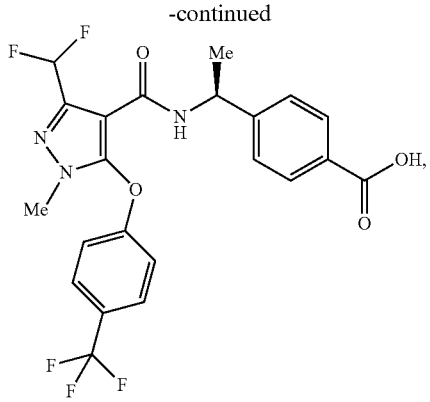
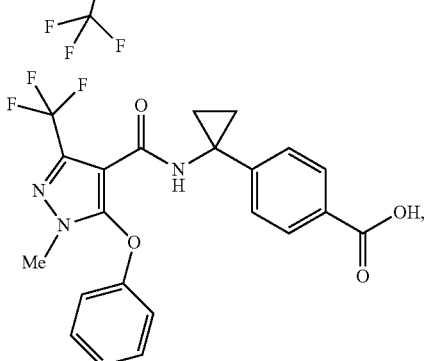
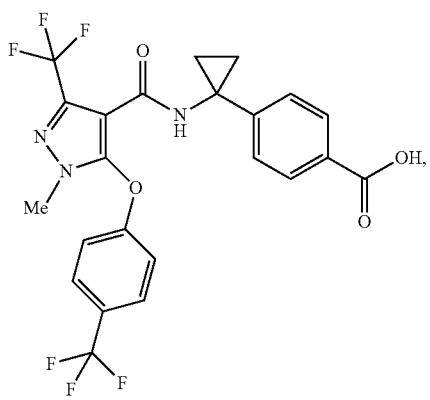
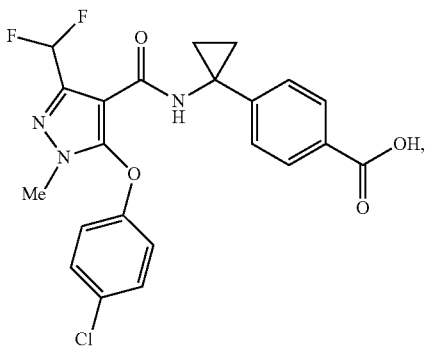
and pharmaceutically acceptable salts thereof.
11. The compound of embodiment 10, which is:
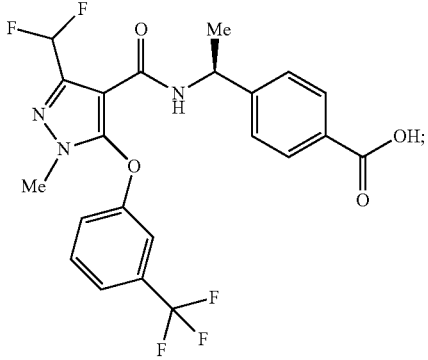 [SMILES: C[C@H](NC(=O)c1c(C(F)F)nn(C)c1Oc1cccc(C(F)(F)F)c1)c1ccc(C(=O)O)cc1]
or a pharmaceutically acceptable salt thereof.

12. The compound of embodiment 10, which is:

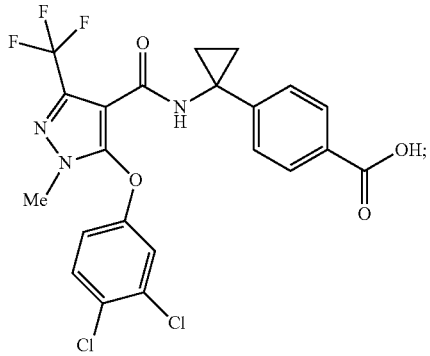 [SMILES: Cn1nc(C(F)(F)F)c(C(=O)NC2(c3ccc(C(=O)O)cc3)CC2)c1Oc1ccc(Cl)c(Cl)c1]

or a pharmaceutically acceptable salt thereof.

13. A pharmaceutical composition comprising a compound of formula I:

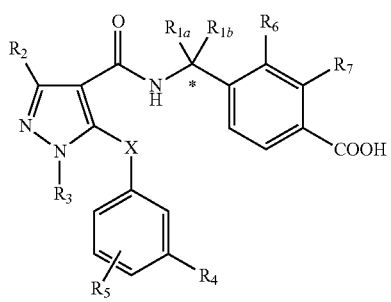

wherein:
one of $R_{1a}$ and $R_{1b}$ is hydrogen, and the other is methyl; or $R_{1a}$ and $R_{1b}$ are taken together to form a cyclopropyl ring;
$R_2$ is methyl or fluoromethyl;
$R_3$ is methyl;
$R_4$ is hydrogen, halo, fluoromethyl, methoxy, or fluoromethoxy;
$R_5$ is hydrogen, halo, fluoromethyl, methoxy, or fluoromethoxy;
$R_6$ is hydrogen, halo, methyl, or methoxy;
$R_7$ is hydrogen, halo, methyl, or methoxy; and
X is oxygen;
or a pharmaceutically acceptable salt thereof;
and a pharmaceutically acceptable carrier.

14. A pharmaceutical composition comprising a compound of embodiment 10, or
a pharmaceutically acceptable salt thereof;
and a pharmaceutically acceptable carrier.

15. A pharmaceutical composition comprising the compound which is:

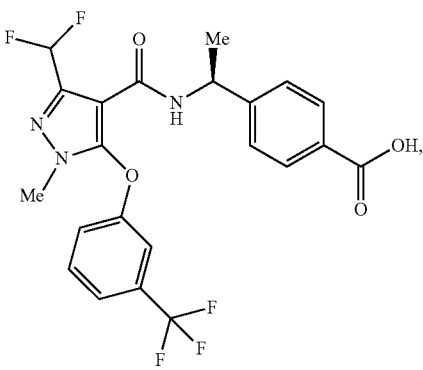 [SMILES: C[C@H](NC(=O)c1c(C(F)F)nn(C)c1Oc1cccc(C(F)(F)F)c1)c1ccc(C(=O)O)cc1]

or a pharmaceutically acceptable salt thereof;
and a pharmaceutically acceptable carrier.

16. A pharmaceutical composition comprising the compound which is:

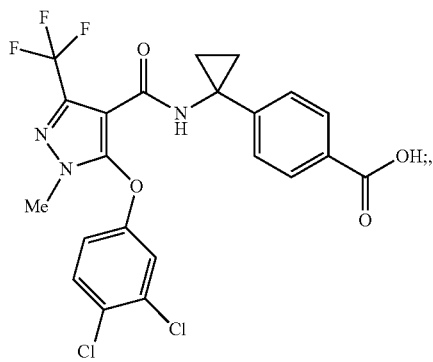

or a pharmaceutically acceptable salt thereof;
and a pharmaceutically acceptable carrier.

17. A method of treating multiple sclerosis in a mammal, comprising the step of administering to the mammal a pharmaceutical composition comprising a compound of formula I:

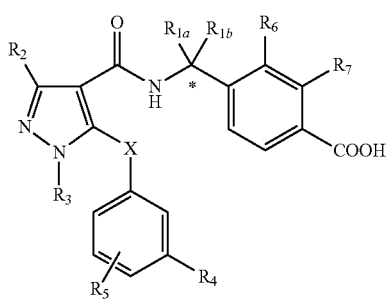

wherein:
one of $R_{1a}$ and $R_{1b}$ is hydrogen, and the other is methyl; or $R_{1a}$ and $R_{1b}$ are taken together to form a cyclopropyl ring;
$R_2$ is methyl or fluoromethyl;
$R_3$ is methyl;
$R_4$ is hydrogen, halo, fluoromethyl, methoxy, or fluoromethoxy;
$R_5$ is hydrogen, halo, fluoromethyl, methoxy, or fluoromethoxy;

R₆ is hydrogen, halo, methyl, or methoxy;
R₇ is hydrogen, halo, methyl, or methoxy; and
X is oxygen;
or pharmaceutically acceptable salts thereof.

18. A method of treating multiple sclerosis in a mammal, comprising the step of administering to the mammal a pharmaceutical composition comprising a compound of embodiment 10;
or a pharmaceutically acceptable salt thereof.

19. A method of treating multiple sclerosis in a mammal, comprising the step of administering to the mammal a pharmaceutical composition comprising the compound of Formula I which is:

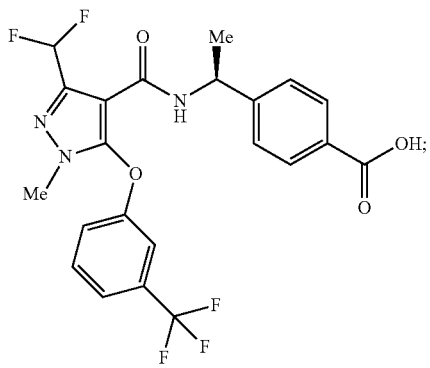 [SMILES: C[C@H](NC(=O)c1c(C(F)F)nn(C)c1Oc1cccc(C(F)(F)F)c1)c1ccc(C(=O)O)cc1]

or a pharmaceutical salt thereof.

20. A method of treating multiple sclerosis in a mammal, comprising the step of administering to the mammal a pharmaceutical composition comprising the compound of Formula I which is:

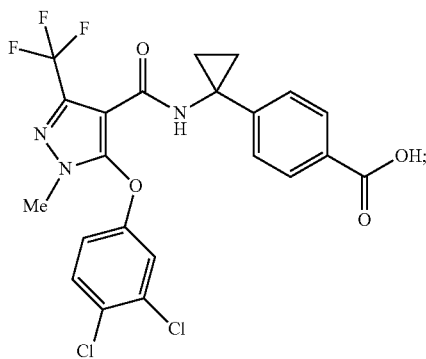 [SMILES: Cn1nc(C(F)(F)F)c(C(=O)NC2(c3ccc(C(=O)O)cc3)CC2)c1Oc1ccc(Cl)c(Cl)c1]

or a pharmaceutical salt thereof.

21. Use of a compound of embodiment 1 in the manufacture of a medicament for the treatment of multiple sclerosis.

22. A method of treating rheumatoid arthritis in a mammal, comprising the step of administering to the mammal a pharmaceutical composition comprising a compound of formula I:

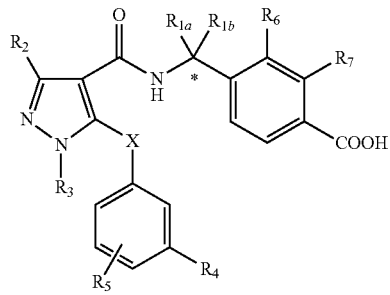

wherein:
one of $R_{1a}$ and $R_{1b}$ is hydrogen, and the other is methyl; or $R_{1a}$ and $R_{1b}$ are taken together to form a cyclopropyl ring;
$R_2$ is methyl or fluoromethyl;
$R_3$ is methyl;
$R_4$ is hydrogen, halo, fluoromethyl, methoxy, or fluoromethoxy;
$R_5$ is hydrogen, halo, fluoromethyl, methoxy, or fluoromethoxy;
$R_6$ is hydrogen, halo, methyl, or methoxy;
$R_7$ is hydrogen, halo, methyl, or methoxy; and
X is oxygen;
or pharmaceutically acceptable salts thereof.

23. A method of treating rheumatoid arthritis in a mammal, comprising the step of administering to the mammal a pharmaceutical composition comprising comprising a compound of embodiment 10;
or a pharmaceutically acceptable salt thereof.

24. A method of treating rheumatoid arthritis in a mammal, comprising the step of administering to the mammal a pharmaceutical composition comprising the compound of Formula I which is:

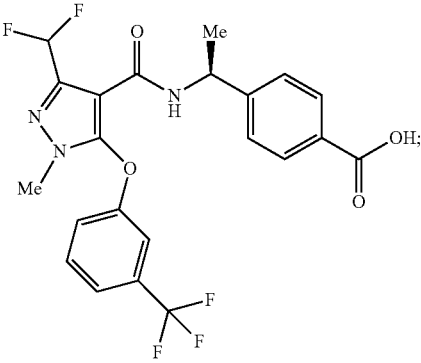 [SMILES: C[C@H](NC(=O)c1c(C(F)F)nn(C)c1Oc1cccc(C(F)(F)F)c1)c1ccc(C(=O)O)cc1]

or a pharmaceutically acceptable salt thereof.

25. A method of treating rheumatoid arthritis in a mammal, comprising the step of administering to the mammal a pharmaceutical composition comprising the compound of Formula I which is:

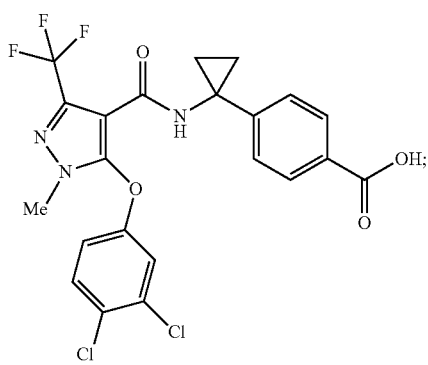 [SMILES: Cn1nc(C(F)(F)F)c(C(=O)NC2(c3ccc(C(=O)O)cc3)CC2)c1Oc1ccc(Cl)c(Cl)c1]

or a pharmaceutically acceptable salt thereof.

26. Use of a compound of embodiment 1 in the manufacture of a medicament for the treatment of rheumatoid arthritis.

27. A method of treating systemic lupus erythematosus in a mammal, comprising the step of administering to the mammal a pharmaceutical composition comprising a compound of formula I:

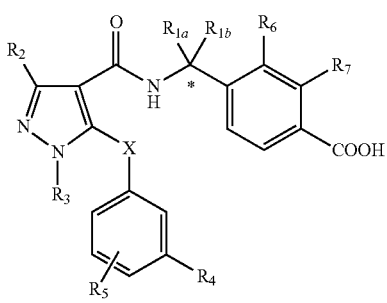

wherein:

one of $R_{1a}$ and $R_{1b}$ is hydrogen, and the other is methyl; or $R_{1a}$ and $R_{1b}$ are taken together to form a cyclopropyl ring;

$R_2$ is methyl or fluoromethyl;

$R_3$ is methyl;

$R_4$ is hydrogen, halo, fluoromethyl, methoxy, or fluoromethoxy;

$R_5$ is hydrogen, halo, fluoromethyl, methoxy, or fluoromethoxy;

$R_6$ is hydrogen, halo, methyl, or methoxy;

$R_7$ is hydrogen, halo, methyl, or methoxy; and

X is oxygen;

or pharmaceutically acceptable salts thereof.

28. A method of treating systemic lupus erythematosus in a mammal, comprising the step of administering to the mammal a pharmaceutical composition comprising a compound of embodiment 10, or a pharmaceutically acceptable salt thereof.

29. A method of treating systemic lupus erythematosus in a mammal, comprising the step of administering to a mammal a pharmaceutical composition comprising the compound of Formula I which is:

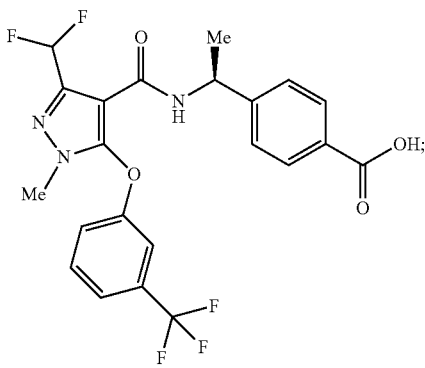 [SMILES: C[C@H](NC(=O)c1c(C(F)F)nn(C)c1Oc1cccc(C(F)(F)F)c1)c1ccc(C(=O)O)cc1]

or a pharmaceutically acceptable salt thereof.

30. A method of treating systemic lupus erythematosus in a mammal, comprising the step of administering to a mammal a pharmaceutical composition comprising the compound of Formula I which is:

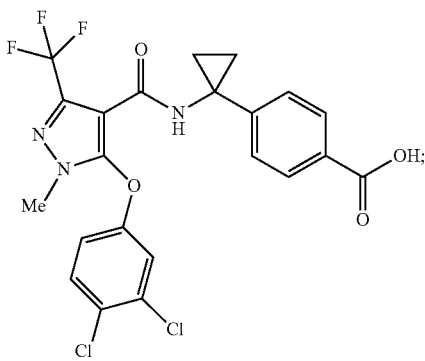 [SMILES: Cn1nc(C(F)(F)F)c(C(=O)NC2(c3ccc(C(=O)O)cc3)CC2)c1Oc1ccc(Cl)c(Cl)c1]

or a pharmaceutically acceptable salt thereof.

31. Use of a compound of embodiment 1 in the manufacture of a medicament for the treatment of systemic lupus erythematosus.

32. A method of treating type 1 diabetes in a mammal, comprising the step of administering to the mammal a pharmaceutical composition comprising a compound of formula I:

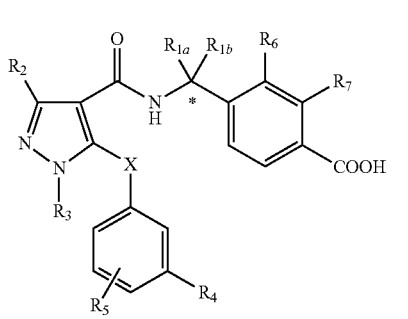

wherein:

one of $R_{1a}$ and $R_{1b}$ is hydrogen, and the other is methyl; or $R_{1a}$ and $R_{1b}$ are taken together to form a cyclopropyl ring;

$R_2$ is methyl or fluoromethyl;

$R_3$ is methyl;

$R_4$ is hydrogen, halo, fluoromethyl, methoxy, or fluoromethoxy;

R$_5$ is hydrogen, halo, fluoromethyl, methoxy, or fluoromethoxy;

R$_6$ is hydrogen, halo, methyl, or methoxy;

R$_7$ is hydrogen, halo, methyl, or methoxy; and

X is oxygen;

or pharmaceutically acceptable salts thereof.

33. A method of treating type 1 diabetes in a mammal, comprising the step of administering to the mammal a pharmaceutical composition comprising a compound of embodiment 10;

or a pharmaceutically acceptable salt thereof.

34. A method of treating type 1 diabetes in a mammal, comprising the step of administering to the mammal a pharmaceutical composition comprising the compound of Formula I which is:

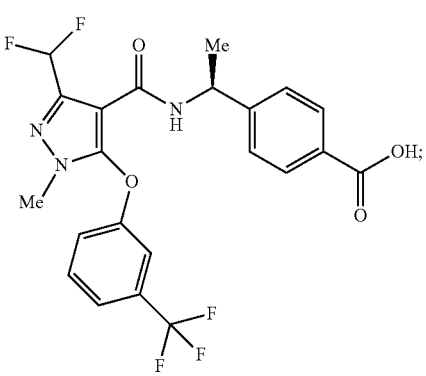 [SMILES: C[C@H](NC(=O)c1c(C(F)F)nn(C)c1Oc1cccc(C(F)(F)F)c1)c1ccc(C(=O)O)cc1]

or a pharmaceutically acceptable salt thereof.

35. A method of treating type 1 diabetes in a mammal, comprising the step of administering to the mammal a pharmaceutical composition comprising the compound of Formula I which is:

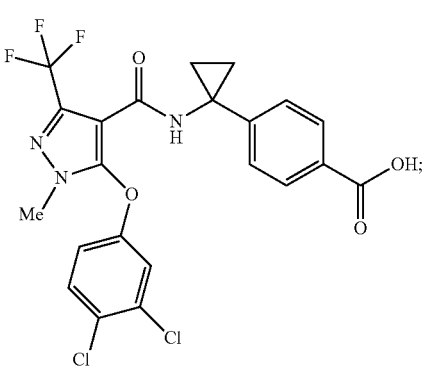 [SMILES: Cn1nc(C(F)(F)F)c(C(=O)NC2(c3ccc(C(=O)O)cc3)CC2)c1Oc1ccc(Cl)c(Cl)c1]

or a pharmaceutically acceptable salt thereof.

36. Use of a compound of embodiment 1 in the manufacture of a medicament for the treatment of type 1 diabetes.

37. A method of treating psoriasis in a mammal, comprising the step of administering to the mammal a pharmaceutical composition comprising a compound of Formula I:

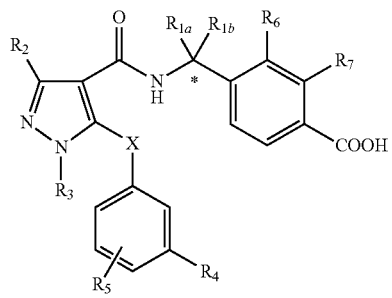

wherein:

one of R$_{1a}$ and R$_{1b}$ is hydrogen, and the other is methyl; or R$_{1a}$ and R$_{1b}$ are taken together to form a cyclopropyl ring;

R$_2$ is methyl or fluoromethyl;

R$_3$ is methyl;

R$_4$ is hydrogen, halo, fluoromethyl, methoxy, or fluoromethoxy;

R$_5$ is hydrogen, halo, fluoromethyl, methoxy, or fluoromethoxy;

R$_6$ is hydrogen, halo, methyl, or methoxy;

R$_7$ is hydrogen, halo, methyl, or methoxy; and

X is oxygen;

or pharmaceutically acceptable salts thereof.

38. A method of treating psoriasis in a mammal, comprising the step of administering to the mammal a pharmaceutical composition comprising a compound of embodiment 10;

or a pharmaceutically acceptable salt thereof.

39. A method of treating psoriasis in a mammal, comprising the step of administering to the mammal a pharmaceutical composition comprising the compound of Formula I which is:

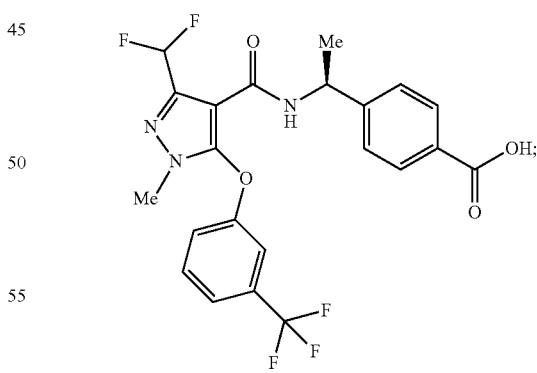

or a pharmaceutically acceptable salt thereof.

40. A method of treating psoriasis in a mammal, comprising the step of administering to the mammal a pharmaceutical composition comprising the compound of Formula I which is:

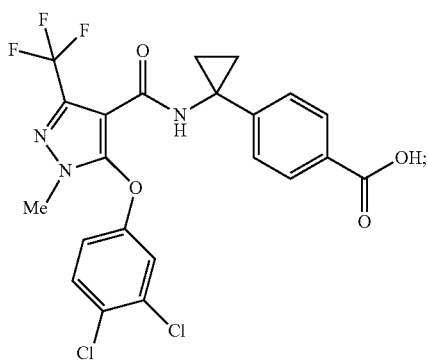 [SMILES: Cn1nc(C(F)(F)F)c(C(=O)NC2(c3ccc(C(=O)O)cc3)CC2)c1Oc1ccc(Cl)c(Cl)c1]

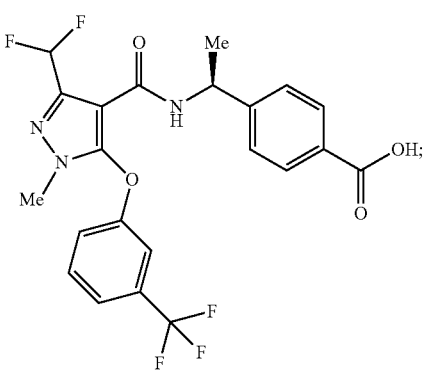 [SMILES: C[C@H](NC(=O)c1c(C(F)F)nn(C)c1Oc1cccc(C(F)(F)F)c1)c1ccc(C(=O)O)cc1]

or a pharmaceutically acceptable salt thereof.

41. Use of a compound of embodiment 1 in the manufacture of a medicament for the treatment of psoriasis.

42. A method of treating atherosclerosis in a mammal, comprising the step of administering to the mammal a pharmaceutical composition comprising a compound of Formula I:

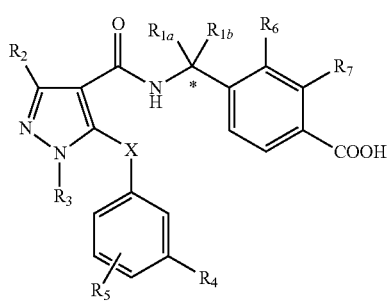

wherein:

one of $R_{1a}$ and $R_{1b}$ is hydrogen, and the other is methyl; or $R_{1a}$ and $R_{1b}$ are taken together to form a cyclopropyl ring;

$R_2$ is methyl or fluoromethyl;

$R_3$ is methyl;

$R_4$ is hydrogen, halo, fluoromethyl, methoxy, or fluoromethoxy;

$R_5$ is hydrogen, halo, fluoromethyl, methoxy, or fluoromethoxy;

$R_6$ is hydrogen, halo, methyl, or methoxy;

$R_7$ is hydrogen, halo, methyl, or methoxy; and

X is oxygen;

or pharmaceutically acceptable salts thereof.

43. A method of treating atherosclerosis in a mammal, comprising the step of administering to the mammal a pharmaceutical composition comprising a compound of embodiment 10;

or a pharmaceutically acceptable salt thereof.

44. A method of treating atherosclerosis in a mammal, comprising the step of administering to the mammal a pharmaceutical composition comprising the compound of Formula I which is:

or a pharmaceutically acceptable salt thereof

45. A method of treating atherosclerosis in a mammal, comprising the step of administering to the mammal a pharmaceutical composition comprising the compound of Formula I which is:

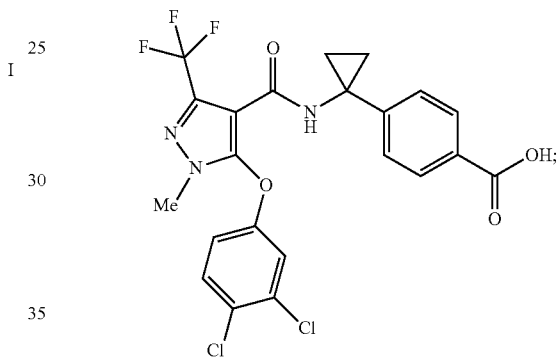

or a pharmaceutically acceptable salt thereof.

46. Use of a compound of embodiment 1 in the manufacture of a medicament for the treatment of atherosclerosis.

47. A method of treating inflammatory pain in a mammal, comprising the step of administering to the mammal a pharmaceutical composition comprising a compound of Formula I:

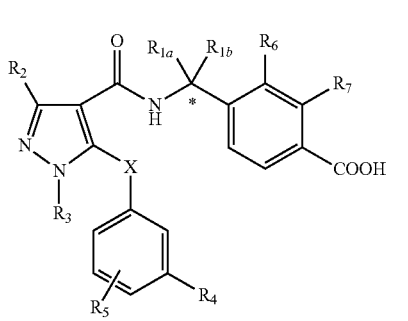

wherein:

one of $R_{1a}$ and $R_{1b}$ is hydrogen, and the other is methyl; or $R_{1a}$ and $R_{1b}$ are taken together to form a cyclopropyl ring;

$R_2$ is methyl or fluoromethyl;

$R_3$ is methyl;

$R_4$ is hydrogen, halo, fluoromethyl, methoxy, or fluoromethoxy;

$R_5$ is hydrogen, halo, fluoromethyl, methoxy, or fluoromethoxy;

$R_6$ is hydrogen, halo, methyl, or methoxy;

$R_7$ is hydrogen, halo, methyl, or methoxy; and

X is oxygen;

or pharmaceutically acceptable salts thereof.

48. A method of treating inflammatory pain in a mammal, comprising the step of administering to the mammal a pharmaceutical composition comprising a compound of embodiment 10;

or a pharmaceutically acceptable salt thereof.

49. A method of treating inflammatory pain in a mammal, comprising the step of administering to the mammal a pharmaceutical composition comprising the compound of Formula I which is:

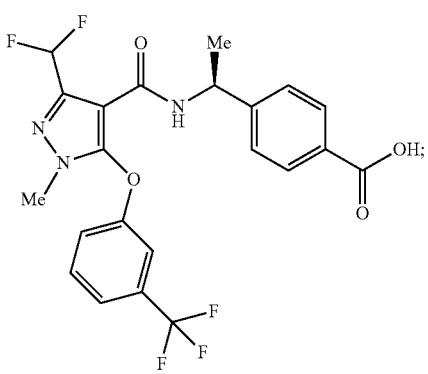 [SMILES: C[C@H](NC(=O)c1c(C(F)F)nn(C)c1Oc1cccc(C(F)(F)F)c1)c1ccc(C(=O)O)cc1]

or a pharmaceutically acceptable salt thereof.

50. A method of treating inflammatory pain in a mammal, comprising the step of administering to the mammal a pharmaceutical composition comprising the compound of Formula I which is:

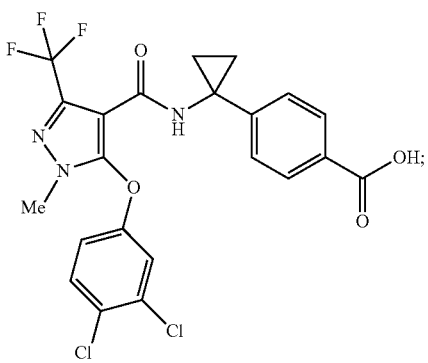 [SMILES: Cn1nc(C(F)(F)F)c(C(=O)NC2(c3ccc(C(=O)O)cc3)CC2)c1Oc1ccc(Cl)c(Cl)c1]

or a pharmaceutically acceptable salt thereof.

51. Use of a compound of embodiment 1 in the manufacture of a medicament for the treatment of inflammatory pain.

52. A method of treating neuropathic pain in a mammal, comprising the step of administering to the mammal a pharmaceutical composition comprising a compound of Formula I:

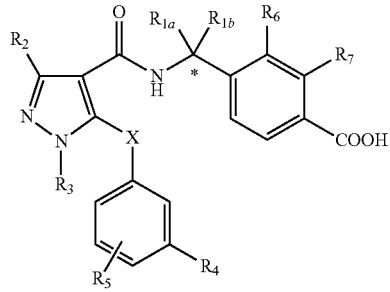

wherein:

one of $R_{1a}$ and $R_{1b}$ is hydrogen, and the other is methyl; or $R_{1a}$ and $R_{1b}$ are taken together to form a cyclopropyl ring;

$R_2$ is methyl or fluoromethyl;

$R_3$ is methyl;

$R_4$ is hydrogen, halo, fluoromethyl, methoxy, or fluoromethoxy;

$R_5$ is hydrogen, halo, fluoromethyl, methoxy, or fluoromethoxy;

$R_6$ is hydrogen, halo, methyl, or methoxy;

$R_7$ is hydrogen, halo, methyl, or methoxy; and

X is oxygen;

or pharmaceutically acceptable salts thereof.

53. A method of treating neuropathic pain in a mammal, comprising the step of administering to the mammal a pharmaceutical composition comprising a compound of embodiment 10;

or a pharmaceutically acceptable salt thereof.

54. A method of treating neuropathic pain in a mammal, comprising the step of administering to the mammal a pharmaceutical composition comprising the compound of Formula I which is:

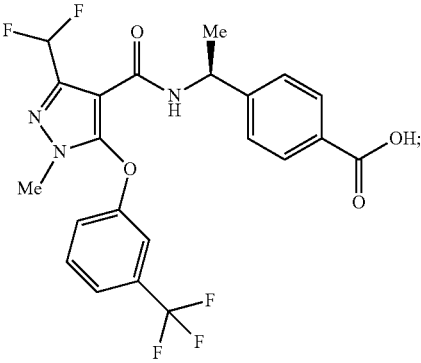 [SMILES: C[C@H](NC(=O)c1c(C(F)F)nn(C)c1Oc1cccc(C(F)(F)F)c1)c1ccc(C(=O)O)cc1]

or a pharmaceutically acceptable salt thereof.

55. A method of treating neuropathic pain in a mammal, comprising the step of administering to the mammal a pharmaceutical composition comprising the compound of Formula I which is:

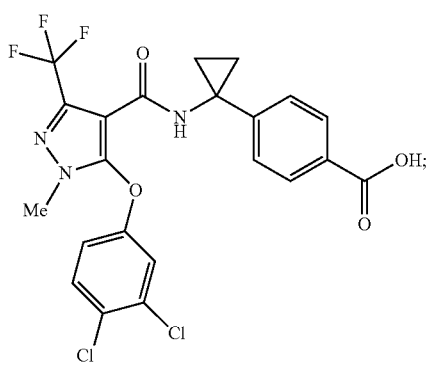 [SMILES: Cn1nc(C(F)(F)F)c(C(=O)NC2(c3ccc(C(=O)O)cc3)CC2)c1Oc1ccc(Cl)c(Cl)c1]

or a pharmaceutically acceptable salt thereof.

56. Use of a compound of embodiment 1 in the manufacture of a medicament for the treatment of neuropathic pain.

57. A method of treating migraine-associated pain in a mammal, comprising the step of administering to the mammal a pharmaceutical composition comprising a compound of Formula I:

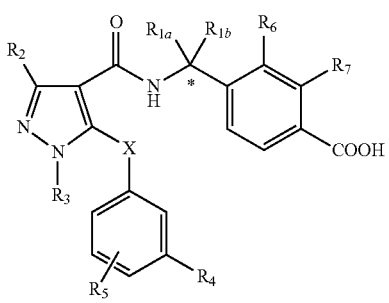

wherein:

one of $R_{1a}$ and $R_{1b}$ is hydrogen, and the other is methyl; or $R_{1a}$ and $R_{1b}$ are taken together to form a cyclopropyl ring;

$R_2$ is methyl or fluoromethyl;

$R_3$ is methyl;

$R_4$ is hydrogen, halo, fluoromethyl, methoxy, or fluoromethoxy;

$R_5$ is hydrogen, halo, fluoromethyl, methoxy, or fluoromethoxy;

$R_6$ is hydrogen, halo, methyl, or methoxy;

$R_7$ is hydrogen, halo, methyl, or methoxy; and

X is oxygen;

or pharmaceutically acceptable salts thereof.

58. A method of treating migraine-associated pain in a mammal, comprising the step of administering to the mammal a pharmaceutical composition comprising a compound of embodiment 10;

or a pharmaceutically acceptable salt thereof

59. A method of treating migraine-associated pain in a mammal, comprising the step of administering to the mammal a pharmaceutical composition comprising the compound of Formula I which is:

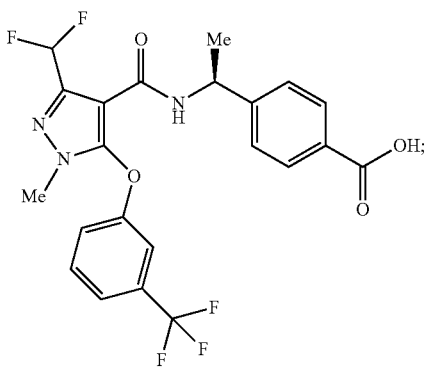 [SMILES: C[C@H](NC(=O)c1c(C(F)F)nn(C)c1Oc1cccc(C(F)(F)F)c1)c1ccc(C(=O)O)cc1]

or a pharmaceutically acceptable salt thereof.

60. A method of treating migraine-associated pain in a mammal, comprising the step of administering to the mammal a pharmaceutical composition comprising the compound of Formula I which is:

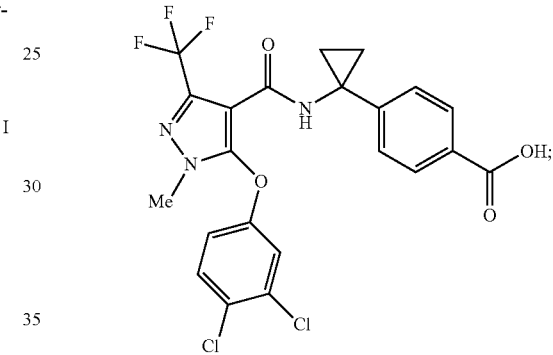

or a pharmaceutically acceptable salt thereof.

61. Use of a compound of embodiment 1 in the manufacture of a medicament for the treatment of migraine-associated pain.

62. A method of treating spondyloarthropathies in a mammal, comprising the step of administering to the mammal a pharmaceutical composition comprising a compound of formula I:

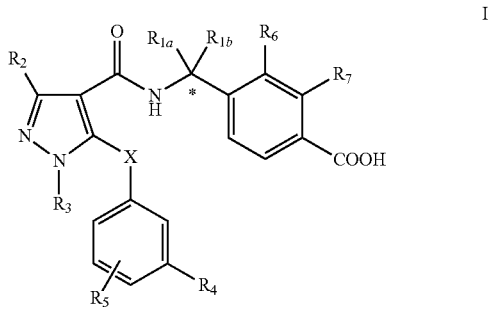

wherein:

one of $R_{1a}$ and $R_{1b}$ is hydrogen, and the other is methyl; or $R_{1a}$ and $R_{1b}$ are taken together to form a cyclopropyl ring;

$R_2$ is methyl or fluoromethyl;

$R_3$ is methyl;

$R_4$ is hydrogen, halo, fluoromethyl, methoxy, or fluoromethoxy;

R$_5$ is hydrogen, halo, fluoromethyl, methoxy, or fluoromethoxy;

R$_6$ is hydrogen, halo, methyl, or methoxy;

R$_7$ is hydrogen, halo, methyl, or methoxy; and

X is oxygen;

or pharmaceutically acceptable salts thereof.

63. A method of treating spondyloarthropathies in a mammal, comprising the step of administering to the mammal a pharmaceutical composition comprising a compound of embodiment 10;

or a pharmaceutically acceptable salt thereof.

64. A method of treating spondyloarthropathies in a mammal, comprising the step of administering to the mammal a pharmaceutical composition comprising the compound of Formula I which is:

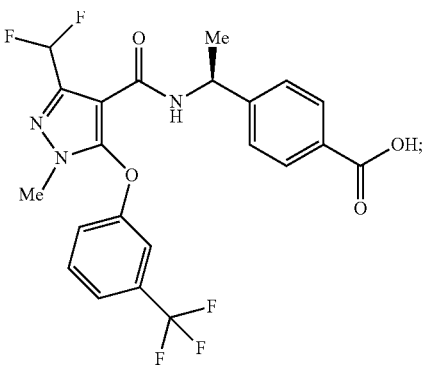

or a pharmaceutically acceptable salt thereof.

65. A method of treating spondyloarthropathies in a mammal, comprising the step of administering to the mammal a pharmaceutical composition comprising the compound of Formula I which is:

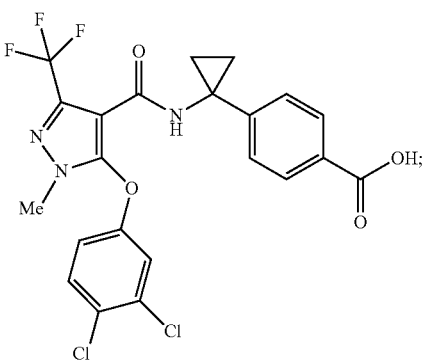 [SMILES: Cn1nc(C(F)(F)F)c(C(=O)NC2(c3ccc(C(=O)O)cc3)CC2)c1Oc1ccc(Cl)c(Cl)c1]

or a pharmaceutically acceptable salt thereof.

66. Use of a compound of embodiment 1 in the manufacture of a medicament for the treatment of spondyloarthropathies.

67. A method of treating cancer in a mammal, comprising the step of administering to the mammal a pharmaceutical composition comprising a compound of formula I:

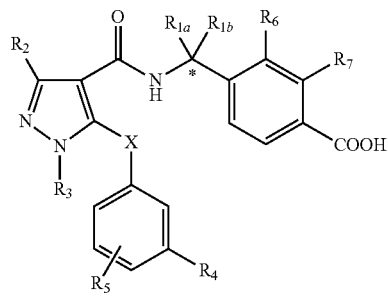

wherein:

one of R$_{1a}$ and R$_{1b}$ is hydrogen, and the other is methyl; or R$_{1a}$ and R$_{1b}$ are taken together to form a cyclopropyl ring;

R$_2$ is methyl or fluoromethyl;

R$_3$ is methyl;

R$_4$ is hydrogen, halo, fluoromethyl, methoxy, or fluoromethoxy;

R$_5$ is hydrogen, halo, fluoromethyl, methoxy, or fluoromethoxy;

R$_6$ is hydrogen, halo, methyl, or methoxy;

R$_7$ is hydrogen, halo, methyl, or methoxy; and

X is oxygen;

or pharmaceutically acceptable salts thereof.

68. A method of treating cancer in a mammal, comprising the step of administering to the mammal a pharmaceutical composition comprising comprising a compound of embodiment 10;

or a pharmaceutically acceptable salt thereof.

69. A method of treating cancer in a mammal, comprising the step of administering to the mammal a pharmaceutical composition comprising the compound of Formula I which is:

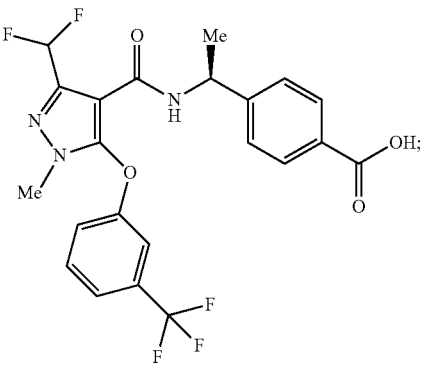 [SMILES: C[C@H](NC(=O)c1c(C(F)F)nn(C)c1Oc1cccc(C(F)(F)F)c1)c1ccc(C(=O)O)cc1]

or a pharmaceutically acceptable salt thereof.

70. A method of treating cancer in a mammal, comprising the step of administering to the mammal a pharmaceutical composition comprising the compound of Formula I which is:

119

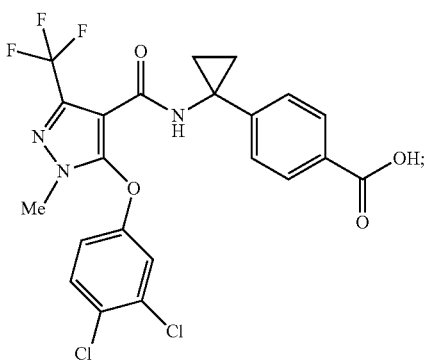

or a pharmaceutically acceptable salt thereof.

71. Use of a compound of embodiment 1 in the manufacture of a medicament for the treatment of cancer.

72. The method of any of embodiments 67-71, wherein the cancer is selected from the group consisting of skin cancer, breast cancer, colorectal cancer, prostate cancer, kidney cancer, ovarian cancer, cervical cancer, endometrial cancer, glioblastoma, lung cancer, head and neck cancer, medulloblastoma, and urinary tract cancer.

73. The method of embodiment 72, wherein the cancer is skin cancer.

74. The method of embodiment 72, wherein the cancer is breast cancer.

75. The method of embodiment 72, wherein the cancer is colorectal cancer.

76. The method of embodiment 72, wherein the cancer is prostate cancer.

77. The method of embodiment 72, wherein the cancer is kidney cancer.

78. The method of embodiment 72, wherein the cancer is ovarian cancer.

79. The method of embodiment 72, wherein the cancer is cervical cancer.

80. The method of embodiment 72, wherein the cancer is endometrial cancer.

81. The method of embodiment 72, wherein the cancer is glioblastoma.

82. The method of embodiment 72, wherein the cancer is lung cancer.

83. The method of embodiment 72, wherein the cancer is head and neck cancer.

84. The method of embodiment 72, wherein the cancer is medulloblastoma.

85. The method of embodiment 72, wherein the cancer is urinary tract cancer.

Other Embodiments

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

120

We claim:
1. A compound of formula I:

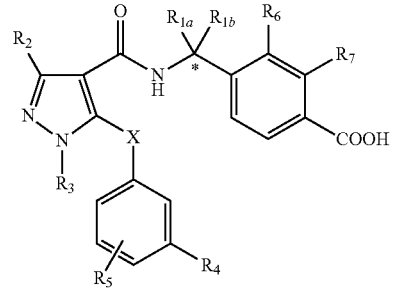

wherein:
one of $R_{1a}$ and $R_{1b}$ is hydrogen, and the other is methyl; or $R_{1a}$ and $R_{1b}$ are taken together to form a cyclopropyl ring;
$R_2$ is methyl or fluoromethyl;
$R_3$ is methyl;
$R_4$ is hydrogen, halo, methyl, fluoromethyl, methoxy, or fluoromethoxy;
$R_5$ is hydrogen, halo, methyl, fluoromethyl, methoxy, or fluoromethoxy;
$R_6$ is hydrogen, halo, methyl, or methoxy;
$R_7$ is hydrogen, halo, methyl, or methoxy; and
X is oxygen;
or a pharmaceutically acceptable salt thereof.

2. The compound of claim 1, wherein:
one of $R_{1a}$ and $R_{1b}$ is hydrogen, and the other is methyl; $R_2$ is methyl, difluoromethyl, or trifluoromethyl;
$R_3$ is methyl;
$R_4$ is chloro, fluoro, trifluoromethyl, difluoromethyl, methyl, methoxy, difluoromethoxy, or trifluoromethoxy;
$R_5$ is hydrogen, chloro, fluoro, methyl, or methoxy; and
$R_6$ and $R_7$ are hydrogen;
or a pharmaceutically acceptable salt thereof.

3. The compound of claim 2, wherein $R_5$ is hydrogen; or a pharmaceutically acceptable salt thereof.

4. The compound of claim 3, wherein $R_4$ is selected from chloro, trifluoromethyl, difluoromethyl, difluoromethoxy, and trifluoromethoxy; or a pharmaceutically acceptable salt thereof.

5. The compound of claim 1, wherein:
one of $R_{1a}$ and $R_{1b}$ is hydrogen, and the other is methyl, and the compound of Formula I is a mixture of stereoisomers;
or a pharmaceutically acceptable salt thereof.

6. The compound of claim 1, wherein:
one of $R_{1a}$ and $R_{1b}$ is hydrogen, and the other is methyl, and the compound of Formula I is a substantially pure stereoisomer;
or a pharmaceutically acceptable salt thereof.

7. The compound of claim 6, wherein:
the carbon of the compound of Formula I marked with an * has substantially the S-configuration;
or a pharmaceutically acceptable salt thereof.

8. The compound of claim 6, wherein:
the carbon of the compound of Formula I marked with an * has substantially the R-configuration;
or a pharmaceutically acceptable salt thereof.

9. The compound of claim 1, wherein $R_1$ and $R_{1b}$ are taken together to form a cyclopropyl ring;

$R_2$ is methyl, trifluoromethyl, or difluoromethyl;

$R_3$ is methyl;

$R_4$ is trifluoromethyl, difluoromethyl, chloro, or fluoro; and $R_6$ and $R_7$ are hydrogen;

or a pharmaceutically acceptable salt thereof.

10. The compound of claim 1, wherein said compound is selected from the group consisting of:

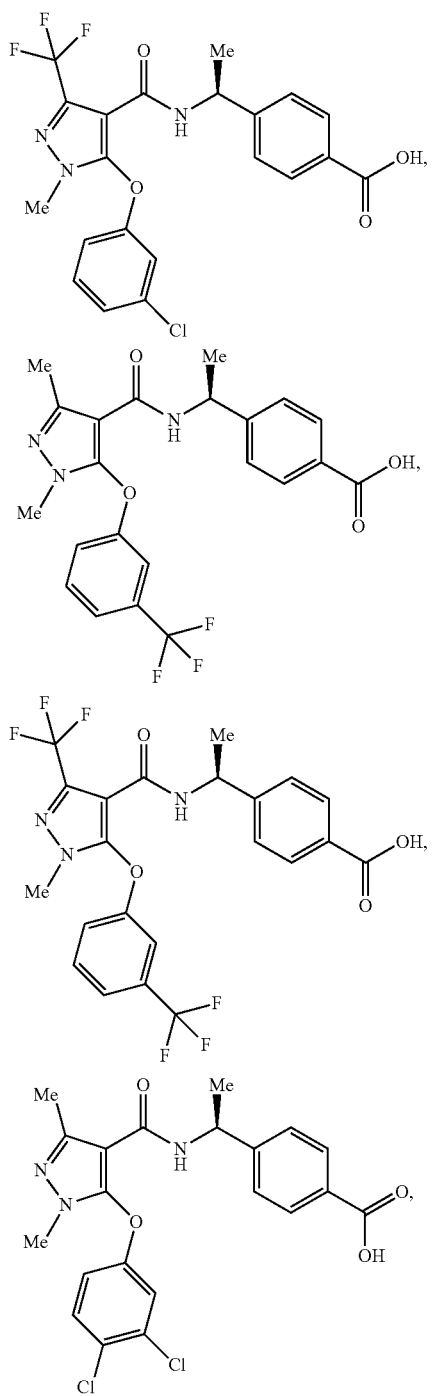

-continued

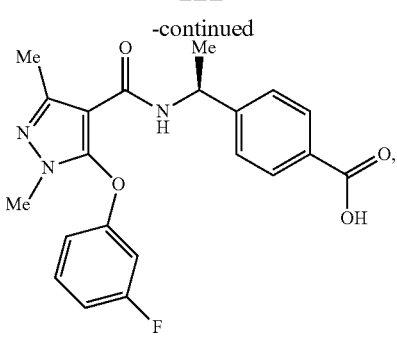

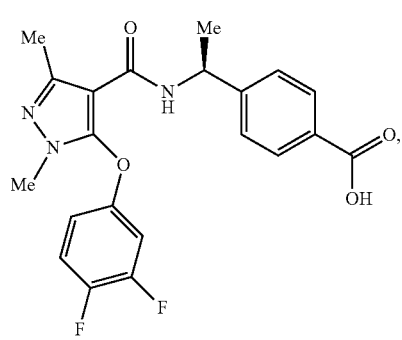

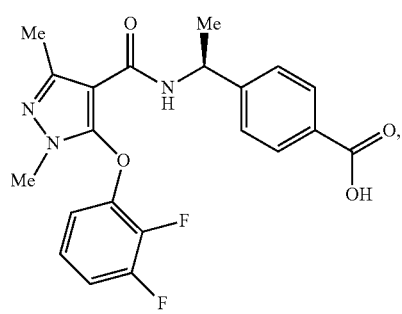

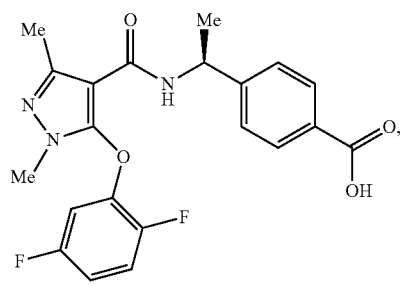

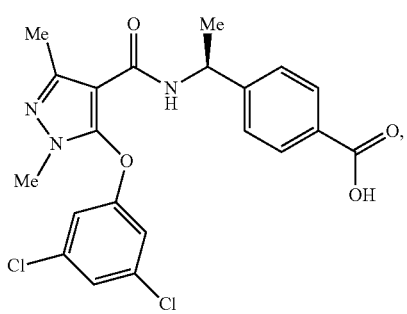

123
-continued
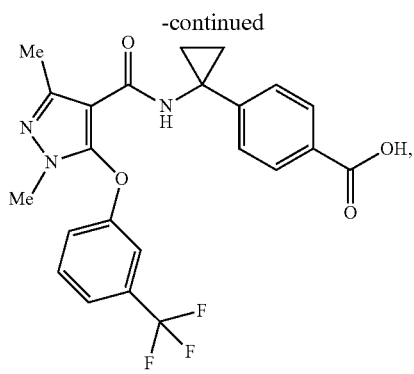
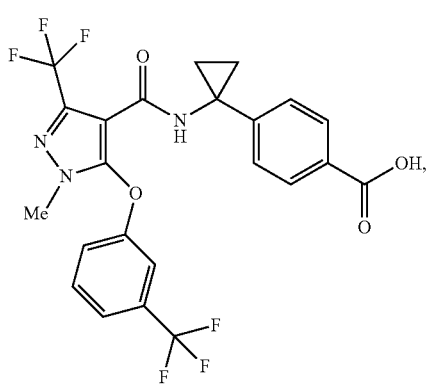
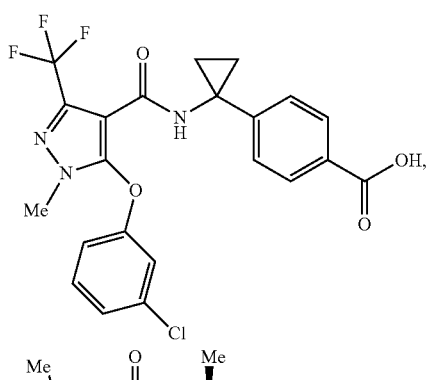
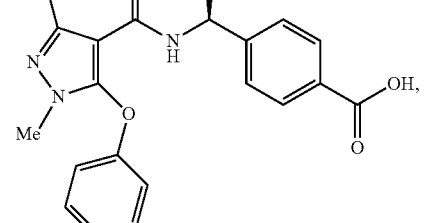
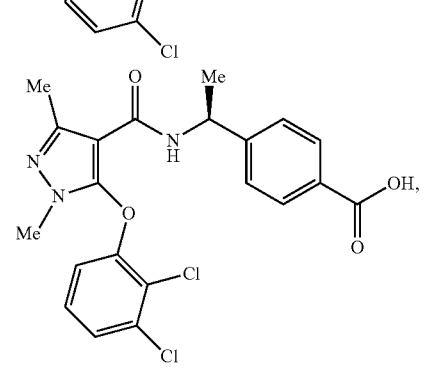
124
-continued
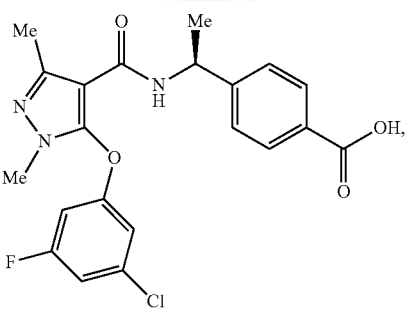
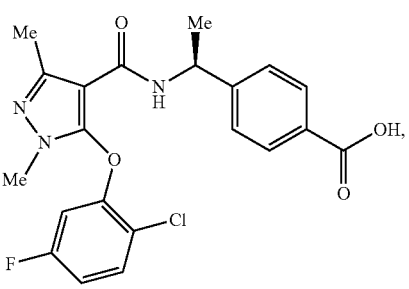
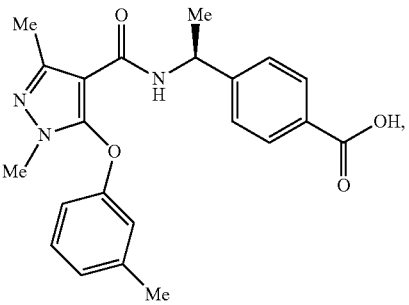
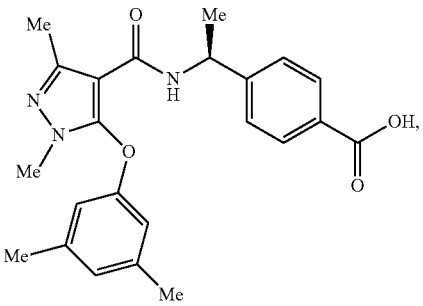
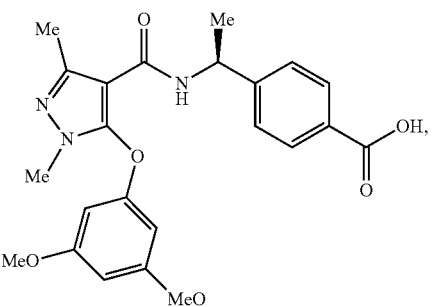

125
-continued
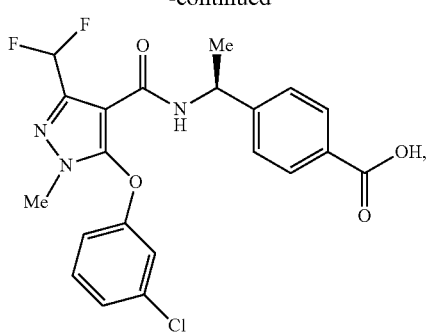
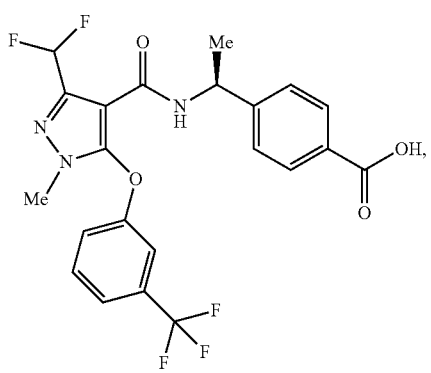 [SMILES: C[C@H](NC(=O)c1c(C(F)F)nn(C)c1Oc1cccc(C(F)(F)F)c1)c1ccc(C(=O)O)cc1]
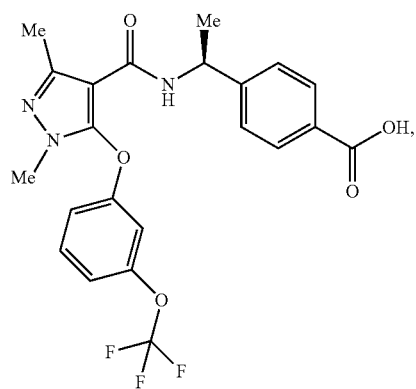
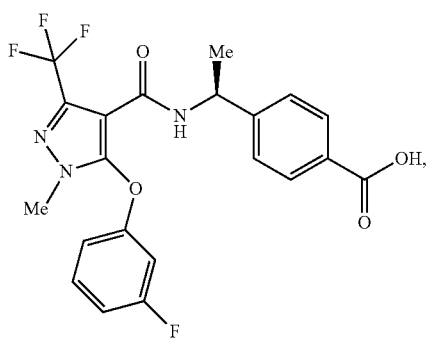
126
-continued
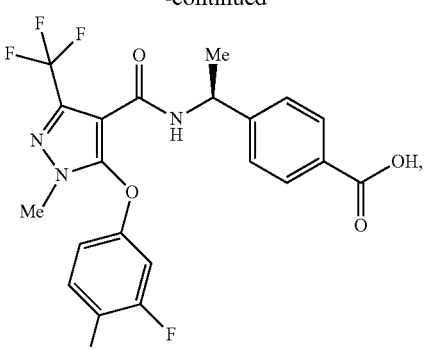
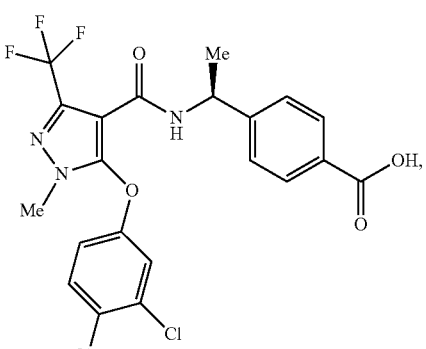
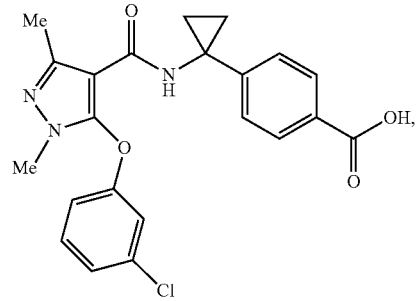
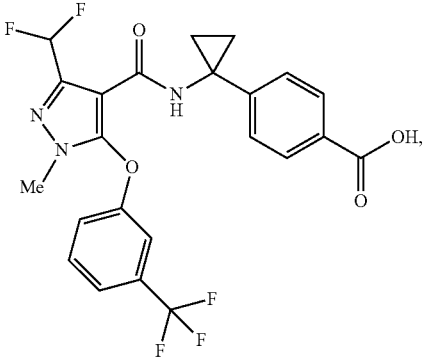
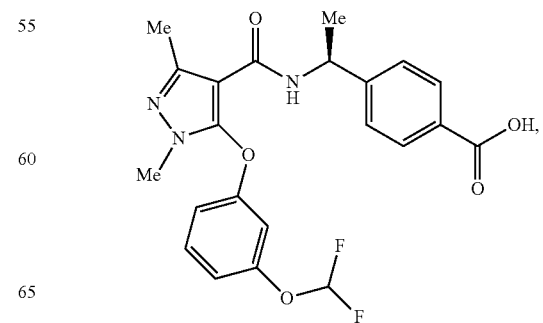

127
-continued
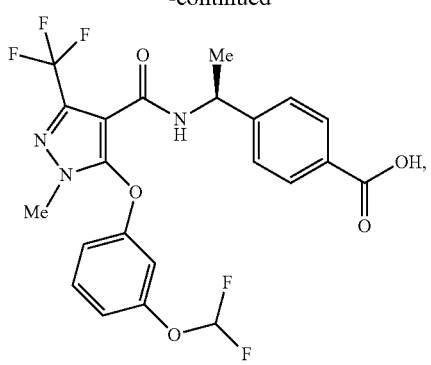
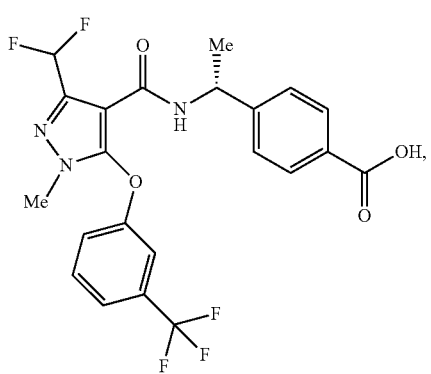
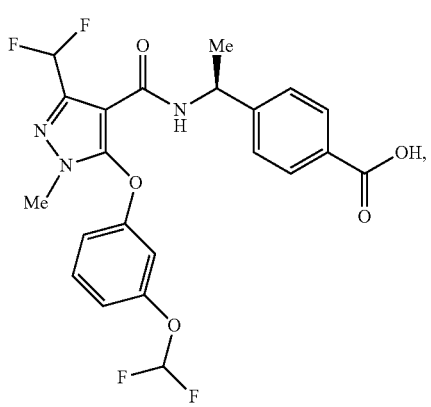
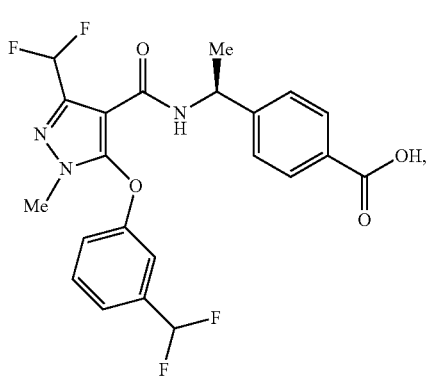
128
-continued
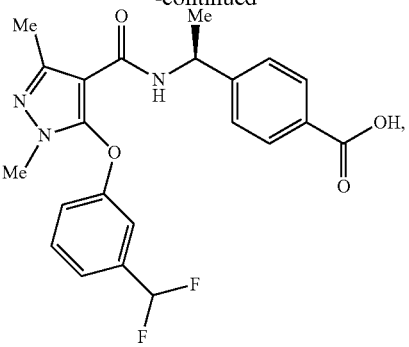
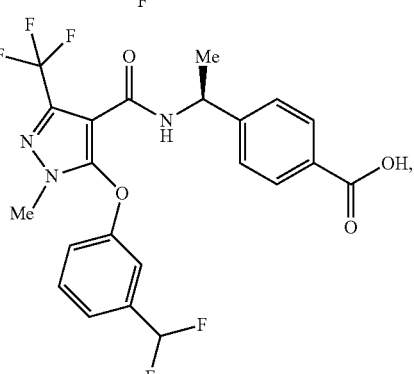
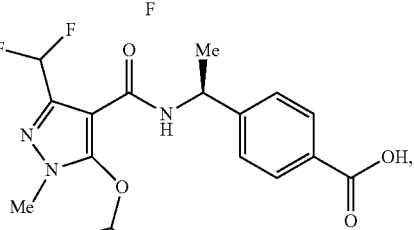
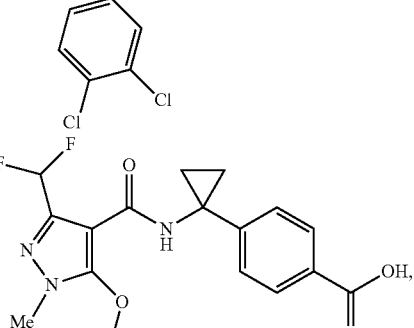
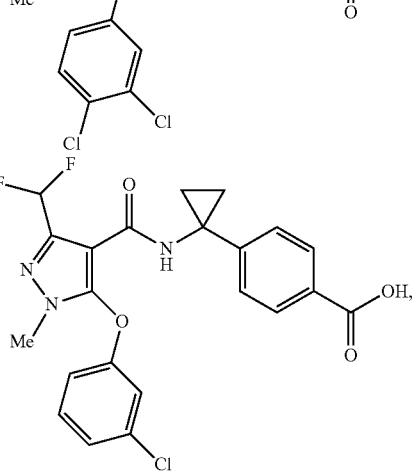

129
-continued
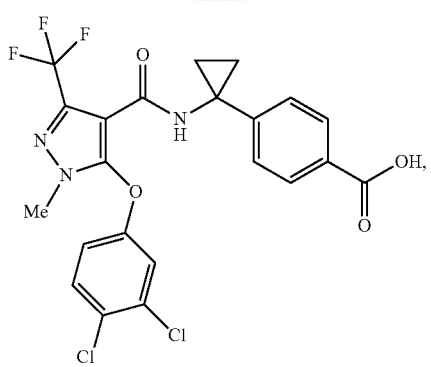 [SMILES: Cn1nc(C(F)(F)F)c(C(=O)NC2(c3ccc(C(=O)O)cc3)CC2)c1Oc1ccc(Cl)c(Cl)c1]
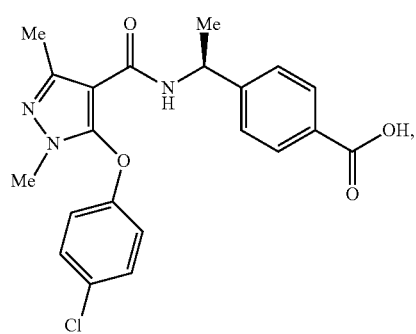
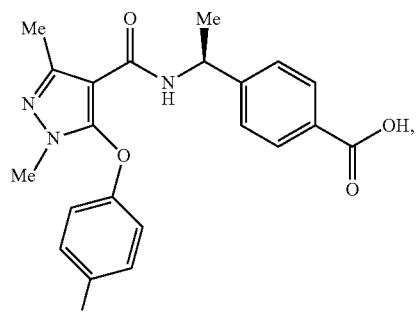
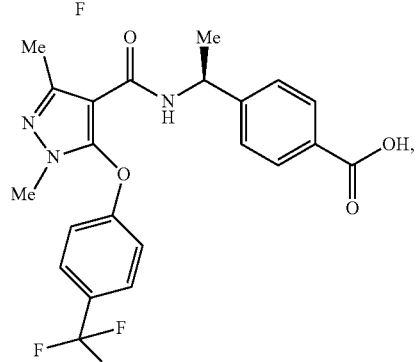
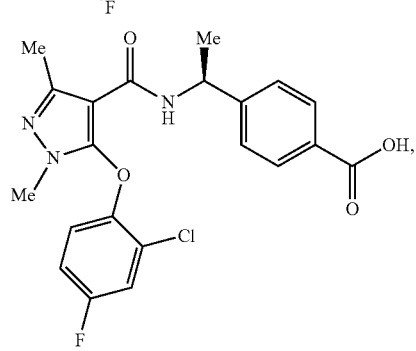
130
-continued
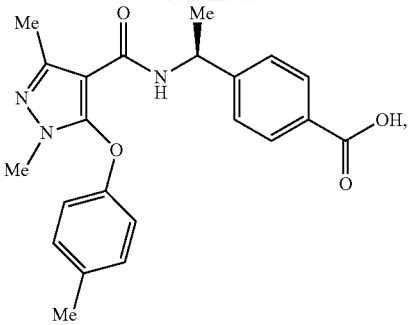
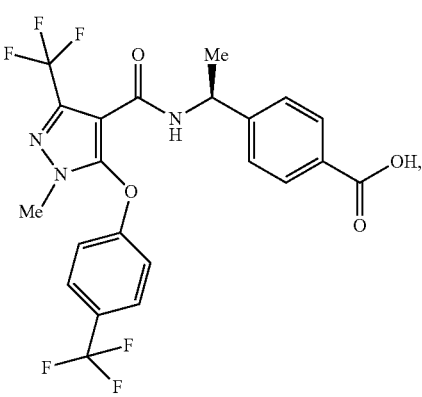
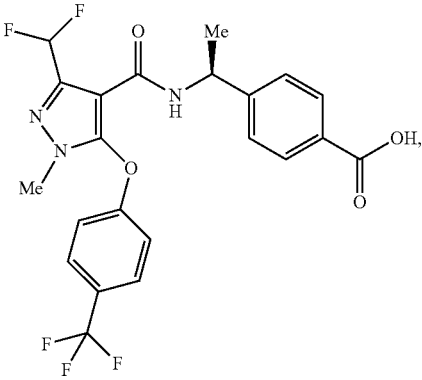
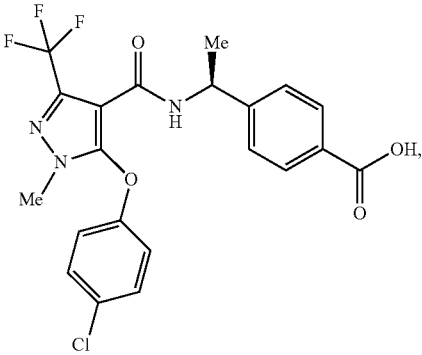

-continued
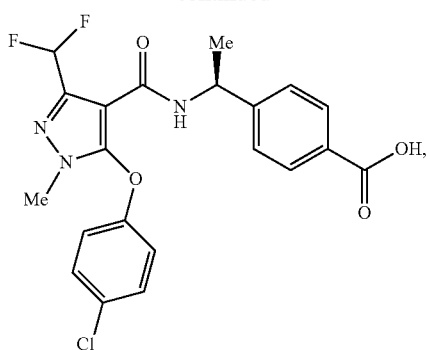
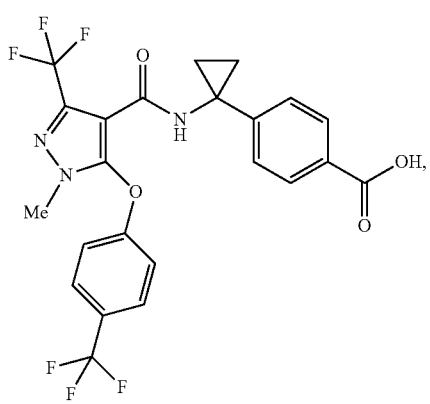
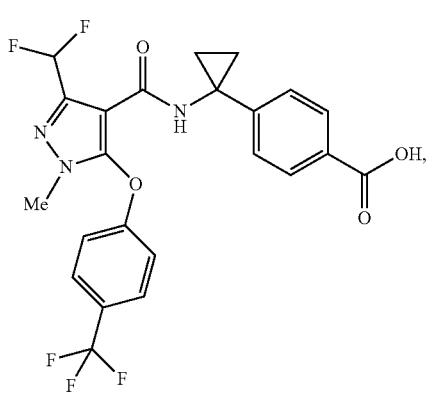
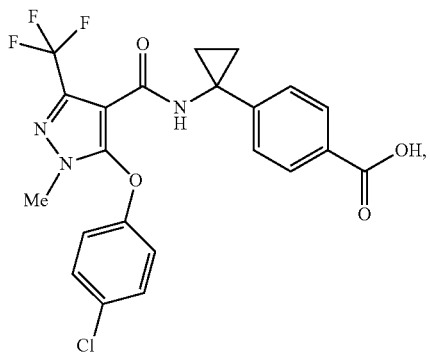
-continued
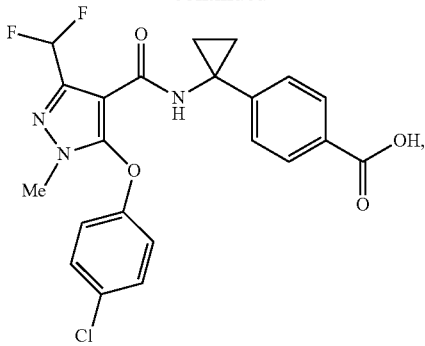
and pharmaceutically acceptable salts thereof.
11. The compound of claim 1, wherein said compound is:
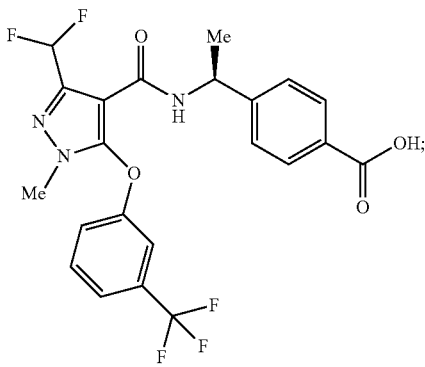 [SMILES: C[C@H](NC(=O)c1c(C(F)F)nn(C)c1Oc1cccc(C(F)(F)F)c1)c1ccc(C(=O)O)cc1]
or a pharmaceutically acceptable salt thereof.
12. The compound of claim 1, wherein said compound is:
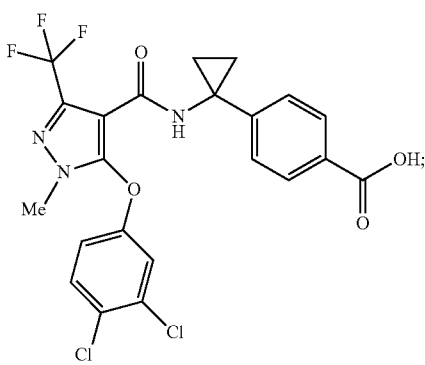 [SMILES: Cn1nc(C(F)(F)F)c(C(=O)NC2(c3ccc(C(=O)O)cc3)CC2)c1Oc1ccc(Cl)c(Cl)c1]
or a pharmaceutically acceptable salt thereof.
13. A pharmaceutical composition comprising a compound of formula I:

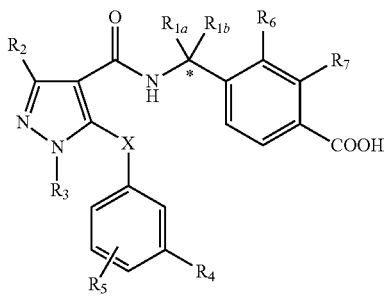

wherein:
- one of $R_{1a}$ and $R_{1b}$ is hydrogen, and the other is methyl; or $R_{1a}$ and $R_{1b}$ are taken together to form a cyclopropyl ring;
- $R_2$ is methyl or fluoromethyl;
- $R_3$ is methyl;
- $R_4$ is hydrogen, halo, methyl, fluoromethyl, methoxy, or fluoromethoxy;
- $R_5$ is hydrogen, halo, methyl, fluoromethyl, methoxy, or fluoromethoxy;
- $R_6$ is hydrogen, halo, methyl, or methoxy;
- $R_7$ is hydrogen, halo, methyl, or methoxy; and
- X is oxygen;

or a pharmaceutically acceptable salt thereof;
and a pharmaceutically acceptable carrier.

14. A pharmaceutical composition comprising a compound of claim 10, or a pharmaceutically acceptable salt thereof;
and a pharmaceutically acceptable carrier.

15. A pharmaceutical composition comprising a compound:

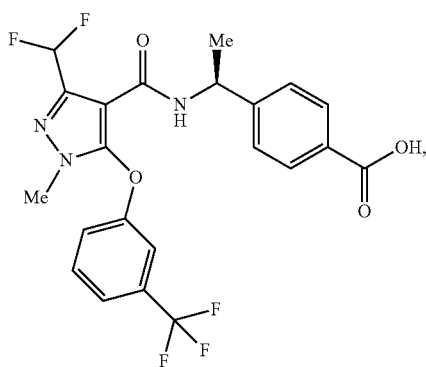 [SMILES: C[C@H](NC(=O)c1c(C(F)F)nn(C)c1Oc1cccc(C(F)(F)F)c1)c1ccc(C(=O)O)cc1]

or a pharmaceutically acceptable salt thereof;
and a pharmaceutically acceptable carrier.

16. A pharmaceutical composition comprising a compound:

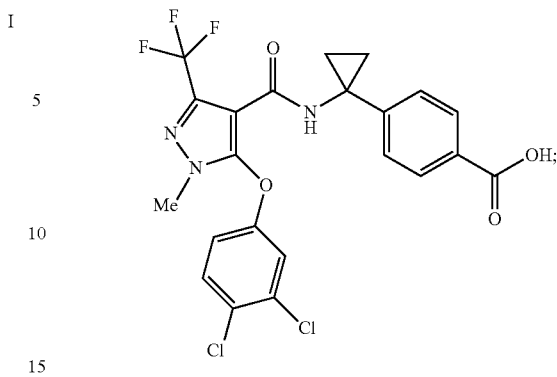

or a pharmaceutically acceptable salt thereof;
and a pharmaceutically acceptable carrier.

17. A method of treating multiple sclerosis in a mammal, comprising the step of administering to the mammal a pharmaceutical composition comprising a compound of formula I:

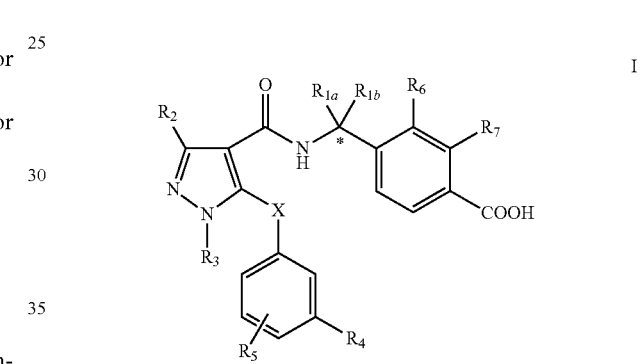

wherein:
- one of $R_{1a}$ and $R_{1b}$ is hydrogen, and the other is methyl; or $R_{1a}$ and $R_{1b}$ are taken together to form a cyclopropyl ring;
- $R_2$ is methyl or fluoromethyl;
- $R_3$ is methyl;
- $R_4$ is hydrogen, halo, methyl, fluoromethyl, methoxy, or fluoromethoxy;
- $R_5$ is hydrogen, halo, methyl, fluoromethyl, methoxy, or fluoromethoxy;
- $R_6$ is hydrogen, halo, methyl, or methoxy;
- $R_7$ is hydrogen, halo, methyl, or methoxy; and
- X is oxygen;

or a pharmaceutically acceptable salt thereof.

18. A method of treating multiple sclerosis in a mammal, comprising the step of administering to the mammal a pharmaceutical composition comprising a compound of claim 10, or a pharmaceutically acceptable salt thereof.

19. A method of treating multiple sclerosis in a mammal, comprising the step of administering to the mammal a pharmaceutical composition comprising the compound of claim 10 which is:

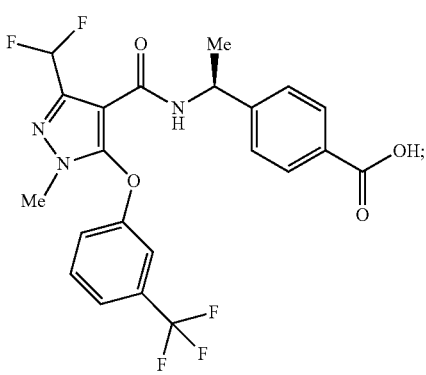

or a pharmaceutically acceptable salt thereof.

20. A method of treating multiple sclerosis in a mammal, comprising the step of administering to the mammal a pharmaceutical composition comprising the compound of claim 10 which is:

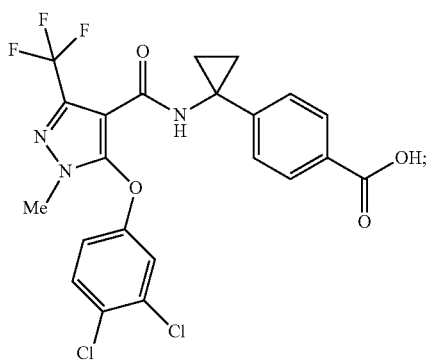 [SMILES: Cn1nc(C(F)(F)F)c(C(=O)NC2(c3ccc(C(=O)O)cc3)CC2)c1Oc1ccc(Cl)c(Cl)c1]

or a pharmaceutically acceptable salt thereof.

21. A method of treating rheumatoid arthritis in a mammal, comprising the step of administering to the mammal a pharmaceutical composition comprising a compound of formula I:

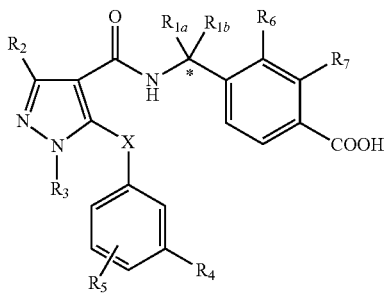

wherein:
one of $R_{1a}$ and $R_{1b}$ is hydrogen, and the other is methyl; or $R_{1a}$ and $R_{1b}$ are taken together to form a cyclopropyl ring;

$R_2$ is methyl or fluoromethyl;
$R_3$ is methyl;
$R_4$ is hydrogen, halo, methyl, fluoromethyl, methoxy, or fluoromethoxy;
$R_5$ is hydrogen, halo, methyl, fluoromethyl, methoxy, or fluoromethoxy;
$R_6$ is hydrogen, halo, methyl, or methoxy;
$R_7$ is hydrogen, halo, methyl, or methoxy; and
X is oxygen;
or pharmaceutically acceptable salts thereof.

22. A method of treating rheumatoid arthritis in a mammal, comprising the step of administering to the mammal a pharmaceutical composition comprising a compound of claim 10, or a pharmaceutically acceptable salt thereof.

23. A method of treating rheumatoid arthritis in a mammal, comprising the step of administering to the mammal a pharmaceutical composition comprising the compound of claim 10 which is:

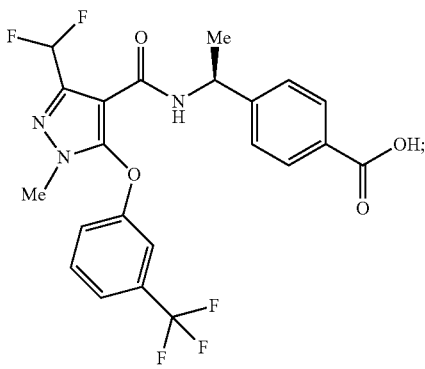

or a pharmaceutically acceptable salt thereof.

24. A method of treating rheumatoid arthritis in a mammal, comprising the step of administering to the mammal a pharmaceutical composition comprising the compound of claim 10 which is:

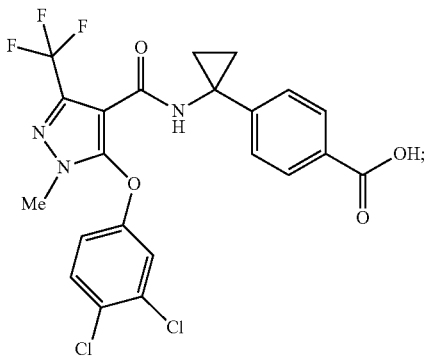 [SMILES: Cn1nc(C(F)(F)F)c(C(=O)NC2(c3ccc(C(=O)O)cc3)CC2)c1Oc1ccc(Cl)c(Cl)c1]

or a pharmaceutically acceptable salt thereof.

* * * * *

UNITED STATES PATENT AND TRADEMARK OFFICE
CERTIFICATE OF CORRECTION

Page 1 of 2

PATENT NO. : 8,686,018 B2
APPLICATION NO. : 13/795768
DATED : April 1, 2014
INVENTOR(S) : Spyvee et al.

It is certified that error appears in the above-identified patent and that said Letters Patent is hereby corrected as shown below:

In the Claims:
Column 124, Claim 10, Line 65: Please correct the compound below:

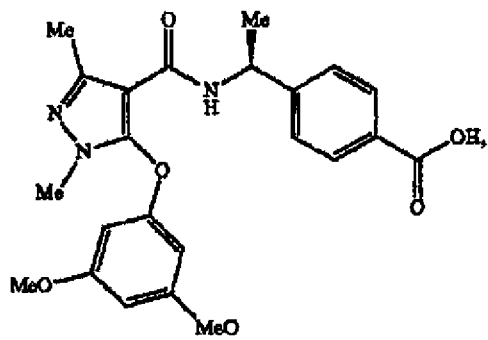

to read as:

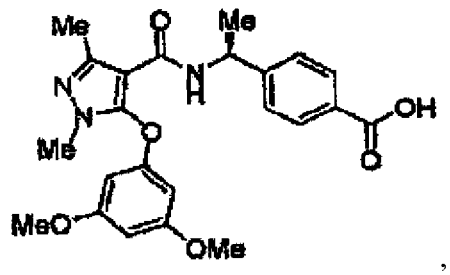

,

Signed and Sealed this
Twenty-fourth Day of March, 2015

Michelle K. Lee
*Director of the United States Patent and Trademark Office*

CERTIFICATE OF CORRECTION (continued)
U.S. Pat. No. 8,686,018 B2

Column 130, Claim 10, Line 45: Please correct the compound below:

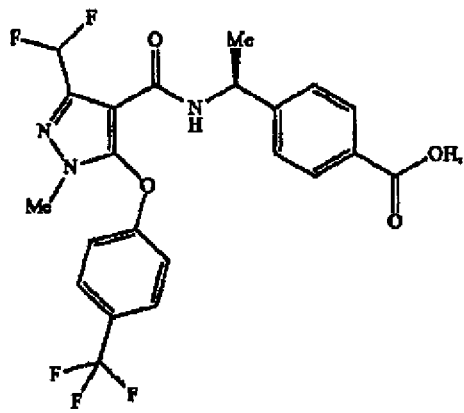

to read as:

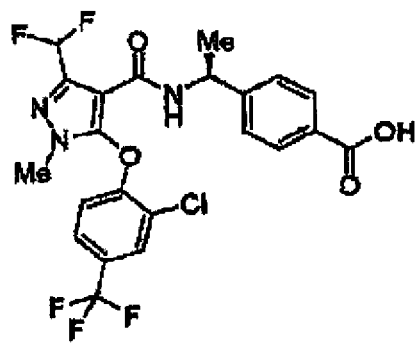

UNITED STATES PATENT AND TRADEMARK OFFICE
CERTIFICATE OF CORRECTION

PATENT NO. : 8,686,018 B2
APPLICATION NO. : 13/795768
DATED : April 1, 2014
INVENTOR(S) : Mark Spyvee, Takashi Satoh and Jonathan Eric Carlson It is certified that error appears in the above-identified patent and that said Letters Patent is hereby corrected as shown below:

In the specification

In Column 20, lines 30-31, the term:

"5-chloro-3-(difluoromethyl)-1-methyl-4H-pyrazole-4-carbaldehyde"

should read:

--5-chloro-3-(difluoromethyl)-1-methyl-1H-pyrazole-4-carbaldehyde--.

Signed and Sealed this
Twenty-ninth Day of November, 2016

Michelle K. Lee
*Director of the United States Patent and Trademark Office*